(12) United States Patent
Anderson et al.

(10) Patent No.: US 10,793,559 B2
(45) Date of Patent: Oct. 6, 2020

(54) CHEMICAL COMPOUNDS

(71) Applicant: GlaxoSmithKline Intellectual Property Development Limited, Brentford, Middlesex (GB)

(72) Inventors: Niall Andrew Anderson, Stevenage (GB); Nicholas Paul Barton, Stevenage (GB); Sebastien Andre Campos, Stevenage (GB); Edward Paul Cannons, Stevenage (GB); Anthony William James Cooper, Stevenage (GB); Kenneth David Down, Stevenage (GB); Kevin James Doyle, Saffron Walden (GB); Julie Nicole Hamblin, Stevenage (GB); Graham George Adam Inglis, Stevenage (GB); Armelle Le Gall, Stevenage (GB); Vipulkumar Kantibhai Patel, Stevenage (GB); Simon Peace, Stevenage (GB); Andrew Sharpe, Saffron Walden (GB); Gemma Victoria White, Stevenage (GB)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 16/572,917

(22) Filed: Sep. 17, 2019

(65) Prior Publication Data
US 2020/0071311 A1  Mar. 5, 2020

Related U.S. Application Data

(62) Division of application No. 16/073,355, filed as application No. PCT/EP2017/052954 on Feb. 10, 2017, now Pat. No. 10,457,674.

(30) Foreign Application Priority Data

Feb. 12, 2016 (GB) .................................. 1602527.2

(51) Int. Cl.
| C07D 413/14 | (2006.01) |
| C07D 213/76 | (2006.01) |
| A61P 25/28 | (2006.01) |
| A61P 11/06 | (2006.01) |
| A61P 37/08 | (2006.01) |
| A61P 25/24 | (2006.01) |
| A61P 15/08 | (2006.01) |

(52) U.S. Cl.
CPC ............ *C07D 413/14* (2013.01); *A61P 11/06* (2018.01); *A61P 15/08* (2018.01); *A61P 25/24* (2018.01); *A61P 25/28* (2018.01); *A61P 37/08* (2018.01); *C07D 213/76* (2013.01)

(58) Field of Classification Search
CPC ........... A61P 11/06; A61P 15/08; A61P 25/24; A61P 25/28; A61P 37/08; C07D 213/76; C07D 413/14
See application file for complete search history.

(56) References Cited

FOREIGN PATENT DOCUMENTS

| WO | 2008/118455 A1 | 10/2008 |
| WO | 2009/055418 A1 | 4/2009 |

OTHER PUBLICATIONS

Yang et al. (Molecular Cancer, 2019, 18:26) (Year: 2019).*
Greenamyre—UPMC—Department of Neurology (University of Pittsburg), 2012 (Year: 2012).*
Johnson et al., (British J. of Cancer 2001, p. 1424-1431) (Year: 2001).*
Gura et al. (Science 1997, Nov. 7, 278) (Year: 2997).*
Neidle, Stephen, ed., Cancer Drug Design and Discovery:(Elsevier/Academic Press, 2008) (Year: 2008).*
Cecil Textbook of Medicine, 20th Edition, vol. 1, 1996 (Year: 1996).*
Cecil reference (Cecil Textbook of Medicine, 2000) (Year: 2000).*
Lowe, Sciencemag.org, Nov. 2018 (Year: 2018).*
(Massacesi, Annals of the New York Academy of Sciences, 2013, p. 19-23). (Year: 2013).*

* cited by examiner

*Primary Examiner* — Umamaheswari Ramachandran
(74) *Attorney, Agent, or Firm* — Robert J. Smith

(57) ABSTRACT

The invention is directed to certain novel compounds. Specifically, the invention is directed to compounds of formula (I):

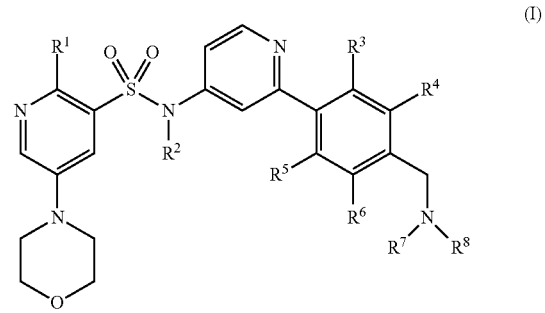

and salts thereof. The compounds of the invention are inhibitors of kinase activity, in particular PI3-kinase activity.

3 Claims, 4 Drawing Sheets

CHEMICAL COMPOUNDS

CROSS-REFERENCE TO RELATED APPLICATIONS

This application is a divisional application of Ser. No. 16/073,355, filed 27 Jul. 2018, now allowed, which was filed pursuant to 35 U.S.C. § 371 as a United States National Phase Application of International Application No. PCT/EP2017/052954 filed 10 Feb. 2017 which claims priority from GB 1602527.2 filed 12 Feb. 2016.

FIELD OF THE INVENTION

The present invention is directed to compounds which are inhibitors of kinase activity, pharmaceutical compositions comprising the compounds, and the use of the compounds or the compositions in the treatment of various disorders. More specifically, the compounds of the invention are inhibitors of the activity or function of the phosphoinositide 3'OH kinase family (hereinafter PI3-kinases), for example PI3Kδ, PI3Kα, PI3Kβ and/or PI3Kγ.

BACKGROUND OF THE INVENTION

Cellular membranes represent a large store of second messengers that can be enlisted in a variety of signal transduction pathways. In relation to function and regulation of effector enzymes in phospholipids signalling pathways, class I PI3-kinases (e.g. PI3Kdelta) generate second messengers from the membrane phospholipid pools. Class I PI3Ks convert the membrane phospholipid $PI(4,5)P_2$ into $PI(3,4,5)P_3$, which functions as a second messenger. PI and PI(4)P are also substrates of PI3K and can be phosphorylated and converted into PI3P and $PI(3,4)P_2$, respectively. In addition, these phosphoinositides can be converted into other phosphoinositides by 5'-specific and 3'-specific phosphatases. Thus, PI3K enzymatic activity results either directly or indirectly in the generation of two 3'-phosphoinositide subtypes which function as second messengers in intracellular signal transduction pathways (Trends Biochem. Sci. 22(7) p. 267-72 (1997) by Vanhaesebroeck et al.; Chem. Rev. 101(8) p. 2365-80 (2001) by Leslie et al.; Annu. Rev. Cell Dev. Biol. 17 p. 615-75 (2001) by Katso et al.; and Cell. Mol. Life Sci. 59(5) p. 761-79 (2002) by Toker). To date, eight mammalian PI3Ks have been identified, divided into three main classes (I, II, and III) on the basis of sequence homology, structure, binding partners, mode of activation, and substrate preference. In vitro, class I PI3Ks can phosphorylate phosphatidylinositol (PI), phosphatidylinositol-4-phosphate (PI4P), and phosphatidylinositol-4,5-bisphosphate (PI(4,5)P2) to produce phosphatidylinositol-3-phosphate (PI3P), phosphatidylinositol-3,4-bisphosphate (PI(3,4)P2, and phosphatidylinositol-3,4,5-trisphosphate (PI (3,4,5)P3, respectively. Class II PI3Ks can phosphorylate PI and PI4P. Class III PI3Ks can only phosphorylate PI (Vanhaesebroeck et al. (1997), above; Vanhaesebroeck et al. Exp. Cell Res. 253(1) p. 239-54 (1999); and Leslie et al. (2001), above).

Class I PI3K is a heterodimer consisting of a p110 catalytic subunit and a regulatory subunit, and the family is further divided into class Ia and class Ib enzymes on the basis of regulatory partners and mechanism of regulation. Class Ia enzymes consist of three distinct catalytic subunits (p110α, p110β, and p110δ) that dimerise with five distinct regulatory subunits (p85α, p55α, p50α, p85β, and p55γ), with all catalytic subunits being able to interact with all regulatory subunits to form a variety of heterodimers. Class Ia PI3K are generally activated in response to growth factor-stimulation of receptor tyrosine kinases, via interaction of the regulatory subunit SH2 domains with specific phospho-tyrosine residues of the activated receptor or adaptor proteins such as IRS-1. Small GTPases (ras as an example) are also involved in the activation of PI3K in conjunction with receptor tyrosine kinase activation. Both p110α and p110β are constitutively expressed in all cell types, whereas p110δ expression is more restricted to leukocyte populations and some epithelial cells. In contrast, the single Class Ib enzyme consists of a p110γ catalytic subunit that interacts with a p101 regulatory subunit.

Furthermore, the Class Ib enzyme is activated in response to G-protein coupled receptor (GPCR) systems and its expression appears to be limited to leukocytes.

Scheme A: Conversion of $PI(4,5)P_2$ to $PI(3,4,5)P_3$

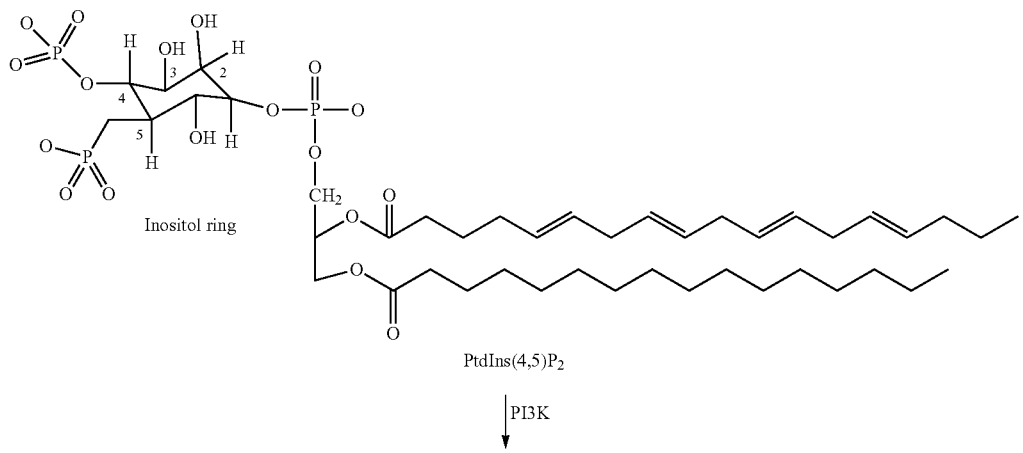

PtdIns(4,5)P2

PI3K

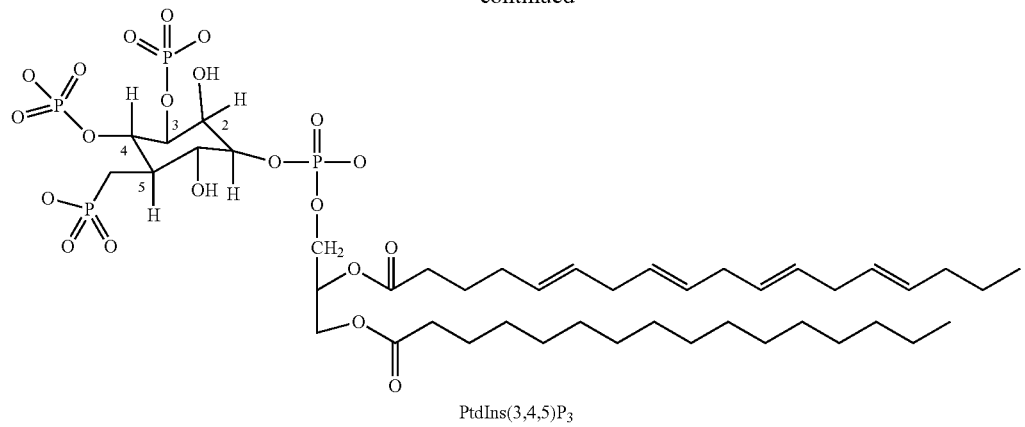

PtdIns(3,4,5)P$_3$

As illustrated in Scheme A above, phosphoinositide 3-kinases (PI3Ks) phosphorylate the hydroxyl of the third carbon of the inositol ring. The phosphorylation of phosphoinositides to generate PtdIns(3,4,5)P$_3$, PtdIns(3,4)P$_2$ and PtdIns(3)P, produces second messengers for a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement, cell shape changes, vesicle trafficking and metabolic pathway (Katso et al. (2001), above; and Mol. Med. Today 6(9) p. 347-57 (2000) by Stein et al.).

The activity of PI3-kinases responsible for generating these phosphorylated signalling products was originally identified as being associated with viral oncoproteins and growth factor receptor tyrosine kinases that phosphorylate phosphatidylinositol (PI) and its phosphorylated derivatives at the 3'-hydroxyl of the inositol ring (Panayotou et al. Trends Cell Biol. 2 p. 358-60 (1992)). However, more recent biochemical studies have revealed that class I PI3-kinases (e.g. class IA isoform PI3Kδ) are dual-specific kinase enzymes, meaning they display both lipid kinase (phosphorylation of phosphoinositides) as well as protein kinase activity, which have been shown to be capable of phosphorylation of other protein as substrates, including auto-phosphorylation as an intramolecular regulatory mechanism (EMBO J. 18(5) p. 1292-302 (1999) by Vanhaesebroeck et al.). Cellular processes in which PI3Ks play an essential role include suppression of apoptosis, reorganization of the actin skeleton, cardiac myocyte growth, glycogen synthase stimulation by insulin, TNFα-mediated neutrophil priming and superoxide generation, and leukocyte migration and adhesion to endothelial cells.

PI3-kinase activation, is believed to be involved in a wide range of cellular responses including cell growth, differentiation, and apoptosis (Parker, Current Biology 5(6) p. 577-79 (1995); and Yao et al. Science 267(5206) p. 2003-06 (1995)). PI3-kinase appears to be involved in a number of aspects of leukocyte activation. A p85-associated PI3-kinase has been shown to physically associate with the cytoplasmic domain of CD28, which is an important costimulatory molecule for the activation of T-cells in response to antigen (Pages et al. Nature 369 p. 327-29 (1994); and Rudd, Immunity 4 p. 527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al. Science 251(4991) p. 313-16 (1991)).

PI3Kγ has been identified as a mediator of G beta-gamma-dependent regulation of JNK activity, and G beta-gamma are subunits of heterotrimeric G proteins (Lopez-Ilasaca et al. J. Biol. Chem. 273(5) p. 2505-8 (1998)). Recently, (Laffargue et al. Immunity 16(3) p. 441-51 (2002)) it has been described that PI3Kγ relays inflammatory signals through various G(i)-coupled receptors and is central to mast cell function, stimuli in the context of leukocytes, and immunology including cytokines, chemokines, adenosines, antibodies, integrins, aggregation factors, growth factors, viruses or hormones for example (J. Cell Sci. 114 (Pt 16) p. 2903-10 (2001) by Lawlor et al.; Laffargue et al. (2002), above; and Curr. Opinion Cell Biol. 14(2) p. 203-13 (2002) by Stephens et al.).

Specific inhibitors against individual members of a family of enzymes provide invaluable tools for deciphering functions of each enzyme. Two compounds, LY294002 and wortmannin (hereinafter), have been widely used as PI3-kinase inhibitors. These compounds are non-specific PI3K inhibitors, as they do not distinguish among the four members of Class I PI3-kinases. For example, the IC$_{50}$ values of wortmannin against each of the various Class I PI3-kinases are in the range of 1-10 nM. Similarly, the IC$_{50}$ values for LY294002 against each of these PI3-kinases is about 15-20 μM (Fruman et al. Ann. Rev. Biochem. 67 p. 481-507 (1998)), also 5-10 microM on CK2 protein kinase and some inhibitory activity on phospholipases. Wortmannin is a fungal metabolite which irreversibly inhibits PI3K activity by binding covalently to the catalytic domain of this enzyme. Inhibition of PI3K activity by wortmannin eliminates subsequent cellular response to the extracellular factor. For example, neutrophils respond to the chemokine fMet-Leu-Phe (fMLP) by stimulating PI3K and synthesizing PtdIns (3, 4, 5)P$_3$. This synthesis correlates with activation of the respiratory burst involved in neutrophil destruction of invading microorganisms. Treatment of neutrophils with wortmannin prevents the fMLP-induced respiratory burst response (Thelen et al. Proc. Natl. Acad. Sci. USA 91 p. 4960-64 (1994)). Indeed, these experiments with wortmannin, as well as other experimental evidence, show that PI3K activity in cells of hematopoietic lineage, particularly neutrophils, monocytes, and other types of leukocytes, is involved in many of the non-memory immune response associated with acute and chronic inflammation.

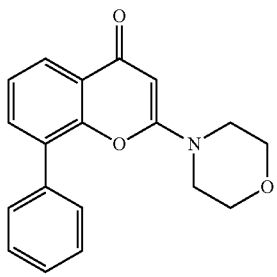

LY294002

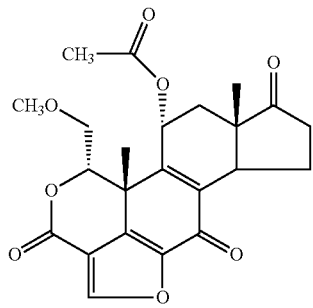

WORTMANNIN

Based on studies using wortmannin, there is evidence that PI3-kinase function is also required for some aspects of leukocyte signaling through G-protein coupled receptors (Thelen et al. (1994), above). Moreover, it has been shown that wortmannin and LY294002 block neutrophil migration and superoxide release.

It is now well understood that deregulation of oncogenes and tumour suppressor genes contributes to the formation of malignant tumours, for example by way of increased cell growth and proliferation or increased cell survival. It is also now known that signalling pathways mediated by the PI3K family have a central role in a number of cell processes including proliferation and survival, and deregulation of these pathways is a causative factor a wide spectrum of human cancers and other diseases (Katso et al. Annual Rev. Cell Dev. Biol. (2001) 17 p. 615-675 and Foster et al. J. Cell Science (2003) 116(15) p. 3037-3040). PI3K effector proteins initiate signalling pathways and networks by translocating to the plasma membrane through a conserved Pleckstrin Homology (PH) domain, which specifically interacts with PtdIns(3,4,5)P3 (Vanhaesebroeck et al. Annu. Rev. Biochem. (2001) 70 p. 535-602). The effector proteins signalling through PtdIns(3,4,5)P3 and PH domains include Serine/Threonine (Ser/Thr) kinases, Tyrosine kinases, Rac or Arf GEFs (Guanine nucleotide exchange factors) and Arf GAPS (GTPase activating proteins).

In B and T cells PI3Ks have an important role through activation of the Tec family of protein tyrosine kinases which include Bruton's tyrosine kinase (BTK) in B cells and Interleukin-2-inducible T-cell kinase (ITK) in T cells. Upon PI3K activation, BTK or ITK translocate to the plasma membrane where they are subsequently phosphorylated by Src kinases. One of the major targets of activated ITK is phospholipase C-gamma (PLCγ1), which hydrolyses PtdIns (4,5)P2 into Ins(3,4,5)P3 and initiates an intracellular increase in calcium levels and diacylglycerol (DAG) which can activate Protein Kinases C in activated T cells.

Unlike the Class IA p110α and p110β, p110δ is expressed in a tissue restricted fashion. Its high expression level in lymphocytes and lymphoid tissues suggests a role in PI3K-mediated signalling in the immune system. The p110δ kinase dead knock-in mice are also viable and their phenotype is restricted to defects in immune signalling (Okkenhaug et al. Science (2002) 297 p. 1031-4). These transgenic mice have offered insight into the function of PI3Kδ in B-cell and T-cell signalling. In particular, p110δ is required for PtdIns(3,4,5)P3 formation downstream of CD28 and/or T cell Receptor (TCR) signalling. A key effect of PI3K signalling downstream of TCR is the activation of Akt, which phosphorylates anti-apoptotic factors as well as various transcription factors for cytokine production. As a consequence, T cells with inactive p110δ have defects in proliferation and Th1 and Th2 cytokine secretion. Activation of T cells through CD28 lowers the threshold for TCR activation by antigen and increases the magnitude and duration of the proliferative response. These effects are mediated by the PI3Kδ-dependent increase in the transcription of a number of genes including IL2, an important T cell growth factor.

Therefore, PI3K inhibitors are anticipated to provide therapeutic benefit via its role in modulating T-cell mediated inflammatory responses associated to respiratory diseases such as asthma, COPD and cystic fibrosis. In addition, there is indication that T-cell directed therapies may provide corticosteroid sparing properties (Alexander et al. Lancet (1992) 339 p. 324-8) suggesting that it may provide a useful therapy either as a standalone or in combination with inhaled or oral glucocorticosteroids in respiratory diseases. A PI3K inhibitor might also be used alongside other conventional therapies such as a long acting beta-agonist (LABA) or leukotriene antagonist in asthma.

In the vasculature, PI3Kδ is expressed by endothelial cells and participates in neutrophil trafficking by modulating the proadhesive state of these cells in response to TNFalpha (Puri et al. Blood (2004) 103(9) p. 3448-56.). A role for PI3Kδ in TNFalpha-induced signalling of endothelial cells is demonstrated by the pharmacological inhibition of Akt phosphorylation and PDK1 activity. In addition, PI3Kδ is implicated in vascular permeability and airway tissue edema through the VEGF pathway (Lee et al. J. Allergy Clin. Immunol. (2006) 118(2) p. 403-9). These observations suggest additional benefits of PI3Kδ inhibition in asthma by the combined reduction of leukocyte extravasation and vascular permeability associated with asthma. In addition, PI3Kδ activity is required for mast cell function both in vitro and in vivo (Ali et al. Nature (2004) 431 p. 1007-11; and Ali et al. J. Immunol. (2008) 180(4) p. 2538-44) further suggesting that PI3K inhibition should be of therapeutical benefit for allergic indications such asthma, allergic rhinitis and atopic dermatitis.

The role of PI3Kδ in B cell proliferation, antibody secretion, B-cell antigen and IL-4 receptor signalling, B-cell antigen presenting function is also well established Okkenhaug et al. (2002), above; Al-Alwan et al. J. Immunol. (2007) 178(4) p. 2328-35; and Bilancio et al. Blood (2006) 107(2) p. 642-50) and indicates a role in autoimmune diseases such as rheumatoid arthritis or systemic lupus erythematosus (SLE). Therefore PI3K inhibitors may also be of benefit for these indications.

Pharmacological inhibition of PI3Kδ inhibits fMLP-dependent neutrophil chemotaxis on an ICAM coated agarose matrix integrin-dependent biased system (Sadhu et al., J. Immunol. (2003) 170(5) p. 2647-54.). Inhibition of PI3Kδ regulates neutrophil activation, adhesion and migration without affecting neutrophil mediated phagocytosis and bactericidal activity over *Staphylococcus aureus* (Sadhu et al. Biochem. Biophys. Res. Commun. (2003) 308(4) p. 764-9). Overall, the data suggest that PI3Kδ inhibition should not globally inhibit neutrophil functions required for innate immune defence. PI3Kδ's role in neutrophils offers further scope for treating inflammatory diseases involving tissue remodeling such as COPD or rheumatoid arthritis. PI3Kδ inhibition may also lead to cancer immunotherapy. For instance, PI3Kδ has a critical signalling role in regulatory T cells (Tregs), which enables their expansion (Patton et al. PLoS One. 2011; 6(3):e17359). Activation of Tregs is one of the key processes that allow cancer cells to build immunological tolerance and escape immune surveillance. Another aspect of cancer immunity where PI3Kδ inhibitors may play a role is in upregulating the expression of PD-L1 (Programmed cell death 1 ligand 1) as has been shown in cultured airway epithelial cells (Kan-0 et al. Biochem Biophys Res Commun. 2013; 435(2):195-201). PD-L1, expressed on various cell types such as T and B lymphocytes, NK and DC cells or epithelial cells, is involved in suppressing T cell dependent immunity such as the activation of cytotoxic CD8 T cells. Neutralising antibodies targeting PD-L1 are currently being developed as cancer immuno-therapeutics. Therefore, PI3Kδ inhibition may provide a novel way of enhancing anti-tumour responses. A similar rationale may also be applied to anti-infective immunity where the balance of Tregs and CD8s are known to play an important role in the outcome of the immune response such as viral infections.

The central nervous system (CNS) is also enriched with PI3Kδ expression (Eickholt et al. PLoS One 2007 11; 2(9):e869). A more recent report further uncovered a link between PI3Kδ and the neuregulin NRC-1 and ErbB4 receptor in the CNS with implications for schizophrenia (Law et al. Proc Natl Acad Sci USA. 2012; 109(30):12165-70). It was previously known that increased expression of a splice variant of ErbB4 containing the cytoplasmic portion, Cyt1, resulted in activation of the PI3K pathway as well as increased risk of schizophrenia. The publication by Law et al. indicates that the schizophrenia genetically associated Cyt1 couples preferentially to the PI3Kδ isoform. Furthermore, the PI3Kδ selective inhibitor, IC87114, showed remarkable efficacy in a mouse model of amphetamine-induced psychosis (Law et al. Proc Natl Acad Sci USA. 2012; 109(30):12165-70). Therefore PI3Kδ inhibitors have the potential to form the basis for new schizophrenia therapy approaches.

In addition, there is also good evidence that class IA PI3K enzymes also contribute to tumourigenesis in a wide variety of human cancers, either directly or indirectly (Vivanco and Sawyers, Nature Reviews Cancer (2002) 2(7) p. 489-501). For example, inhibition of PI3Kδ may have a therapeutic role for the treatment of malignant haematological disorders such as acute myeloid leukaemia (Billottet et al. Oncogene (2006) 25(50) p. 6648-59). Moreover, activating mutations within p110a (PIK3CA gene) have been associated with various other tumours such as those of the colon and of the breast and lung (Samuels et al. Science (2004) 304(5670) p. 554).

It has also been shown that PI3K is involved in the establishment of central sensitization in painful inflammatory conditions (Pezet et al. The J. of Neuroscience (2008) 28 (16) p. 4261-4270).

A wide variety of retroviruses and DNA based viruses activate the PI3K pathway as a way of preventing host cell death during viral infection and ultimately exploiting the host cell synthesis machinery for its replication (Virology 344(1) p. 131-8 (2006) by Vogt et al.; and Nat. Rev. Microbiol. 6(4) p. 265-75 (2008) by Buchkovich et al.). Therefore PI3K inhibitors may have anti-viral properties in addition to more established oncolytic and anti-inflammatory indications. These antiviral effects raise interesting prospects in viral induced inflammatory exacerbations. For example, the common cold human rhinovirus (HRV) is responsible for more than 50% of respiratory tract infections but complications of these infections can be significant in certain populations. This is particularly the case in respiratory diseases such as asthma or chronic obstruction pulmonary disease (COPD). Rhinoviral infection of epithelial cells leads to a PI3K dependent cytokine and chemokine secretion (J. Biol. Chem. (2005) 280(44) p. 36952 by Newcomb et al.). This inflammatory response correlates with worsening of respiratory symptoms during infection. Therefore PI3K inhibitors may dampen an exaggerated immune response to an otherwise benign virus. The majority of HRV strains infect bronchial epithelial cells by initially binding to the ICAM-1 receptor. The HRV-ICAM-1 complex is then further internalised by endocytosis and it has been shown that this event requires PI3K activity (J. Immunol. (2008) 180(2) p. 870-880 by Lau et al.). Therefore, PI3K inhibitors may also block viral infections by inhibiting viral entry into host cells.

PI3K inhibitors may be useful in reducing other types of respiratory infections including the fungal infection aspergillosis (Mucosal Immunol. (2010) 3(2) p. 193-205 by Bonifazi et al.). In addition, PI3Kδ deficient mice are more resistant towards infections by the protozoan parasite Leishmania major (J. Immunol. (2009) 183(3) p. 1921-1933 by Liu et al.) or by the intracellular bacteria Listeria (Pearce et al. J. Immunol. (2015) 195(7) p. 3206-17). Taken with effects on viral infections, these reports suggest that PI3K inhibitors may be useful for the treatment of a wide variety of infections.

A published report points towards PI3Kδ inhibitors having potential benefits in preventing infections by the common airway bacterial pathogen *S. Pneumoniae* (Fallah et al., Mech. Ageing Dev. 2011; 132(6-7): 274-86). In this report PI3Kδ is shown to reduce the macrophage-derived cytokines required to mount an effective antibody response to *S. pneumoniae* in the elderly. The anti-bacterial benefit of PI3Kδ inhibitors may thus be useful in the treatment of bacterial respiratory tract infections and bacterial exacerbations of respiratory conditions and lung damage such as asthma, COPD and cystic fibrosis, and pneumonia.

PI3K inhibition has also been shown to promote regulatory T cell differentiation (Proc. Natl. Acad. Sci. USA (2008) 105(22) p. 7797-7802 by Sauer et al.) suggesting that PI3K inhibitors may serve therapeutic purposes in auto-immune or allergic indications by inducing immuno-tolerance towards self antigen or allergen. The PI3Kδ isoform has also been linked to smoke induced glucocorticoid insensitivity (Am. J. Respir. Crit. Care Med. (2009) 179(7) p. 542-548 by Marwick et al.). This observation suggests that COPD patients, which otherwise respond poorly to corticosteroids, may benefit from the combination of a PI3K inhibitor with a corticosteroid.

PI3K has also been involved in other respiratory conditions such as idiopathic pulmonary fibrosis (IPF). IPF is a fibrotic disease with progressive decline of lung function and increased mortality due to respiratory failure. In IPF, circulating fibrocytes are directed to the lung via the chemokine receptor CXCR4. PI3K is required for both signalling and expression of CXCR4 (Int. J. Biochem. and Cell Biol. (2009) 41 p. 1708-1718 by Mehrad et al.). Therefore, by reducing CXCR4 expression and blocking its effector function, a PI3K inhibitor should inhibit the recruitment of fibrocytes to the lung and consequently slow down the fibrotic process underlying IPF, a disease with high unmet need.

Attempts have been made to prepare compounds which inhibit PI3-kinase activity and a number of such compounds have been disclosed in the art. However, in view of the number of pathological responses which are mediated by PI3-kinases, there remains a continuing need for inhibitors of PI3-kinase which can be used in the treatment of a variety of conditions.

The present inventors have discovered compounds which are inhibitors of kinase activity, in particular PI3-kinase activity. Compounds which are PI3-kinase inhibitors may be useful in the treatment of disorders associated with inappropriate kinase activity, in particular inappropriate PI3-kinase activity, for example in the treatment and prevention of disorders mediated by PI3-kinase mechanisms. Such disorders include respiratory diseases including asthma, chronic obstructive pulmonary disease (COPD) and idiopathic pulmonary fibrosis (IPF); ciliopathy including primary ciliary dyskinesia, polycystic liver disease and nephronophthisis; bacterial infections including bacterial respiratory tract infections, for example infections by S. Pneumoniae, H. Influenzae, M. Catarrhalis and/or mycobacteria such as Mycobacterium tuberculosis, and bacterial exacerbations of respiratory conditions and lung damage such as asthma, COPD and cystic fibrosis; viral infections including viral respiratory tract infections, for example infections by influenza, rhinovirus, respiratory syncytial virus (RSV), human parainfluenza virus (HPIV), adenovirus and/or coronavirus, and viral exacerbation of respiratory conditions and lung damage such as asthma, COPD and cystic fibrosis; other non-viral respiratory infections including aspergillosis and leishmaniasis; allergic diseases including allergic rhinitis, atopic dermatitis and psoriasis; autoimmune diseases including ankylosing spondylitis, Churg-Strauss syndrome, Crohn's disease, Glomerulonephritis, Henoch-Schonlein purpura, idiopathic thrombocytopenic purpura (ITP), interstitial cystitis, pemphigus, primary sclerosing cholangitis, psoriasis, rheumatoid arthritis, sarcoidosis, Sjogren's syndrome, Type 1 diabetes, ulcerative colitis, vasculitis and Wegener's granulomatosis; inflammatory disorders including inflammatory bowel disease; diabetes; cardiovascular diseases including thrombosis, atherosclerosis and hypertension;

hematologic malignancies; neurodegenerative diseases; pancreatitis; multiorgan failure; kidney diseases; platelet aggregation; cancer; sperm motility; transplantation rejection; graft rejection; lung injuries; pain including pain associated with rheumatoid arthritis or osteoarthritis, back pain, general inflammatory pain, post hepatic neuralgia, diabetic neuropathy, inflammatory neuropathic pain (trauma), trigeminal neuralgia and Central pain; fibrotic diseases; depression; and psychotic disorders including schizophrenia.

In one embodiment, compounds of the invention may show selectivity for PI3-kinases over other kinases.

In another embodiment, compounds of the invention may be potent inhibitors of PI3Kδ.

In another embodiment, compounds of the invention may show selectivity for PI3Kδ over other PI3-kinases.

In a further embodiment, compounds of the invention may have properties which make them particularly suitable for oral administration.

SUMMARY OF THE INVENTION

The invention is directed to certain novel compounds. Specifically, the invention is directed to compounds of formula (I)

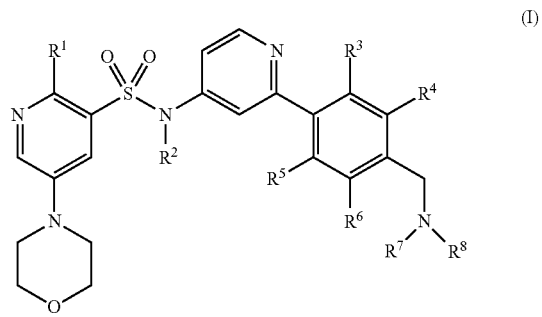

wherein $R^1$ to $R^8$ are as defined below, and salts thereof.

The compounds are inhibitors of kinase activity, in particular PI3-kinase activity. Compounds which are PI3-kinase inhibitors may be useful in the treatment of disorders associated with inappropriate PI3-kinase activity. Accordingly, the invention is further directed to pharmaceutical compositions comprising a compound of formula (I) or a pharmaceutically acceptable salt thereof, and one or more pharmaceutically acceptable excipients. The invention is still further directed to methods of treating disorders mediated by inappropriate PI3-kinase activity comprising administering a safe and effective amount of a compound of formula (I) or a pharmaceutically acceptable salt thereof, to a patient in need thereof.

DETAILED DESCRIPTION OF THE INVENTION

Figure 1:
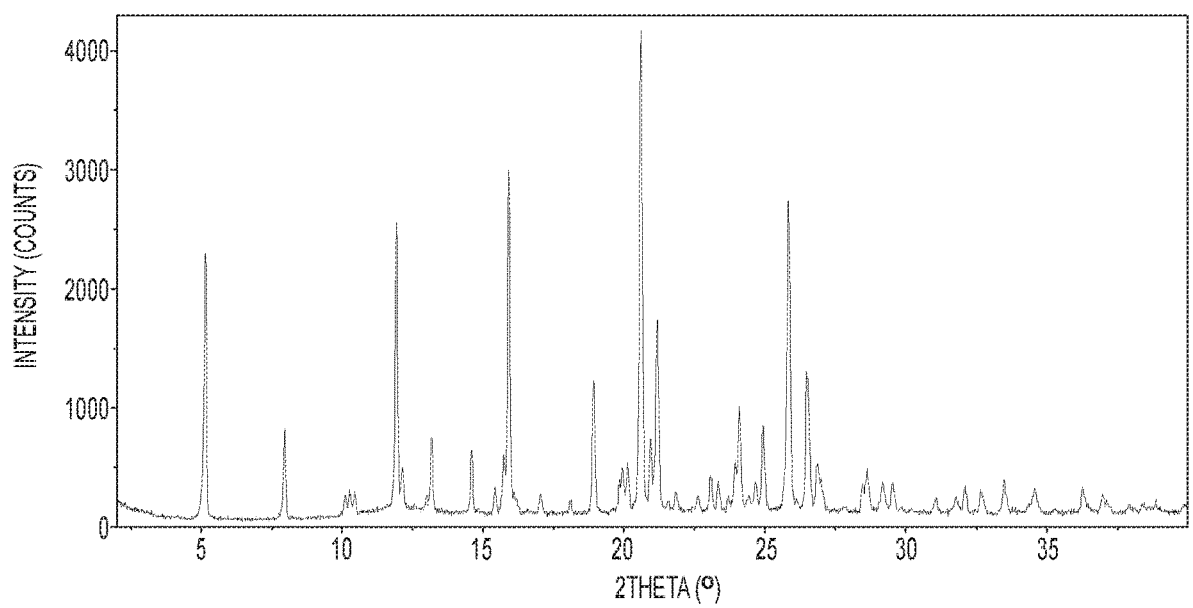
FIG. 1 shows an X-ray powder diffraction (XRPD) pattern for N-(2-(2-fluoro-4-((4-isopropylpiperazin-1-yl)methyl)phenyl)pyridin-4-yl)-2-methoxy-5-morpholinopyridine-3-sulfonamide (anhydrate—Form 1).

In one embodiment, the invention is directed to compounds of formula (I)

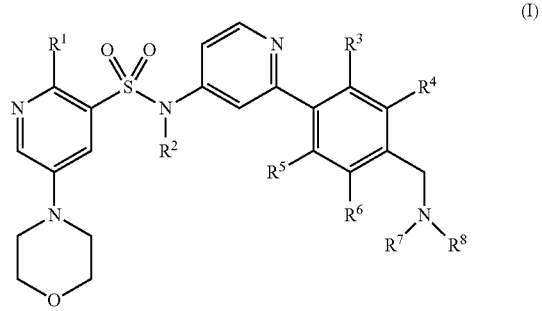

wherein

R$^1$ is C$_{1-6}$alkoxy or —N(C$_{1-6}$alkyl)$_2$;

R$^2$ is hydrogen or C$_{1-6}$alkyl optionally substituted by —C(O)OC$_{1-6}$alkyl or —OC(O)C$_{1-6}$alkyl;

R$^3$, R$^4$, R$^5$ and R$^6$ are each independently selected from hydrogen and halogen;

R$^7$ and R$^8$ are each independently C$_{1-6}$alkyl, or

R$^7$ and R$^8$, together with the nitrogen atom to which they are attached, are linked to form a 5- or 6-membered heterocyclyl wherein the 5- or 6-membered heterocyclyl optionally contains a further nitrogen atom and is optionally substituted by C$_{3-6}$cycloalkyl, 4- to 6-membered heterocyclyl containing one or two heteroatoms independently selected from oxygen and nitrogen, or C$_{1-6}$alkyl wherein the C$_{1-6}$alkyl is optionally substituted by hydroxy or C$_{1-6}$alkoxy, or R$^7$ and R$^8$, together with the nitrogen atom to which they are attached, are linked to form a 5- or 6-membered heterocyclyl wherein the 5- or 6-membered heterocyclyl contains an oxygen atom and is optionally substituted by one or two substituents independently selected from C$_{1-6}$alkyl; and salts thereof (hereinafter "compounds of the invention").

In one embodiment, R$^1$ is C$_{1-6}$alkoxy. In a further embodiment, R$^1$ is methoxy.

In one embodiment, R$^2$ is hydrogen. In a further embodiment, R$^2$ is C$_{1-6}$alkyl.

In one embodiment, R$^3$, R$^4$, R$^5$ and R$^6$ are each independently selected from hydrogen and fluoro. In a further embodiment, R$^3$ is fluoro and R$^4$, R$^5$ and R$^6$ are each hydrogen.

In one embodiment, R$^7$ and R$^8$ are each methyl. In another embodiment, R$^7$ and R$^8$, together with the nitrogen atom to which they are attached, are linked to form a 5- or 6-membered heterocyclyl wherein the 5- or 6-membered heterocyclyl optionally contains a further nitrogen atom and is optionally substituted by C$_{3-6}$cycloalkyl, 4- to 6-membered heterocyclyl containing one or two heteroatoms independently selected from oxygen and nitrogen, or C$_{1-6}$alkyl wherein the C$_{1-6}$alkyl is optionally substituted by hydroxy or C$_{1-6}$alkoxy. In another embodiment, R$^7$ and R$^8$, together with the nitrogen atom to which they are attached, are linked to form a 6-membered heterocyclyl wherein the 6-membered heterocyclyl contains a further nitrogen atom and is optionally substituted by C$_{1-6}$alkyl. In a further embodiment, R$^7$ and R$^8$, together with the nitrogen atom to which they are attached, are linked to form a 6-membered heterocyclyl wherein the 6-membered heterocyclyl contains a further nitrogen atom and is substituted by C$_{1-6}$alkyl.

It is to be understood that the present invention covers all combinations of substituent groups described hereinabove.

Compounds of the invention include the compounds of Examples 1 to 37 and salts thereof.

In one embodiment, the compound of the invention is:

N-(2-(2-fluoro-4-((4-isopropylpiperazin-1-yl)methyl)phenyl)pyridin-4-yl)-2-methoxy-5-morpholinopyridine-3-sulfonamide;

N-(2-(4-((4-(tert-butyl)piperazin-1-yl)methyl)-2-fluorophenyl)pyridin-4-yl)-2-methoxy-5-morpholinopyridine-3-sulfonamide;

N-(2-(4-((4-isopropylpiperazin-1-yl)methyl)phenyl)pyridin-4-yl)-2-methoxy-5-morpholinopyridine-3-sulfonamide;

N-(2-(4-(((dimethylamino)methyl)phenyl)pyridin-4-yl)-2-methoxy-5-morpholinopyridine-3-sulfonamide;

N-(2-(3-fluoro-4-((4-isopropylpiperazin-1-yl)methyl)phenyl)pyridin-4-yl)-2-methoxy-5-morpholinopyridine-3-sulfonamide;

N-(2-(4-((4-(tert-butyl)piperazin-1-yl)methyl)phenyl)pyridin-4-yl)-2-methoxy-5-morpholinopyridine-3-sulfonamide;

N-(2-(4-((4-cyclobutylpiperazin-1-yl)methyl)phenyl)pyridin-4-yl)-2-methoxy-5-morpholinopyridine-3-sulfonamide;

N-(2-(2,6-difluoro-4-((4-isopropylpiperazin-1-yl)methyl)phenyl)pyridin-4-yl)-2-methoxy-5-morpholinopyridine-3-sulfonamide;

N-(2-(4-((4-(sec-butyl)piperazin-1-yl)methyl)phenyl)pyridin-4-yl)-2-methoxy-5-morpholinopyridine-3-sulfonamide;

N-(2-(2-fluoro-4-(pyrrolidin-1-ylmethyl)phenyl)pyridin-4-yl)-2-methoxy-5-morpholinopyridine-3-sulfonamide;

N-(2-(3-fluoro-4-(pyrrolidin-1-ylmethyl)phenyl)pyridin-4-yl)-2-methoxy-5-morpholinopyridine-3-sulfonamide;

N-(2-(3,5-difluoro-4-((4-isopropylpiperazin-1-yl)methyl)phenyl)pyridin-4-yl)-2-methoxy-5-morpholinopyridine-3-sulfonamide;

2-methoxy-5-morpholino-N-(2-(4-((4-(oxetan-3-yl)piperazin-1-yl)methyl)phenyl)pyridin-4-yl)pyridine-3-sulfonamide;

N-(2-(2,3-difluoro-4-((4-isopropylpiperazin-1-yl)methyl)phenyl)pyridin-4-yl)-2-methoxy-5-morpholinopyridine-3-sulfonamide;

N-(2-(2-fluoro-4-((4-(oxetan-3-yl)piperazin-1-yl)methyl)phenyl)pyridin-4-yl)-2-methoxy-5-morpholinopyridine-3-sulfonamide;

N-(2-(4-((4-cyclobutylpiperazin-1-yl)methyl)-2-fluorophenyl)pyridin-4-yl)-2-methoxy-5-morpholinopyridine-3-sulfonamide;

N-(2-(2,5-difluoro-4-((4-isopropylpiperazin-1-yl)methyl)phenyl)pyridin-4-yl)-2-methoxy-5-morpholinopyridine-3-sulfonamide;

N-(2-(2-fluoro-4-((4-(2-methoxyethyl)piperazin-1-yl)methyl)phenyl)pyridin-4-yl)-2-methoxy-5-morpholinopyridine-3-sulfonamide;

N-(2-(2-fluoro-4-((3-methylpyrrolidin-1-yl)methyl)phenyl)pyridin-4-yl)-2-methoxy-5-morpholinopyridine-3-sulfonamide;

N-(2-(2-fluoro-4-((2-methylpyrrolidin-1-yl)methyl)phenyl)pyridin-4-yl)-2-methoxy-5-morpholinopyridine-3-sulfonamide;

N-(2-(2-fluoro-4-(piperidin-1-ylmethyl)phenyl)pyridin-4-yl)-2-methoxy-5-morpholinopyridine-3-sulfonamide;

N-(2-(2-fluoro-4-((4-(2-hydroxypropan-2-yl)piperidin-1-yl)methyl)phenyl)pyridin-4-yl)-2-methoxy-5-morpholinopyridine-3-sulfonamide;

N-(2-(4-(((cis)-2,6-dimethylmorpholino)methyl)phenyl)pyridin-4-yl)-2-methoxy-5-morpholinopyridine-3-sulfonamide;

2-methoxy-5-morpholino-N-(2-(4-(morpholinomethyl)phenyl)pyridin-4-yl)pyridine-3-sulfonamide;

N-(2-(2-fluoro-4-(piperazin-1-ylmethyl)phenyl)pyridin-4-yl)-2-methoxy-5-morpholinopyridine-3-sulfonamide;

2-(dimethylamino)-N-(2-(2-fluoro-4-((4-isopropylpiperazin-1-yl)methyl)phenyl)pyridin-4-yl)-5-morpholinopyridine-3-sulfonamide;

N-(2-(4-((4-(tert-butyl)piperazin-1-yl)methyl)-2-fluorophenyl)pyridin-4-yl)-2-(dimethylamino)-5-morpholinopyridine-3-sulfonamide;

N-(2-(4-((4-(tert-butyl)piperazin-1-yl)methyl)-2-fluorophenyl)pyridin-4-yl)-2-methoxy-N-methyl-5-morpholinopyridine-3-sulfonamide;

N-(2-(2-fluoro-4-((4-isopropylpiperazin-1-yl)methyl)phenyl)pyridin-4-yl)-2-methoxy-N-methyl-5-morpholinopyridine-3-sulfonamide;

N-ethyl-N-(2-(2-fluoro-4-((4-isopropylpiperazin-1-yl)methyl)phenyl)pyridin-4-yl)-2-methoxy-5-morpholinopyridine-3-sulfonamide;

N-(2-(2-fluoro-4-((4-isopropylpiperazin-1-yl)methyl)phenyl)pyridin-4-yl)-2-methoxy-5-morpholino-N-propylpyridine-3-sulfonamide;

N-(2-(2-fluoro-4-((4-isopropylpiperazin-1-yl)methyl)phenyl)pyridin-4-yl)-N-isopropyl-2-methoxy-5-morpholinopyridine-3-sulfonamide;

ethyl 2-(N-(2-(2-fluoro-4-((4-isopropylpiperazin-1-yl)methyl)phenyl)pyridin-4-yl)-2-methoxy-5-morpholinopyridine-3-sulfonamido)acetate;

(N-(2-(2-fluoro-4-((4-isopropylpiperazin-1-yl)methyl)phenyl)pyridin-4-yl)-2-methoxy-5-morpholinopyridine-3-sulfonamido)methyl pivalate; or N-(2-(5-chloro-2-fluoro-4-((4-isopropylpiperazin-1-yl)methyl)phenyl)pyridin-4-yl)-2-methoxy-5-morpholinopyridine-3-sulfonamide;

N-(2-(4-(((2S,6R)-2,6-dimethylmorpholino)methyl)-2-fluorophenyl)pyridin-4-yl)-2-methoxy-5-morpholinopyridine-3-sulfonamide;

N-(2-(4-(((2S,6R)-2,6-dimethylmorpholino)methyl)-2-fluorophenyl)pyridin-4-yl)-2-ethoxy-5-morpholinopyridine-3-sulfonamide;

or a salt thereof.

In another embodiment, the compound of the invention is:

N-(2-(2-fluoro-4-((4-isopropylpiperazin-1-yl)methyl)phenyl)pyridin-4-yl)-2-methoxy-5-morpholinopyridine-3-sulfonamide;

N-(2-(4-((4-(tert-butyl)piperazin-1-yl)methyl)-2-fluorophenyl)pyridin-4-yl)-2-methoxy-5-morpholinopyridine-3-sulfonamide;

N-(2-(4-((4-isopropylpiperazin-1-yl)methyl)phenyl)pyridin-4-yl)-2-methoxy-5-morpholinopyridine-3-sulfonamide;

N-(2-(4-((dimethylamino)methyl)phenyl)pyridin-4-yl)-2-methoxy-5-morpholinopyridine-3-sulfonamide;

N-(2-(3-fluoro-4-((4-isopropylpiperazin-1-yl)methyl)phenyl)pyridin-4-yl)-2-methoxy-5-morpholinopyridine-3-sulfonamide;

N-(2-(4-((4-(tert-butyl)piperazin-1-yl)methyl)phenyl)pyridin-4-yl)-2-methoxy-5-morpholinopyridine-3-sulfonamide;

N-(2-(4-((4-cyclobutylpiperazin-1-yl)methyl)phenyl)pyridin-4-yl)-2-methoxy-5-morpholinopyridine-3-sulfonamide;

N-(2-(2,6-difluoro-4-((4-isopropylpiperazin-1-yl)methyl)phenyl)pyridin-4-yl)-2-methoxy-5-morpholinopyridine-3-sulfonamide;

N-(2-(4-((4-(sec-butyl)piperazin-1-yl)methyl)phenyl)pyridin-4-yl)-2-methoxy-5-morpholinopyridine-3-sulfonamide;

N-(2-(2-fluoro-4-(pyrrolidin-1-ylmethyl)phenyl)pyridin-4-yl)-2-methoxy-5-morpholinopyridine-3-sulfonamide;

N-(2-(3-fluoro-4-(pyrrolidin-1-ylmethyl)phenyl)pyridin-4-yl)-2-methoxy-5-morpholinopyridine-3-sulfonamide;

N-(2-(3,5-difluoro-4-((4-isopropylpiperazin-1-yl)methyl)phenyl)pyridin-4-yl)-2-methoxy-5-morpholinopyridine-3-sulfonamide;

2-methoxy-5-morpholino-N-(2-(4-((4-(oxetan-3-yl)piperazin-1-yl)methyl)phenyl)pyridin-4-yl)pyridine-3-sulfonamide;

N-(2-(2,3-difluoro-4-((4-isopropylpiperazin-1-yl)methyl)phenyl)pyridin-4-yl)-2-methoxy-5-morpholinopyridine-3-sulfonamide;

N-(2-(2-fluoro-4-((4-(oxetan-3-yl)piperazin-1-yl)methyl)phenyl)pyridin-4-yl)-2-methoxy-5-morpholinopyridine-3-sulfonamide;

N-(2-(4-((4-cyclobutylpiperazin-1-yl)methyl)-2-fluorophenyl)pyridin-4-yl)-2-methoxy-5-morpholinopyridine-3-sulfonamide;

N-(2-(2,5-difluoro-4-((4-isopropylpiperazin-1-yl)methyl)phenyl)pyridin-4-yl)-2-methoxy-5-morpholinopyridine-3-sulfonamide;

N-(2-(2-fluoro-4-((4-(2-methoxyethyl)piperazin-1-yl)methyl)phenyl)pyridin-4-yl)-2-methoxy-5-morpholinopyridine-3-sulfonamide;

N-(2-(2-fluoro-4-((3-methylpyrrolidin-1-yl)methyl)phenyl)pyridin-4-yl)-2-methoxy-5-morpholinopyridine-3-sulfonamide;

N-(2-(2-fluoro-4-((2-methylpyrrolidin-1-yl)methyl)phenyl)pyridin-4-yl)-2-methoxy-5-morpholinopyridine-3-sulfonamide;

N-(2-(2-fluoro-4-(piperidin-1-ylmethyl)phenyl)pyridin-4-yl)-2-methoxy-5-morpholinopyridine-3-sulfonamide;

N-(2-(2-fluoro-4-((4-(2-hydroxypropan-2-yl)piperidin-1-yl)methyl)phenyl)pyridin-4-yl)-2-methoxy-5-morpholinopyridine-3-sulfonamide;

N-(2-(4-(((cis)-2,6-dimethylmorpholino)methyl)phenyl)pyridin-4-yl)-2-methoxy-5-morpholinopyridine-3-sulfonamide;

2-methoxy-5-morpholino-N-(2-(4-(morpholinomethyl)phenyl)pyridin-4-yl)pyridine-3-sulfonamide;

N-(2-(2-fluoro-4-(piperazin-1-ylmethyl)phenyl)pyridin-4-yl)-2-methoxy-5-morpholinopyridine-3-sulfonamide;

2-(dimethylamino)-N-(2-(2-fluoro-4-((4-isopropylpiperazin-1-yl)methyl)phenyl)pyridin-4-yl)-5-morpholinopyridine-3-sulfonamide;

N-(2-(4-((4-(tert-butyl)piperazin-1-yl)methyl)-2-fluorophenyl)pyridin-4-yl)-2-(dimethylamino)-5-morpholinopyridine-3-sulfonamide;

N-(2-(4-((4-(tert-butyl)piperazin-1-yl)methyl)-2-fluorophenyl)pyridin-4-yl)-2-methoxy-N-methyl-5-morpholinopyridine-3-sulfonamide;

N-(2-(2-fluoro-4-((4-isopropylpiperazin-1-yl)methyl)phenyl)pyridin-4-yl)-2-methoxy-N-methyl-5-morpholinopyridine-3-sulfonamide;

N-ethyl-N-(2-(2-fluoro-4-((4-isopropylpiperazin-1-yl)methyl)phenyl)pyridin-4-yl)-2-methoxy-5-morpholinopyridine-3-sulfonamide;

N-(2-(2-fluoro-4-((4-isopropylpiperazin-1-yl)methyl)phenyl)pyridin-4-yl)-2-methoxy-5-morpholino-N-propylpyridine-3-sulfonamide;

N-(2-(2-fluoro-4-((4-isopropylpiperazin-1-yl)methyl)phenyl)pyridin-4-yl)-N-isopropyl-2-methoxy-5-morpholinopyridine-3-sulfonamide;

ethyl 2-(N-(2-(2-fluoro-4-((4-isopropylpiperazin-1-yl)methyl)phenyl)pyridin-4-yl)-2-methoxy-5-morpholinopyridine-3-sulfonamido)acetate;

(N-(2-(2-fluoro-4-((4-isopropylpiperazin-1-yl)methyl)phenyl)pyridin-4-yl)-2-methoxy-5-morpholinopyridine-3-sulfonamido)methyl pivalate; or N-(2-(5-chloro-2-fluoro-4-((4-isopropylpiperazin-1-yl)methyl)phenyl)pyridin-4-yl)-2-methoxy-5-morpholinopyridine-3-sulfonamide;

or a salt thereof.

In another embodiment, the compound of the invention is:

N-(2-(2-fluoro-4-((4-isopropylpiperazin-1-yl)methyl)phenyl)pyridin-4-yl)-2-methoxy-5-morpholinopyridine-3-sulfonamide;

or a salt thereof.

In a further embodiment, the compound of the invention is:

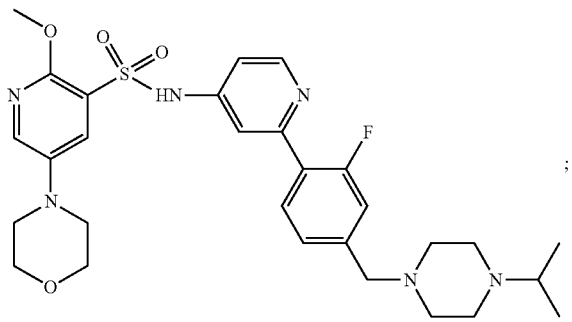 [SMILES: COc1ncc(N2CCOCC2)cc1S(=O)(=O)Nc1ccnc(-c2ccc(CN3CCN(C(C)C)CC3)cc2F)c1]

or a salt thereof.

Terms and Definitions

"Alkyl" refers to a saturated hydrocarbon chain having the specified number of member atoms. For example, $C_{1-6}$alkyl refers to an alkyl group having from 1 to 6 member atoms, for example from 1 to 4 member atoms. Alkyl groups may be straight or branched. Representative branched alkyl groups have one, two, or three branches. Alkyl groups may be optionally substituted with one or more substituents as defined herein. Alkyl includes methyl, ethyl, propyl (n-propyl and isopropyl), butyl (n-butyl, isobutyl, and t-butyl), pentyl (n-pentyl, isopentyl, and neopentyl), and hexyl. Alkyl groups may also be part of other groups, for example $C_{1-6}$alkoxy.

"Cycloalkyl" refers to a saturated hydrocarbon ring having the specified number of member atoms. Cycloalkyl groups are monocyclic ring systems. For example, $C_{3-6}$cycloalkyl refers to a cycloalkyl group having from 3 to 6 member atoms. Cycloalkyl includes cyclopropyl, cyclobutyl, cyclopentyl, and cyclohexyl. In one embodiment, the cycloalkyl groups herein are cyclobutyl.

"Enantiomerically enriched" refers to products whose enantiomeric excess is greater than zero. For example, enantiomerically enriched refers to products whose enantiomeric excess is greater than 50% ee, greater than 75% ee, and greater than 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" (or "half-lives") refers to the time required for half of a quantity of a substance to be converted to another chemically distinct species in vitro or in vivo.

"Halogen" refers to the halogen radical fluoro, choro, bromo or iodo.

"Heteroatom" refers to a nitrogen or oxygen atom.

"Heterocyclyl", unless otherwise defined, refers to a saturated ring having the specified number of member atoms and containing 1 or 2 heteroatoms as member atoms in the ring. Heterocyclyl groups may be optionally substituted with one or more substituents as defined herein. The heterocyclyl groups herein are monocyclic ring systems having 4-, 5- or 6-member atoms. Monocyclic heterocyclyl includes oxetanyl, pyrrolidinyl, piperidinyl, piperazinyl and morpholinyl. In one embodiment, the heterocycle is piperazinyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group may be unsubstituted or substituted with one or more substituents as defined herein.

"Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, salts, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein the symbols and conventions used in these processes, schemes and examples are consistent with those used in the contemporary scientific literature, for example, the *Journal of the American Chemical Societyor the Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

Ac: Acetate
Boc: tert-Butyloxycarbonyl
BrettPhos: 2-(Dicyclohexylphosphino)3,6-dimethoxy-2',4',6'-triisopropyl-1,1'-biphenyl
EtOAc: Ethyl acetate
DavePhos: 2'-(Dicyclohexylphosphino)-N,N-dimethyl-[1,1'-biphenyl]-2-amine
DCM: Dichloromethane
DIPEA: N—N-Diisopropylethylamine
DMAP: 4-Dimethylaminopyridine
DMF: N,N-Dimethylformamide
DMSO: Dimethylsulfoxide
EDTA: Ethylenediaminetetraacetic acid
EtOH: Ethanol
h: Hour(s)
HPLC: High performance liquid chromatography
id: Internal diameter
IPA: Isopropanol
JohnPhos: 2-Biphenyl)di-tert-butylphosphine
LCMS: Liquid chromatography mass spectroscopy
μL: Microliter(s)
min: Minute(s)

mL: Millilitre(s)
mmol: Millimole(s)
M: Molar
Me: Methyl
MeCN: Acetonitrile
MeOH: Methanol
MS: Mass Spectra
NMR: Nuclear magnetic resonance
$PdCl_2$(dppf): [1,1'-Bis(diphenylphosphino)ferrocene]dichloropalladium(II)
$Pd(dba)_2$: bis(Dibenzylideneacetone)palladium(0)
$Pd_2(dba)_3$: Tris(dibenzylideneacetone)dipalladium(0)
$Pd(OAc)_2$: Palladium(II) acetate
Rt: Retention time
RuPhos: 2-Dicyclohexylphosphino-2',6'-diisopropoxybiphenyl
s: Second(s)
SPE: Solid phase extraction
TFA: Trifluoroacetic acid
THF: Tetrahydrofuran
UPLC: Ultra performance liquid chromatography
UV: Ultraviolet
v/v: By volume
w/w: By weight
Xantphos: 4,5-Bis(diphenylphosphino)-9,9-dimethylxanthene
XPhos palladacycle: (2-Dicyclohexylphosphino-2',4',6'-thisopropyl-1,1'-biphenyl)[2-(2-aminoethyl)phenyl)]palladium(II) chloride
Xphos pre-catalyst $2^{nd}$ generation: Chloro(2-dicyclohexylphosphino-2',4',6'-tri isopropyl-1,1'-biphenyl)[2-(2'-amino-1,1'-biphenyl)]palladium(II)

Included within the scope of the "compounds of the invention" are all polymorphs, radiolabelled derivatives, stereoisomers and optical isomers of the compounds of formula (I) and salts thereof.

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. The compounds of the invention may exist in solvated and unsolvated form. Solvates may involve nonaqueous solvents such as ethanol, isopropanol, DMSO, acetic acid, ethanolamine, and EtOAc, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs". The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification.

The skilled artisan will appreciate that different polymorphs may be produced, for example, by changing or adjusting the reaction conditions or reagents, used in making the compound.

For example, changes in temperature, pressure, or solvent may result in polymorphs. In addition, one polymorph may spontaneously convert to another polymorph under certain conditions.

In one aspect, the present invention provides N-(2-(2-fluoro-4-((4-isopropylpiperazin-1-yl)methyl)phenyl)pyridin-4-yl)-2-methoxy-5-morpholinopyridine-3-sulfonamide or a salt thereof in crystalline form.

In one embodiment, the present invention provides N-(2-(2-fluoro-4-((4-isopropylpiperazin-1-yl)methyl)phenyl)pyridin-4-yl)-2-methoxy-5-morpholinopyridine-3-sulfonamide in crystalline form.

In another embodiment, the present invention provides crystalline N-(2-(2-fluoro-4-((4-isopropylpiperazin-1-yl)methyl)phenyl)pyridin-4-yl)-2-methoxy-5-morpholinopyridne-3-sulfonamide characterised in that it provides an XRPD (X-ray powder diffraction) pattern having peaks (°2θ) at about 5.2, about 8.0, about 11.9 and/or about 13.2.

In another embodiment, the present invention provides crystalline N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide characterised in that it provides an XRPD pattern comprising peaks substantially as set out in Table 1.

In another embodiment, the present invention provides crystalline N-(2-(2-fluoro-4-((4-isopropylpiperazin-1-yl)methyl)phenyl)pyridin-4-yl)-2-methoxy-5-morpholinopyridine-3-sulfonamide characterised in that it provides an XRPD pattern substantially in accordance with FIG. 1.

In another embodiment, the present invention provides crystalline N-(2-(2-fluoro-4-((4-isopropylpiperazin-1-yl)methyl)phenyl)pyridin-4-yl)-2-methoxy-5-morpholinopyridine-3-sulfonamide characterised in that it provides an XRPD (X-ray powder diffraction) pattern having peaks (°9θ) at about 6.8, about 9.4, about 11.0 and/or about 11.7.

In another embodiment, the present invention provides crystalline N-[5-[4-(5-{[(2R,6s)-2,6-dimethyl-4-morpholinyl]methyl}-1,3-oxazol-2-yl)-1H-indazol-6-yl]-2-(methyloxy)-3-pyridinyl]methanesulfonamide characterised in that it provides an XRPD pattern comprising peaks substantially as set out in Table 2.

Figure 2:
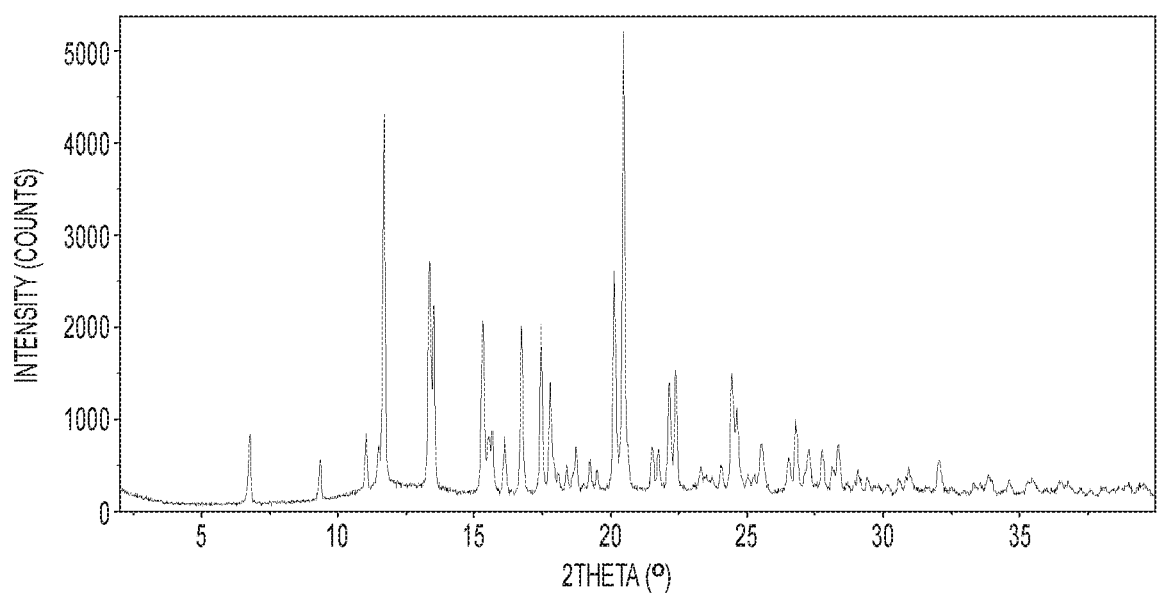
FIG. 2 shows an XRPD pattern for N-(2-(2-fluoro-4-((4-isopropylpiperazin-1-yl)methyl)phenyl)pyridin-4-yl)-2-methoxy-5-morpholinopyridine-3-sulfonamide (hydrate—Form 1).

In another embodiment, the present invention provides crystalline N-(2-(2-fluoro-4-((4-isopropylpiperazin-1-yl)methyl)phenyl)pyridin-4-yl)-2-methoxy-5-morpholinopyridine-3-sulfonamide characterised in that it provides an XRPD pattern substantially in accordance with FIG. 2.

In another embodiment, the present invention provides crystalline N-(2-(2-fluoro-4-((4-isopropylpiperazin-1-yl)methyl)phenyl)pyridin-4-yl)-2-methoxy-5-morpholinopyridine-3-sulfonamide characterised in that it provides an XRPD (X-ray powder diffraction) pattern having peaks (°2θ) at about 6.4, about 9.0, about 10.4 and/or about 11.6.

In another embodiment, the present invention provides crystalline N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide characterised in that it provides an XRPD pattern comprising peaks substantially as set out in Table 3.

Figure 3:
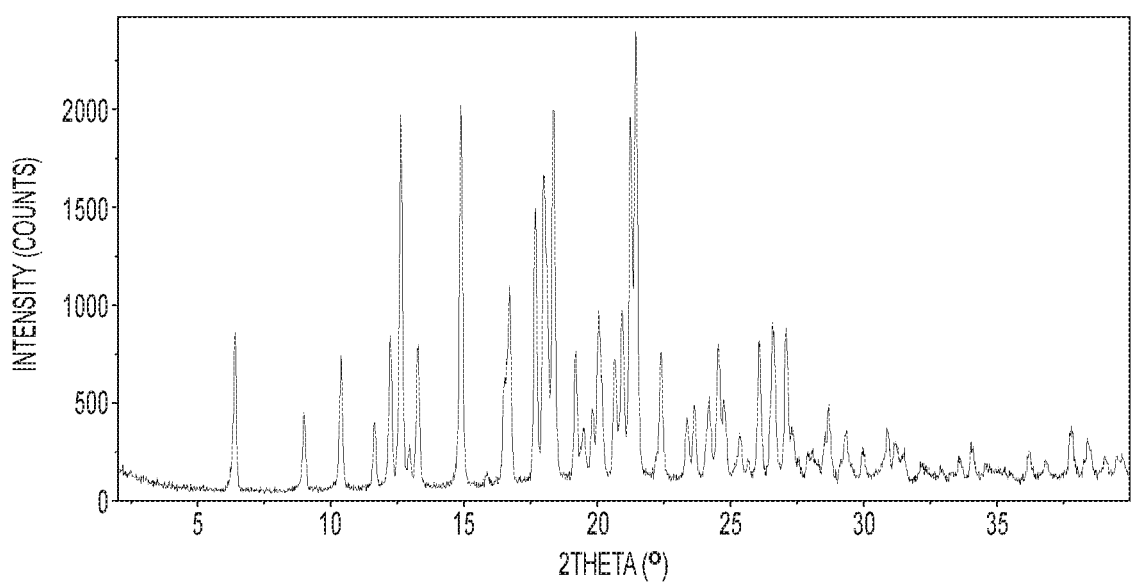
FIG. 3 shows an XRPD pattern for N-(2-(2-fluoro-4-((4-isopropylpiperazin-1-yl)methyl)phenyl)pyridin-4-yl)-2-methoxy-5-morpholinopyridine-3-sulfonamide (anhydrate—Form 2).

In another embodiment, the present invention provides crystalline N-(2-(2-fluoro-4-((4-isopropylpiperazin-1-yl)methyl)phenyl)pyridin-4-yl)-2-methoxy-5-morpholinopyridine-3-sulfonamide characterised in that it provides an XRPD pattern substantially in accordance with FIG. 3.

In another embodiment, the present invention provides crystalline N-(2-(2-fluoro-4-((4-isopropylpiperazin-1-yl) methyl)phenyl)pyridin-4-yl)-2-methoxy-5-morpholinopyridine-3-sulfonamide characterised in that it provides an XRPD (X-ray powder diffraction) pattern having peaks (°2θ) at about 8.1, about 9.1, about 10.2, about 11.7 and/or about 12.7.

In another embodiment, the present invention provides crystalline N-[5-[4-(5-{[(2R,6S)-2,6-dimethyl-4-morpholinyl]methyl}-1,3-oxazol-2-yl)-1H-indazol-6-yl]-2-(methyloxy)-3-pyridinyl]methanesulfonamide characterised in that it provides an XRPD pattern comprising peaks substantially as set out in Table 4.

Figure 4:
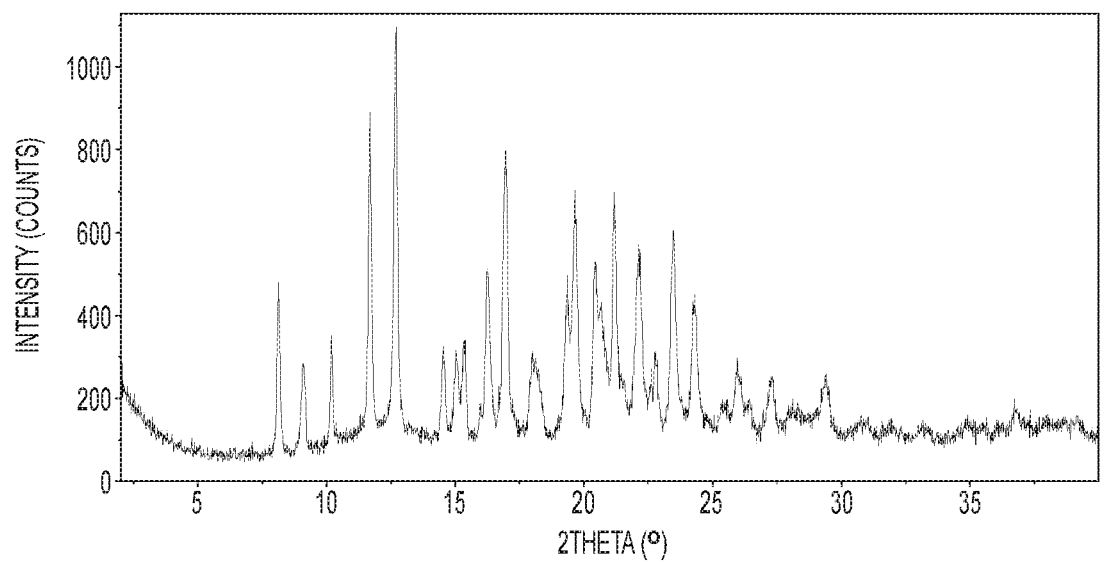
FIG. 4 shows an XRPD pattern for N-(2-(2-fluoro-4-((4-isopropylpiperazin-1-yl)methyl)phenyl)pyridin-4-yl)-2-methoxy-5-morpholinopyridine-3-sulfonamide (hydrate—Form 3).

In another embodiment, the present invention provides crystalline N-(2-(2-fluoro-4-((4-isopropylpiperazin-1-yl) methyl)phenyl)pyridin-4-yl)-2-methoxy-5-morpholinopyridine-3-sulfonamide characterised in that it provides an XRPD pattern substantially in accordance with FIG. 4.

When it is indicated herein that there is a peak in an XRPD pattern at a given value, it is typically meant that the peak is within ±0.2, for example ±0.1, of the value quoted.

The invention also includes isotopically-labelled compounds, which are identical to the compounds of the invention, but for the fact that one or more atoms are replaced by an atom having an atomic mass or mass number different from the atomic mass or mass number most commonly found in nature. Examples of isotopes that can be incorporated into the compounds of the invention include isotopes of hydrogen, carbon, nitrogen, oxygen and fluorine, such as $^{2}H$, $^{3}H$, $^{11}C$, $^{14}C$ and $^{18}F$.

The compounds of the invention may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in a compound of the invention, or in any chemical structure illustrated herein, is not specified the structure is intended to encompass any stereoisomer and all mixtures thereof. Thus, compounds of the invention containing one or more chiral center may be used as racemic mixtures, enantiomerically enriched mixtures, or as enantiomerically pure individual stereoisomers.

Individual stereoisomers of a compound of the invention which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral enviornment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds of the invention may also contain centers of geometric asymmetry. Where the stereochemistry of a center of geometric asymmetry present in a compound of the invention, or in any chemical structure illustrated herein, is not specified, the structure is intended to encompass the trans geometric isomer, the cis geometric isomer, and all mixtures thereof. Likewise, all tautomeric forms are also included whether such tautomers exist in equilibrium or predominately in one form.

It is to be understood that the references herein to compounds of formula (I) and salts thereof covers the compounds of formula (I) as free acids or free bases, or as salts thereof, for example as pharmaceutically acceptable salts thereof. Thus, in one embodiment, the invention is directed to a compound of formula (I) as the free acid or free base. In another embodiment, the invention is directed to a compound of formula (I) or a salt thereof. In a further embodiment, the invention is directed to a compound of formula (I) or a pharmaceutically acceptable salt thereof.

The skilled artisan will appreciate that pharmaceutically acceptable salts of the compounds according to formula (I) may be prepared. Indeed, in certain embodiments of the invention, pharmaceutically acceptable salts of the compounds according to formula (I) may be preferred over the respective free base or free acid because such salts may impart greater stability or solubility to the molecule thereby facilitating formulation into a dosage form.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form, or a non-pharmaceutically acceptable salt, with a suitable base or acid, respectively.

Salts and solvates having non-pharmaceutically acceptable counter-ions or associated solvents are within the scope of the present invention, for example, for use as intermediates in the preparation of other compounds of formula (I) and their pharmaceutically acceptable salts. Thus one embodiment of the invention embraces compounds of formula (I) and salts thereof.

In certain embodiments, compounds according to formula (I) may contain an acidic functional group. Suitable pharmaceutically-acceptable salts include salts of such acidic functional groups. Representative salts include pharmaceutically acceptable metal salts such as sodium, potassium, lithium, calcium, magnesium, aluminum, and zinc salts; carbonates and bicarbonates of a pharmaceutically acceptable metal cation such as sodium, potassium, lithium, calcium, magnesium, aluminum, and zinc; pharmaceutically acceptable organic primary, secondary, and tertiary amines including aliphatic amines, aromatic amines, aliphatic diamines, and hydroxy alkylamines such as methylamine, ethylamine, 2-hydroxyethylamine, diethylamine, TEA, ethylenediamine, ethanolamine, diethanolamine, and cyclohexylamine.

In certain embodiments, compounds according to formula (I) may contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate.

Compound Preparation

The compounds of the invention may be made by a variety of methods, including standard chemistry. Any previously defined variable will continue to have the previously defined meaning unless otherwise indicated. Illustrative general synthetic methods are set out below and then specific compounds of the invention are prepared in the Examples section.

Process A

Compounds of formula (I) and salts thereof may be prepared by reacting a compound of formula (II) or a salt thereof

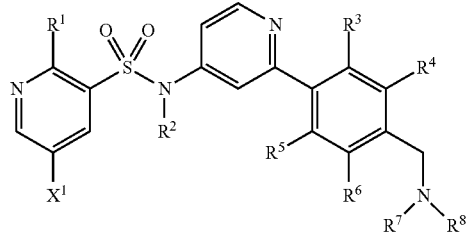

(II)

wherein $R^2$ to $R^8$ are as defined above and $X^1$ is halogen, for example chloro or bromo, with morpholine in the presence of a suitable catalyst.

The catalyst used in the formation of the compound of formula (I) is typically a palladium catalyst complex, for example a palladium complex with a suitable ligand. The ligand may be, for example, a Buchwald ligand such as RuPhos (2-dicyclohexylphosphino-2',6'-diisopropoxybiphenyl) or DavePhos (2'-(dicyclohexylphosphino)-N,N-dimethyl-[1,1'-biphenyl]-2-amine). In one embodiment, the palladium catalyst is a palladium complex with RuPhos.

The compound of formula (II) or salt thereof may be prepared by reacting a compound of formula (III) or a salt thereof

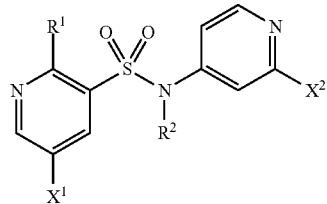

(III)

wherein $R^1$, $R^2$ and $X^1$ are as defined above and $X^2$ is halogen, for example bromo, with a boronic acid or ester of formula (IVa) or formula (IVb)

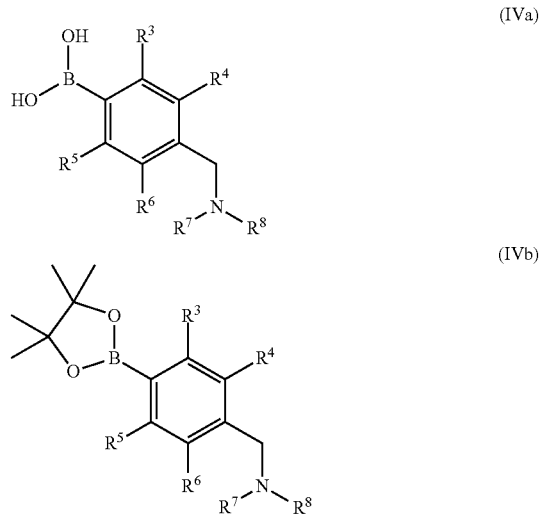

wherein $R^3$ to $R^8$ are as defined above, in the presence of a suitable catalyst.

The catalyst used in the formation of the compound of formula (II) is typically a palladium catalyst complex, for example [1,1'-bis(diphenylphosphino)ferrocene]dichloropalladium(II) or BrettPhos.

Examples of suitable processes for the preparation of compounds of formulae (IVa) and (IVb) are summarised in Scheme 1 below.

Scheme 1

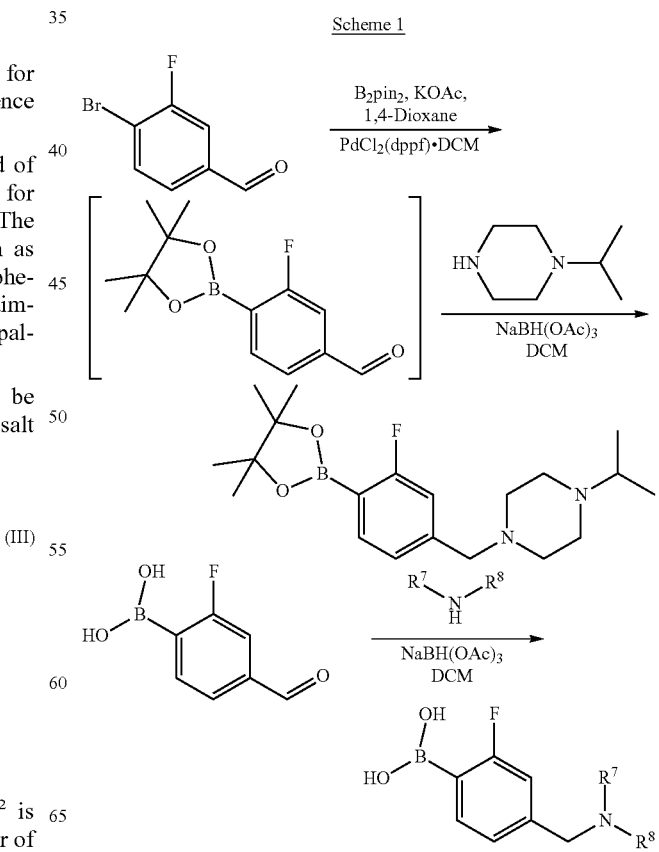

-continued
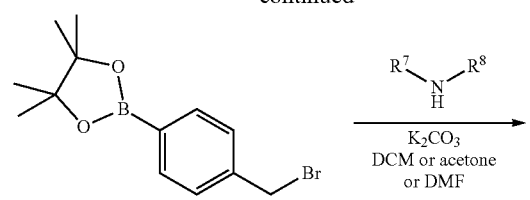
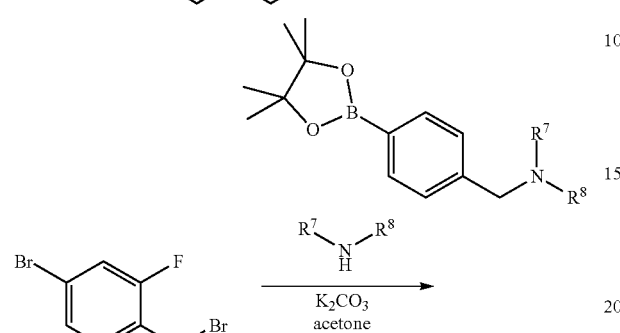
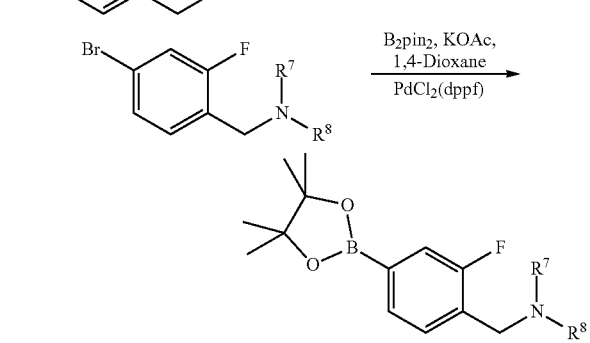
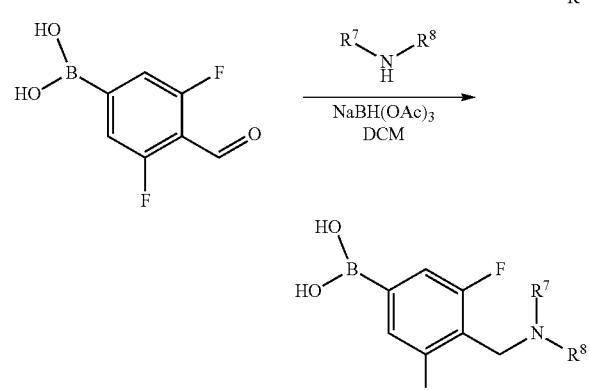
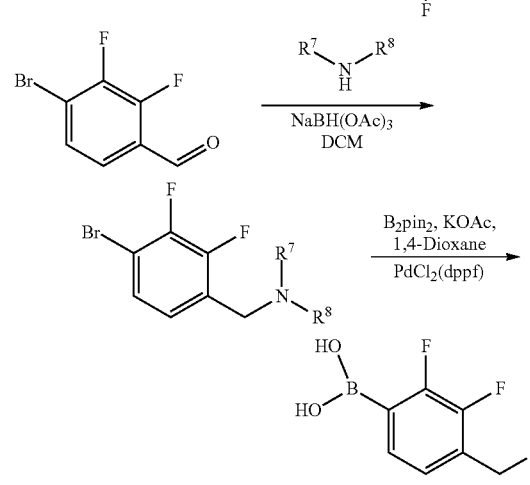
-continued
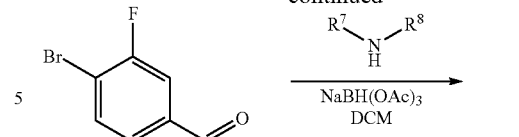
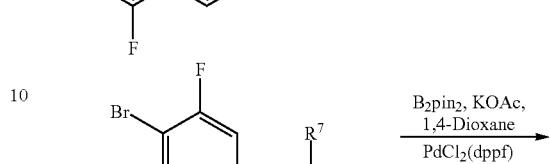
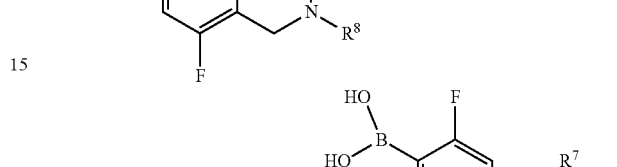
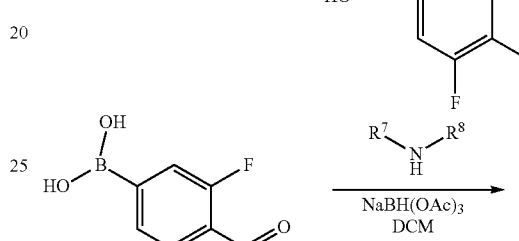
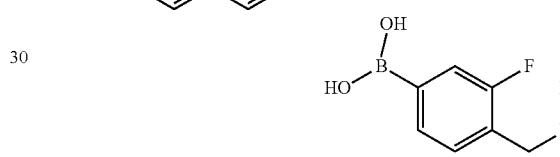
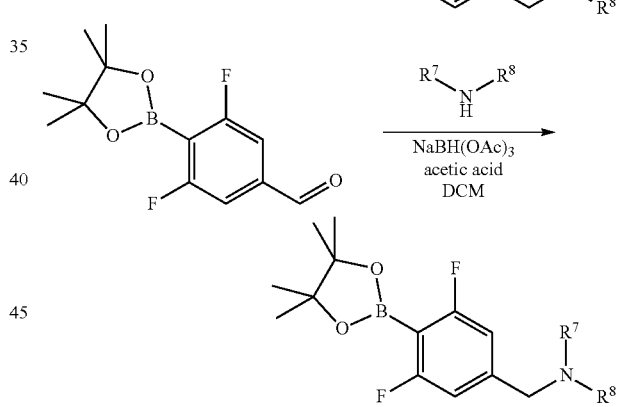
Alternatively, the compound of formula (II) or salt thereof may be prepared by reacting a compound of formula (V) or a salt thereof
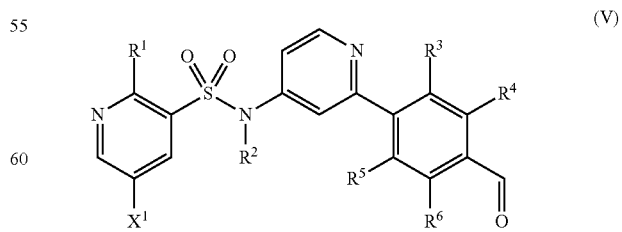
(V)
wherein $R^1$ to $R^6$ and $X^1$ are as defined above, with a compound of formula (VI)
$$HNR^7R^8 \qquad\qquad (VI)$$

wherein $R^7$ and $R^8$ are as defined above, in the presence of a reducing agent.

Compounds of formula (V) and salts thereof may be prepared by reacting a compound of formula (III) as defined above with a boronic acid or ester of formulae (VIIa) or (VIIb)

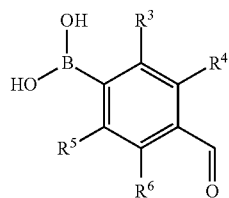
(VIIa)

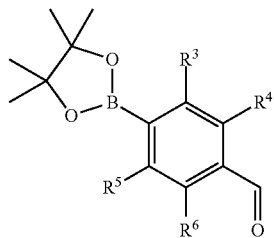
(VIIb)

wherein $R^3$ to $R^8$ are as defined above, in the presence of a suitable catalyst.

The catalyst used in the formation of the compound of formula (V) is typically a palladium catalyst complex, for example 2'-(dimethylamino)-2-biphenylyl-palladium(II) chloride dinorbornylphosphine complex or Xphos pre-catalyst $2^{nd}$ generation.

Examples of process A are depicted in Schemes 2 to 7 below.

Scheme 2
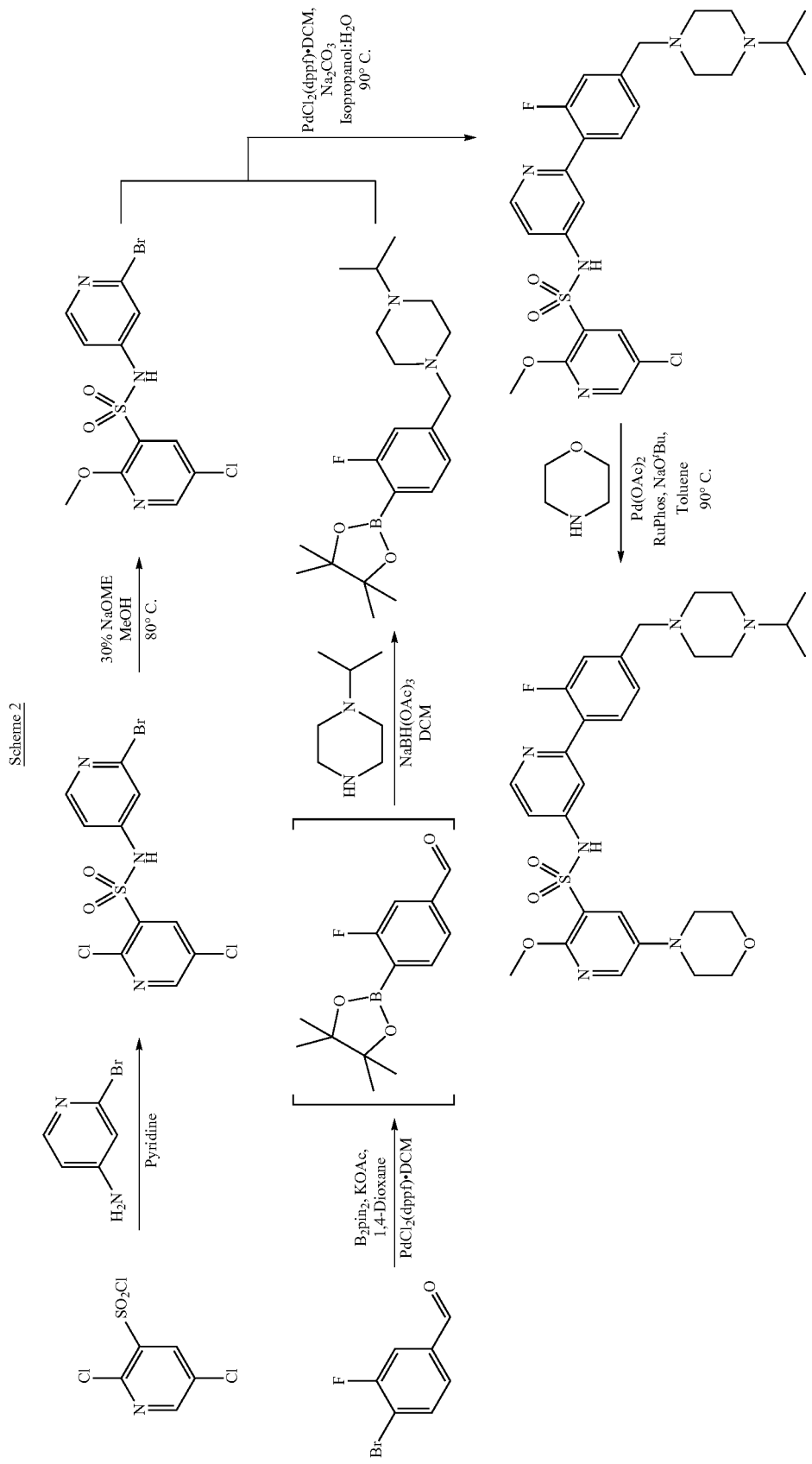

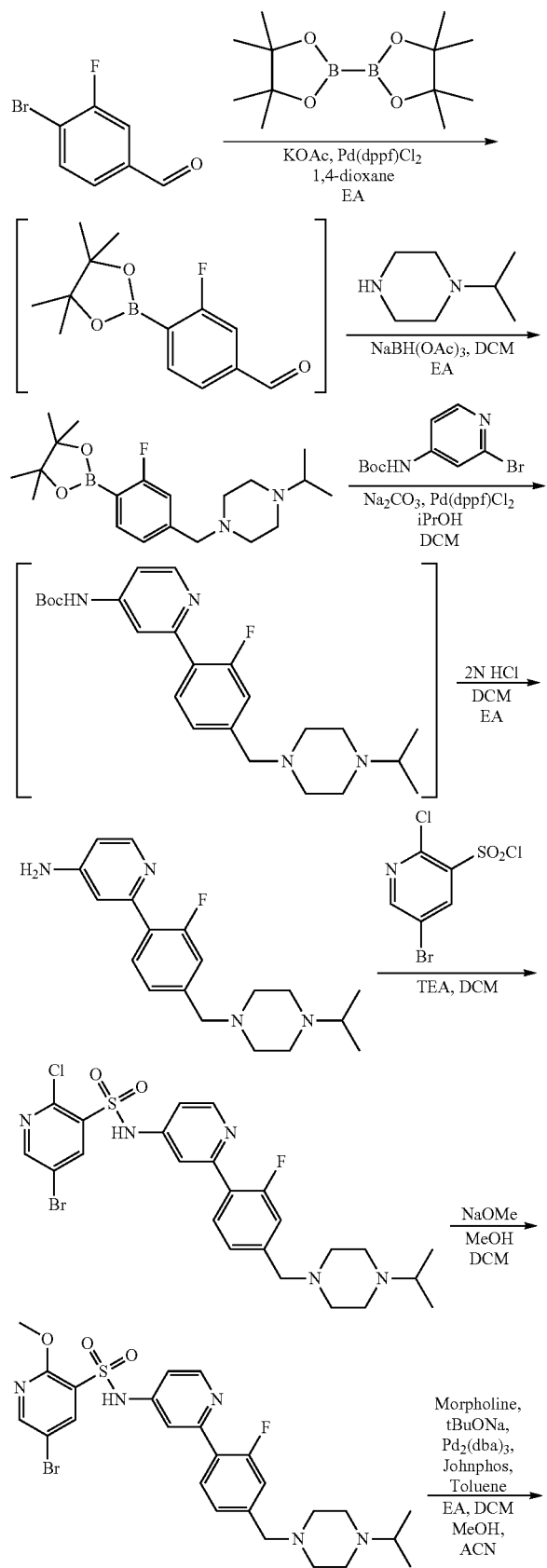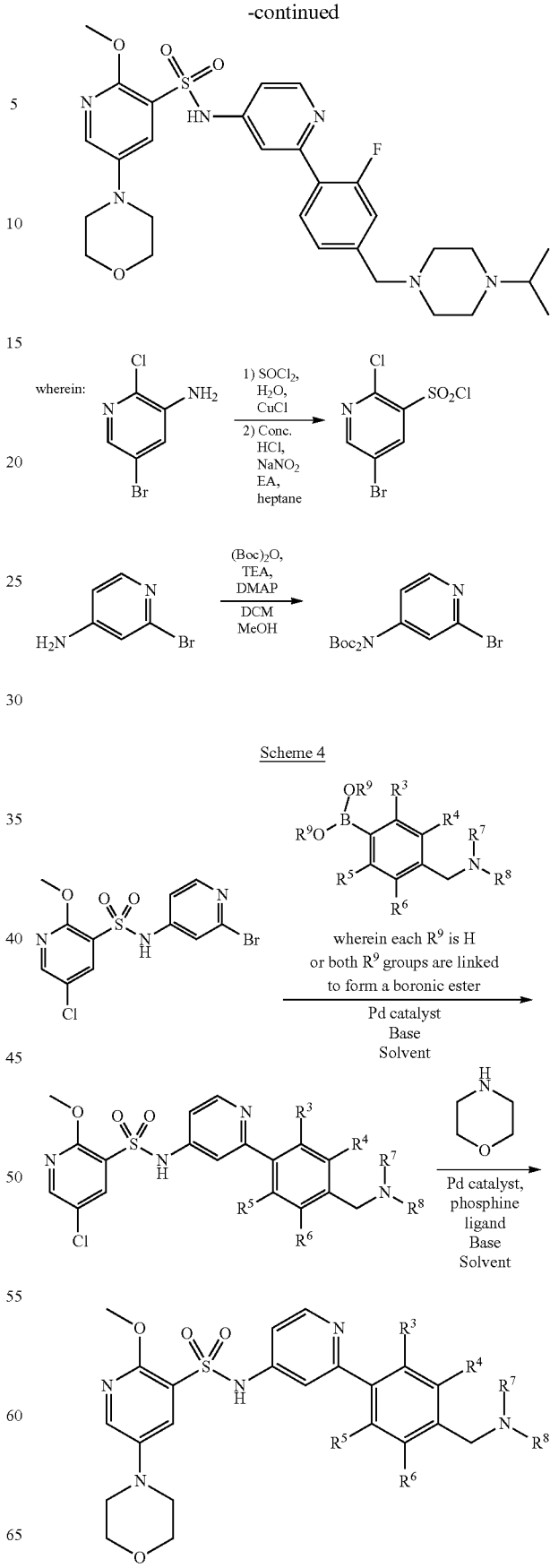

31
Scheme 5
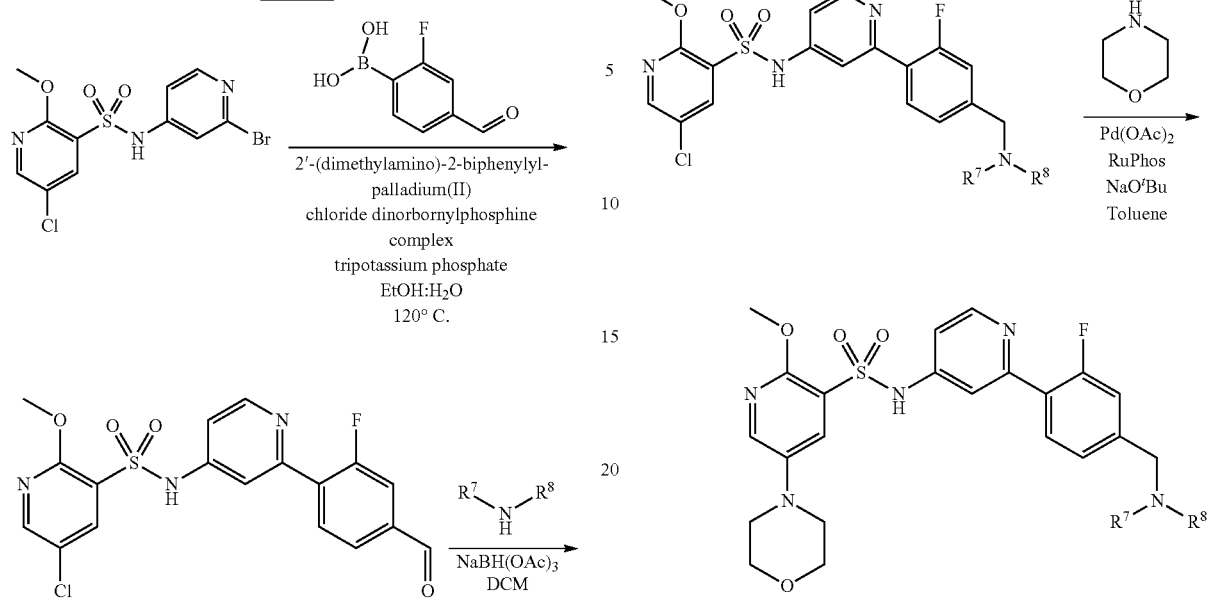
32
-continued
Scheme 6
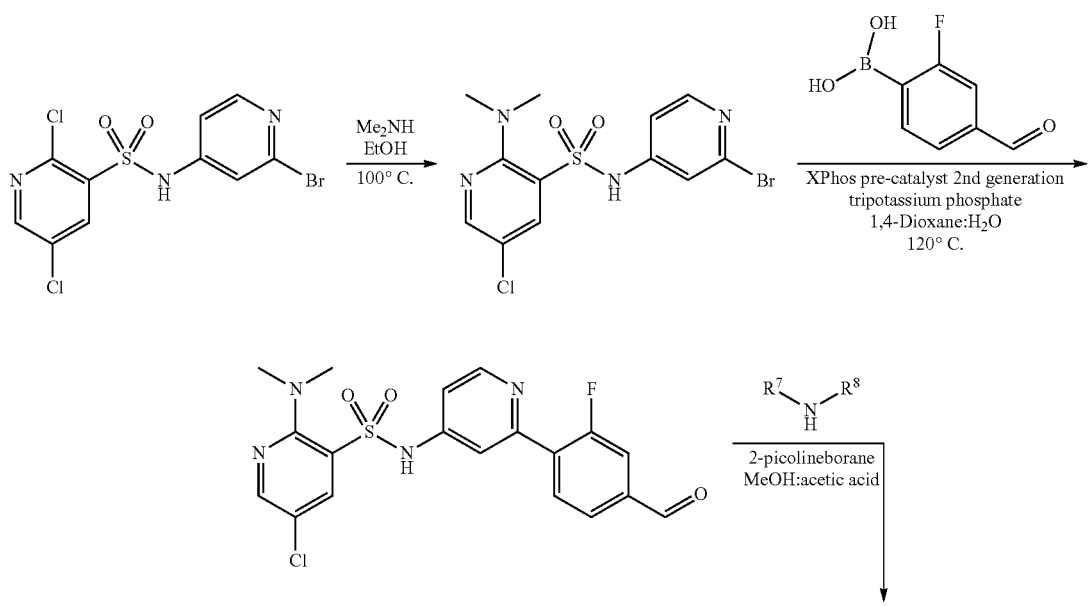
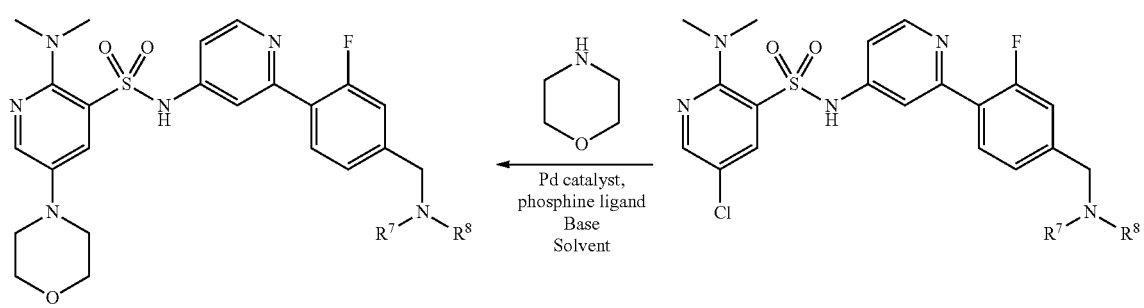

Scheme 7

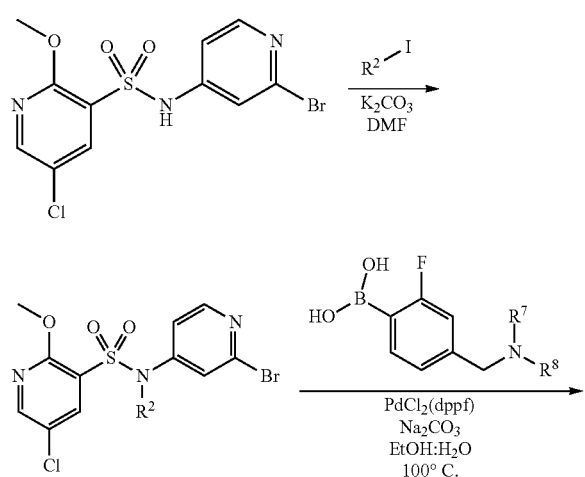

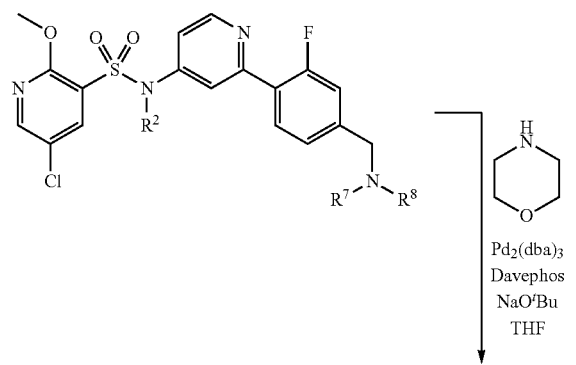

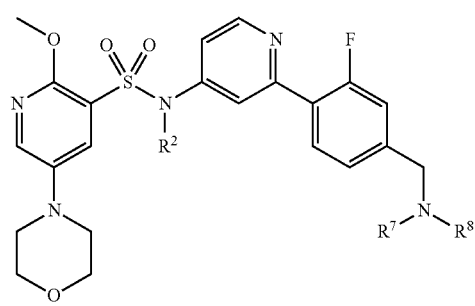

Process B

Compounds of formula (I) and salts thereof may also be prepared by reacting a compound of formula (VIII) or a salt thereof

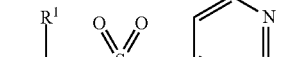

wherein $R^1$ to $R^6$ are as defined above, with a compound of formula (VI) as defined above, in the presence of a reducing agent.

Compounds of formula (VIII) and salts thereof may be prepared by reacting a compound of formula (IX)

(IX)

wherein $R^1$ to $R^6$ are as defined above and $X^3$ is halogen, for example chloro, with a boronic acid or ester of formula (VIIa) or (VIIb) as defined above, in the presence of a suitable catalyst.

The catalyst used in the formation of the compound of formula (IX) is typically a palladium catalyst complex, for example XPhos palladacycle.

Compounds of formula (IX) and salts thereof may be prepared by reacting a compound of formula (III) or a salt thereof as defined above with morpholine.

An example of process B is depicted in Scheme 8 below.

Scheme 8

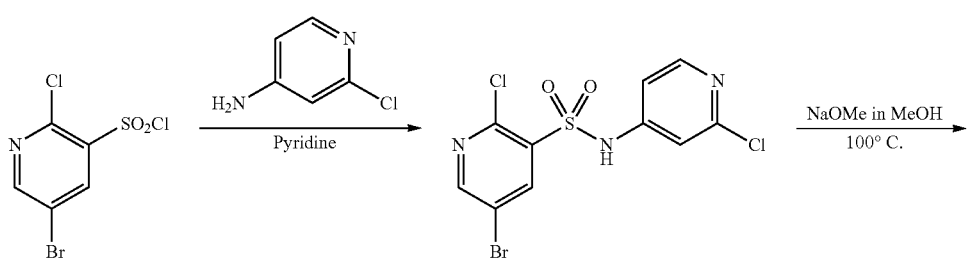

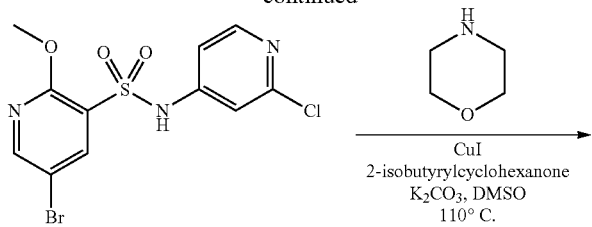

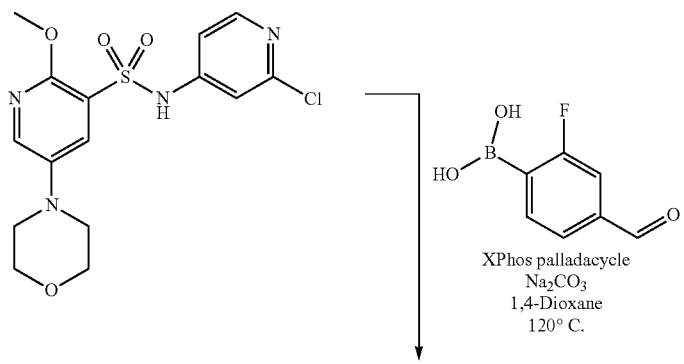

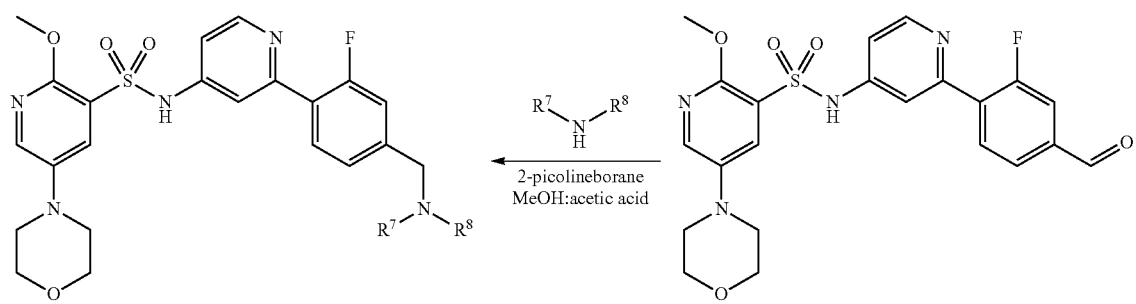

Process C

Compounds of formula (I) and salts thereof may also be prepared by reacting a compound of formula (X) or a salt thereof (X)

wherein $R^1$ and $R^3$ to $R^8$ are as defined above, with a compound of formula (XI)

$$R^2—X^4 \qquad (XI)$$

wherein $R^2$ is $C_{1-6}$alkyl optionally substituted by —C(O)O$C_{1-6}$alkyl or —OC(O)$C_{1-6}$alkyl and $X^4$ is halogen, for example iodo.

An example of process C is depicted in Scheme 9 below.

Scheme 9

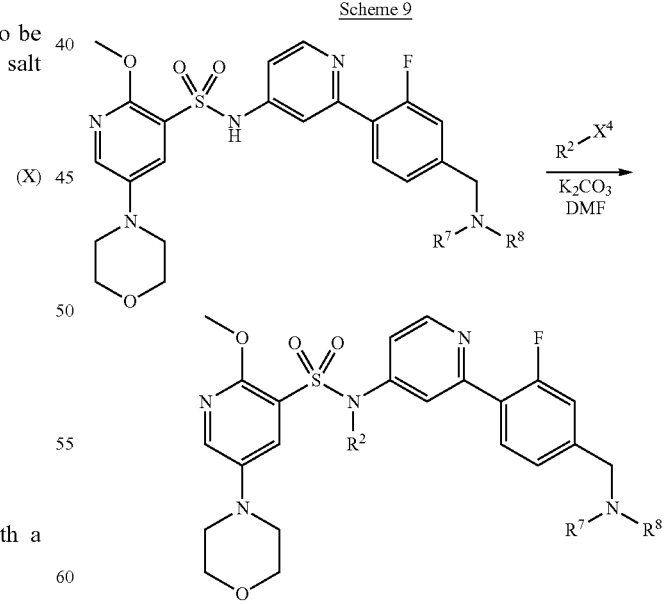

Process D

As the skilled person will appreciate, the processes for preparing the compounds of formula (I) and salts thereof may employ a suitable protecting group(s). Accordingly, the final step in the process may involve the removal of such protecting group(s).

An example of process D is depicted in Scheme 10 below.
Scheme 10
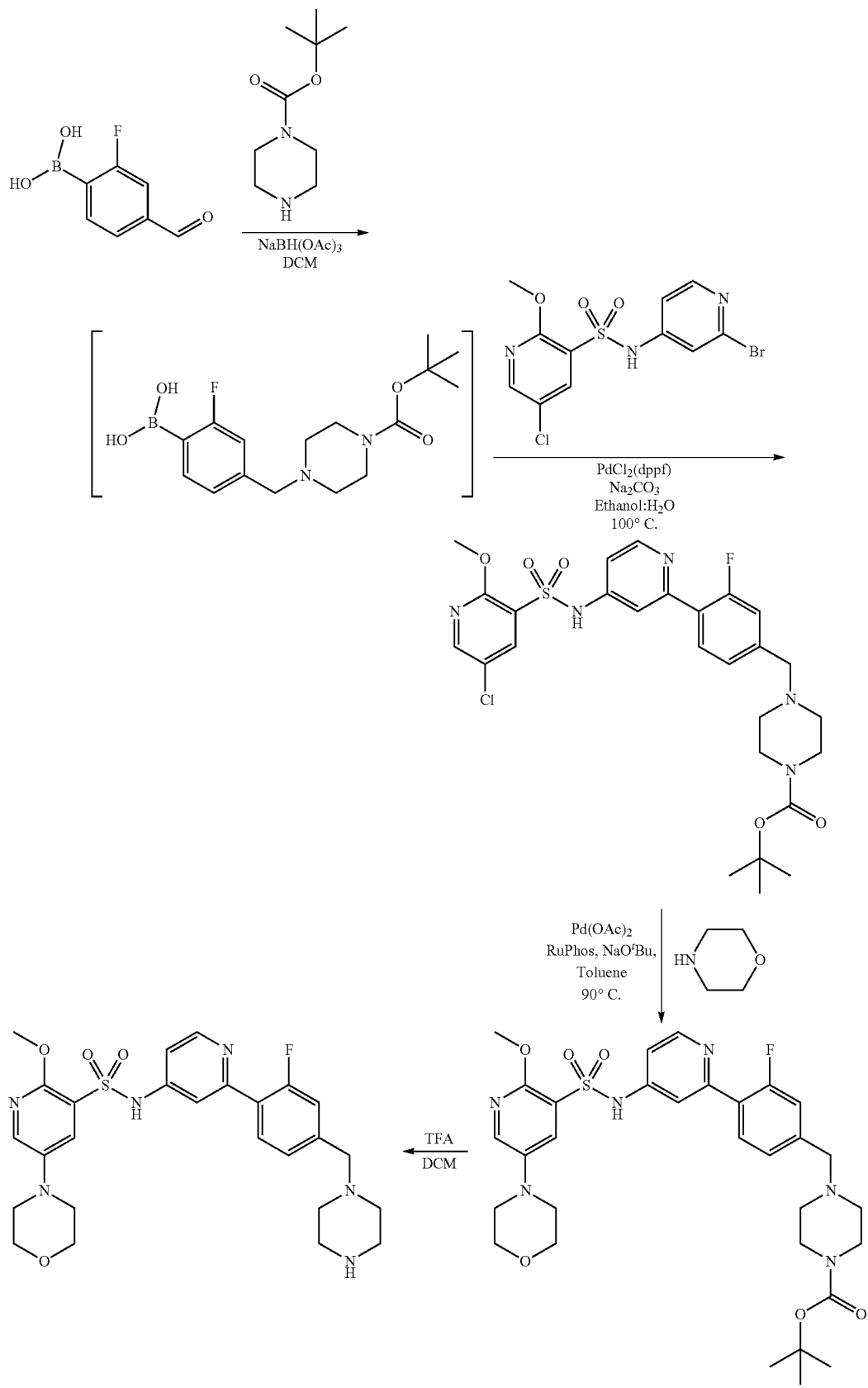

Thus, in one embodiment the invention provides a process for preparing a compound of formula (I) or a salt thereof comprising:

a) reacting a compound of formula (II) or a salt thereof

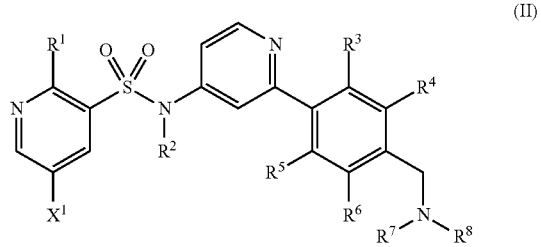

(II)

wherein $R^1$ to $R^8$ are as defined above and $X^1$ is halogen, with morpholine in the presence of a suitable catalyst, b) reacting a compound of formula (VIII) or a salt thereof

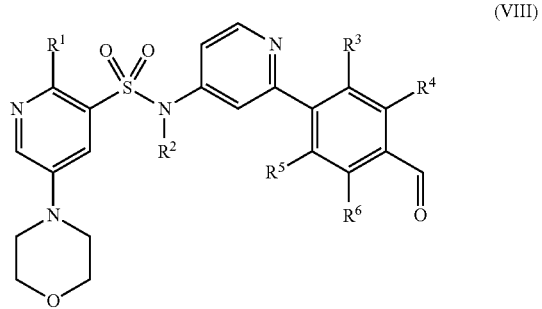

(VIII)

wherein $R^1$ to $R^6$ are as defined above, with a compound of formula (VI) as defined above, in the presence of a reducing agent, c) reacting a compound of formula (X) or a salt thereof

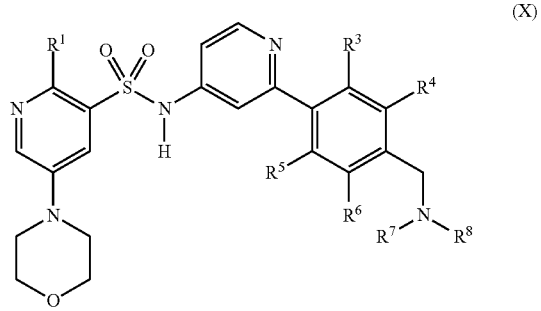

(X)

wherein $R^1$ and $R^3$ to $R^8$ are as defined above, with a compound of formula (XI)

$$R^2-X^4 \qquad (XI)$$

wherein $R^2$ is $C_{1-6}$alkyl optionally substituted by —C(O)OC$_{1-6}$alkyl or —OC(O)C$_{1-6}$alkyl and $X^4$ is halogen, or d) deprotection of a protected form of a compound of formula (I) or a salt thereof.

Methods of Use

The compounds of the invention are inhibitors of kinase activity, in particular PI3-kinase activity. Compounds which are PI3-kinase inhibitors may be useful in the treatment of disorders wherein the underlying pathology is (at least in part) attributable to inappropriate PI3-kinase activity, such as asthma and chronic obstructive pulmonary disease (COPD). "Inappropriate PI3-kinase activity" refers to any PI3-kinase activity that deviates from the normal PI3-kinase activity expected in a particular patient. Inappropriate PI3-kinase may take the form of, for instance, an abnormal increase in activity, or an aberration in the timing and or control of PI3-kinase activity. Such inappropriate activity may result then, for example, from overexpression or mutation of the PI3-kinase leading to inappropriate or uncontrolled activation. Accordingly, in another aspect the invention is directed to methods of treating such disorders.

Such disorders include respiratory diseases including asthma, chronic obstructive pulmonary disease (COPD) and idiopathic pulmonary fibrosis (IPF); ciliopathy including primary ciliary dyskinesia, polycystic liver disease and nephronophthisis; bacterial infections including bacterial respiratory tract infections, for example infections by *S. Pneumoniae, H. Influenzae, M. Catarrhali* sand/or mycobacteria such as *Mycobacterium tuberculosis*, and bacterial exacerbations of respiratory conditions and lung damage such as asthma, COPD and cystic fibrosis; viral infections including viral respiratory tract infections, for example infections by influenza, rhinovirus, respiratory syncytial virus (RSV), human parainfluenza virus (HPIV), adenovirus and/or coronavirus, and viral exacerbation of respiratory conditions and lung damage such as asthma, COPD and cystic fibrosis; other non-viral respiratory infections including aspergillosis and leishmaniasis; allergic diseases including allergic rhinitis, atopic dermatitis and psoriasis; autoimmune diseases including ankylosing spondylitis, Churg-Strauss syndrome, Crohn's disease, Glomerulonephritis, Henoch-Schonlein purpura, idiopathic thrombocytopenic purpura (ITP), interstitial cystitis, pemphigus, primary sclerosing cholangitis, psoriasis, rheumatoid arthritis, sarcoidosis, Sjogren's syndrome, Type 1 diabetes, ulcerative colitis, vasculitis and Wegener's granulomatosis; inflammatory disorders including inflammatory bowel disease; diabetes; cardiovascular diseases including thrombosis, atherosclerosis and hypertension; hematologic malignancies; neurodegenerative diseases; pancreatitis; multiorgan failure; kidney diseases; platelet aggregation; cancer; sperm motility; transplantation rejection; graft rejection; lung injuries; pain including pain associated with rheumatoid arthritis or osteoarthritis, back pain, general inflammatory pain, post hepatic neuralgia, diabetic neuropathy, inflammatory neuropathic pain (trauma), trigeminal neuralgia and Central pain; fibrotic diseases; depression; and psychotic disorders including schizophrenia.

Such fibrotic diseases may include idiopathic pulmonary fibrosis, interstitial lung diseases, non-specific interstitial pneumonia (NSIP), usual interstitial pneumonia (UIP), endomyocardial fibrosis, mediastinal fibrosis, myelofibrosis, retroperitoneal fibrosis, progressive massive fibrosis (a complication of coal workers' pneumoconiosis), nephrogenic systemic fibrosis, Crohn's disease, old myocardial infarction, scleroderma/systemic sclerosis, neurofibromatosis, Hermansky-Pudlak syndrome, diabetic nephropathy, renal fibrosis, hypertrophic cardiomyopathy (HCM), hypertension-related nephropathy, focal segmental glomerulosclerosis (FSGS), radiation-induced fibrosis, uterine leiomyomas (fibroids), alcoholic liver disease, hepatic steatosis, hepatic fibrosis, hepatic cirrhosis, hepatitis C virus (HCV) infection, chronic organ transplant rejection, fibrotic conditions of the skin, keloid scarring, Dupuytren contracture, Ehlers-Danlos syndrome, epidermolysis bullosa dystrophica, oral submucous fibrosis, and fibro-proliferative disorders.

In one embodiment, the disorder is asthma. In a further embodiment, the disorder is COPD.

Within the context of the present invention, the following terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term "psychotic disorder" includes Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

Within the context of the present invention, the term "depression" includes depression and mood disorders including Major Depressive Episode, Manic Episode, Mixed Episode and Hypomanic Episode; Depressive Disorders including Major Depressive Disorder, Dysthymic Disorder (300.4), Depressive Disorder Not Otherwise Specified (311); Bipolar Disorders including Bipolar I Disorder, Bipolar II Disorder (Recurrent Major Depressive Episodes with Hypomanic Episodes) (296.89), Cyclothymic Disorder (301.13) and Bipolar Disorder Not Otherwise Specified (296.80); Other Mood Disorders including Mood Disorder Due to a General Medical Condition (293.83) which includes the subtypes With Depressive Features, With Major Depressive-like Episode, With Manic Features and With Mixed Features), Substance-Induced Mood Disorder (including the subtypes With Depressive Features, With Manic Features and With Mixed Features) and Mood Disorder Not Otherwise Specified (296.90).

The methods of treatment of the invention comprise administering a safe and effective amount of a compound of formula (I) or a pharmaceutically acceptable salt thereof to a patient in need thereof. Individual embodiments of the invention include methods of treating any one of the above-mentioned disorders by administering a safe and effective amount of a compound of formula (I) or a pharmaceutically acceptable salt thereof to a patient in need thereof.

As used herein, "treat" in reference to a disorder means: (1) to ameliorate or prevent the disorder or one or more of the biological manifestations of the disorder, (2) to interfere with (a) one or more points in the biological cascade that leads to or is responsible for the disorder or (b) one or more of the biological manifestations of the disorder, (3) to alleviate one or more of the symptoms or effects associated with the disorder, or (4) to slow the progression of the disorder or one or more of the biological manifestations of the disorder.

As indicated above, "treatment" of a disorder includes prevention of the disorder. The skilled artisan will appreciate that "prevention" is not an absolute term. In medicine, "prevention" is understood to refer to the prophylactic administration of a drug to substantially diminish the likelihood or severity of a disorder or biological manifestation thereof, or to delay the onset of such disorder or biological manifestation thereof. In one embodiment, the methods of the invention are directed to treating a disorder. In another embodiment, the methods of the invention are directed to preventing a disorder.

As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human (including adults and children) or other animal. In one embodiment, "patient" refers to a human.

The compounds of formula (I) or pharmaceutically acceptable salts thereof may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. Inhalation refers to administration into the patient's lungs whether inhaled through the mouth or through the nasal passages. In one embodiment, the compounds of formula (I) or pharmaceutically acceptable salts thereof may be administered orally. In another embodiment, the compounds of formula (I) or pharmaceutically acceptable salts thereof may be administered by inhalation. In a further embodiment, the compounds of formula (I) or pharmaceutically acceptable salts thereof may be administered intranasally.

The compounds of formula (I) or pharmaceutically acceptable salts thereof may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for a compound of formula (I) or a pharmaceutically acceptable salt thereof depend on the pharmacokinetic properties of that compound, such as absorption, distribution, and half-life, which can be determined by the skilled artisan. In addition, suitable dosing regimens, including the duration such regimens are administered, for a compound of formula (I) or a pharmaceutically acceptable salt thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical daily dosages for oral administration range from 0.001 mg to 50 mg per kg of total body weight, for example from 1 mg to 10 mg per kg of total body weight. For example, daily dosages for oral administration may be from 0.5 mg to 2 g per patient, such as 10 mg to 1 g per patient.

Additionally, the compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of the activity of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleavable in vivo. Such modifications, which include the preparation of phosphates, amides, esters, thioesters, carbonates, and carbamates, are well known to those skilled in the art.

In one aspect, the invention thus provides a method of treating a disorder mediated by inappropriate PI3-kinase activity comprising administering a safe and effective amount of a compound of formula (I) or a pharmaceutically acceptable salt thereof to a patient in need thereof.

In one embodiment, the invention thus provides a method of treating a disorder mediated by inappropriate PI3-kinase activity comprising administering a safe and effective amount of N-(2-(2-fluoro-4-((4-isopropylpiperazin-1-yl)methyl)phenyl)pyridin-4-yl)-2-methoxy-5-morpholinopyridine-3-sulfonamide or a pharmaceutically acceptable salt thereof to a patient in need thereof In one embodiment, the disorder mediated by inappropriate PI3-kinase activity is selected from the group consisting of respiratory diseases (including asthma, chronic obstructive pulmonary disease (COPD) and idiopathic pulmonary fibrosis (IPF)); ciliopathy (including primary ciliary dyskinesia, polycystic liver disease and nephronophthisis); bacterial infections (including bacterial respiratory tract infections, for example infections by S. Pneumoniae, H. Influenzae, M. Catarrhalis and/or mycobacteria such as Mycobacterium tuberculosis) and bacterial exacerbations of respiratory conditions and lung damage (such as asthma, COPD and cystic fibrosis); viral infections (including viral respiratory tract infections, for example infections by influenza, rhinovirus, respiratory syncytial virus (RSV), human parainfluenza virus (HPIV), adenovirus and/or coronavirus) and viral exacerbations of respiratory conditions and lung damage (such as asthma, COPD and cystic fibrosis); other non-viral respiratory infections (including aspergillosis and leishmaniasis); allergic diseases (including allergic rhinitis, atopic dermatitis and psoriasis); autoimmune diseases (including ankylosing spondylitis, Churg-Strauss syndrome, Crohn's disease, Glomerulonephritis, Henoch-Schonlein purpura, idiopathic thrombocytopenic purpura (ITP), interstitial cystitis, pemphigus, primary sclerosing cholangitis, psoriasis, rheumatoid arthritis, sarcoidosis, Sjogren's syndrome, Type 1 diabetes, ulcerative colitis, vasculitis and Wegener's granulomatosis); inflammatory disorders (including inflammatory bowel disease); diabetes; cardiovascular diseases (including thrombosis, atherosclerosis and hypertension); hematologic malignancies; neurodegenerative diseases; pancreatitis; multiorgan failure; kidney diseases; platelet aggregation; cancer; sperm motility; transplantation rejection; graft rejection; lung injuries; pain (including pain associated with rheumatoid arthritis or osteoarthritis, back pain, general inflammatory pain, post hepatic neuralgia, diabetic neuropathy, inflammatory neuropathic pain (trauma), trigeminal neuralgia and Central pain); fibrotic diseases; depression; and psychotic disorders (including schizophrenia).

In one embodiment, the disorder mediated by inappropriate PI3-kinase activity is a respiratory disease. In another embodiment, the disorder mediated by inappropriate PI3-kinase activity is asthma. In a further embodiment, the disorder mediated by inappropriate PI3-kinase activity is chronic obstructive pulmonary disease (COPD).

In one aspect, the invention provides a compound of formula (I) or a pharmaceutically acceptable salt thereof for use in medical therapy.

In one embodiment, the invention provides N-(2-(2-fluoro-4-((4-isopropylpiperazin-1-yl)methyl)phenyl)pyridin-4-yl)-2-methoxy-5-morpholinopyridine-3-sulfonamide or a pharmaceutically acceptable salt thereof for use in medical therapy.

In another aspect, the invention provides a compound of formula (I) or a pharmaceutically acceptable salt thereof for use in the treatment of a disorder mediated by inappropriate PI3-kinase activity.

In one embodiment, the invention provides N-(2-(2-fluoro-4-((4-isopropylpiperazin-1-yl)methyl)phenyl)pyridin-4-yl)-2-methoxy-5-morpholinopyridine-3-sulfonamide or a pharmaceutically acceptable salt thereof for use in the treatment of a disorder mediated by inappropriate PI3-kinase activity.

In a further aspect, the invention provides the use of a compound of formula (I) or a pharmaceutically acceptable salt thereof in the manufacture of a medicament for use in the treatment of a disorder mediated by inappropriate PI3-kinase activity.

In one embodiment, the invention provides the use of N-(2-(2-fluoro-4-((4-isopropylpiperazin-1-yl)methyl)phenyl)pyridin-4-yl)-2-methoxy-5-morpholinopyridine-3-sulfonamide or a pharmaceutically acceptable salt thereof in the manufacture of a medicament for use in the treatment of a disorder mediated by inappropriate PI3-kinase activity.

A number of different genetic variants in PI3Kδ have been observed (Jou et al., International Journal of Immunogenetics, 2006, 33, 361 to 369). One mutation (c.3061G>A, corresponding to m.3256G>A in the mRNA wherein the nucleotide number is based on the sequence data on GenBank: NM_005026) observed in a highly conserved position in the domain responsible for catalytic function results in a glutamic acid to lysine substitution (E1021K). It is believed that this mutation may result in patients being particularly susceptible to developing respiratory infections and/or exacerbations of respiratory infections, and damage to the airway wall, large and small airways, and lung parenchyma (Angulo et al., Science DOI: 10.1125/science. 1243292). Other gain of function mutations identified in the PIK3CD gene and leading to immune deficiencies include the amino acid residue substitution N334K or E525K (Lucas et al. Nat. Immunol. (2014) 15 p. 88-97). Mutations leading to aberrant splicing of PIK3R1 exon 10 and truncation of the p85 a protein result in elevated PI3Kδ activity and to symptoms similar to the gain of function mutations in the PIK3CD gene (Deau et al. J. Clin. Invest. (2014) 124(9) p. 3923-8).

Thus, in one aspect, the invention thus provides a method of treating or preventing a respiratory infection, treating airway damage, and/or preventing airway injury in a patient with a PI3Kδ mutation, or increased PI3Kδ expression or activity, comprising administering a safe and effective amount of a compound of formula (I) or a pharmaceutically acceptable salt thereof to a patient in need thereof.

In one embodiment, the invention provides a compound of formula (I) or a pharmaceutically acceptable salt thereof for use in the treatment or prevention of a respiratory infection, the treatment of airway damage, and/or the prevention of airway injury in a patient with a PI3Kδ mutation, or increased PI3Kδ expression or activity.

In another embodiment, the invention provides the use of a compound of formula (I) or a pharmaceutically acceptable salt thereof in the manufacture of a medicament for use in the treatment or prevention of a respiratory infection, the treatment of airway damage, and/or the prevention of airway injury in a patient with a PI3Kδ mutation, or increased PI3Kδ expression or activity.

In another embodiment, the present invention provides a compound of formula (I) or a pharmaceutically acceptable salt thereof for use in the treatment or prevention of a respiratory infection, the treatment of airway damage, and/or the prevention of airway injury in a patient, comprising:
  a) assaying a sample from the patient,
  b) determining if the patient has a PI3Kδ mutation, or increased PI3Kδ expression or activity, and
  c) administering a therapeutically effective amount of a compound of formula (I) or a pharmaceutically acceptable salt thereof to the patient if they have a PI3Kδ mutation, or increased PI3Kδ expression or activity.

In another embodiment, the invention provides a compound of formula (I) or a pharmaceutically acceptable salt thereof for use in the treatment or prevention of a respiratory infection, the treatment of airway damage, and/or the prevention of airway injury in a patient classified as a responder, wherein a responder is characterised by the presence of a PI3Kδ mutation, or increased PI3Kδ expression or activity.

In another embodiment, the invention provides use of a compound of formula (I) or a pharmaceutically acceptable salt thereof in the manufacture of a medicament for use in the treatment or prevention of a respiratory infection, the treatment of airway damage, and/or the prevention of airway injury in a patient classified as a responder, wherein a responder is characterised by the presence of a PI3Kδ mutation, or increased PI3Kδ expression or activity.

In a further embodiment, the invention provides a method of evaluating therapy with a compound of formula (I) or a pharmaceutically acceptable salt thereof, comprising:
  a) obtaining a sample from the patient,
  b) testing for a PI3Kδ mutation, or increased PI3Kδ expression or activity, and
  c) determining if the patient should undergo therapy with a compound of formula (I) or a pharmaceutically acceptable salt thereof if a PI3Kδ mutation, or increased PI3Kδ expression or activity, is present.

Such respiratory infections may be the result of bacterial infections including, for example, infections by *S. Pneumoniae, H. Influenzae, M. Catarrhalis* and/or mycobacteria such as *Mycobacterium tuberculosis*, viral infections including, for example, infections by influenza, rhinovirus, respiratory syncytial virus (RSV), human parainfluenza virus (HPIV), adenovirus and/or coronavirus; and other non-viral respiratory infections including aspergillosis and/or leishmaniasis. In one embodiment, patients with a PI3Kδ mutation may be particularly susceptible to developing respiratory infections and/or exacerbations of respiratory infections as a result of bacterial infections by *S. Pneumoniae, H. Influenzae*, and/or *M. Catarrhalis*.

As used herein, the term "airway damage" refers to damage to the airway wall, large and small airways, and/or lung parenchyma which is present at the time a patient commences treatment. Airway damage, such as inflammation, scarring and/or remodelling, may be caused by, for example, repeated respiratory infections in a patient with a PI3K5 mutation.

As used herein, the term "airway injury" refers to damage, or further damage, to the airway wall, large and small airways, and/or lung parenchyma which may develop in a patient if treatment does not occur.

As used herein, the term "responder" means someone who is identified (using a particular test or method) to be more likely to derive benefit in response to treatment (e.g. positive response to drug, reduction in adverse events, etc.). It is understood that not all people who have been identified as a responder will necessarily derive benefit, but as a patient class, they are more likely to do so. For example, it may be that out of the total untested diseased population, approximately 80% of that population derive benefit from a drug, but out of the group of "responders" (i.e. those individuals who have been tested, and identified as a responder according to the set criteria) approximately 99% will derive benefit.

As used herein, the term "evaluating therapy" means determining whether therapy with a compound of formula (I), or a pharmaceutically acceptable salt thereof, would be beneficial to a patient.

Patients with a PI3Kδ mutation may be particularly susceptible to an exacerbation of a respiratory infection. As used herein, the term "exacerbation of a respiratory infection" refers to a respiratory infection characterised by the worsening of an underlying persistent respiratory infection, including bacterial infections, viral infections and/or other non-viral respiratory infections. In one embodiment, the present invention thus provides a method of treating or preventing an exacerbation of a respiratory infection in a patient with a PI3Kδ mutation comprising administering a safe and effective amount of a compound of formula (I) or a pharmaceutically acceptable salt thereof to a patient in need thereof.

In one embodiment, the PI3Kδ mutation results in the substitution of glutamic acid for lysine. In another embodiment, the PI3Kδ mutation results in the substitution of glutamic acid for lysine at codon 1021 (E1021K).

In one embodiment, the PI3Kδ mutation results in a single base-pair missense mutation m.3256G>A in the mRNA (wherein the nucleotide number is based on the sequence data on GenBank: NM_005026).

In one embodiment, the PI3Kδ mutation is c.3061G>A.

Compositions

The compounds of formula (I) and pharmaceutically acceptable salts thereof will normally, but not necessarily, be formulated into pharmaceutical compositions prior to administration to a patient.

Accordingly, in one aspect the invention is directed to pharmaceutical compositions comprising a compound of formula (I) or a pharmaceutically acceptable salt thereof and one or more pharmaceutically acceptable excipients.

In another aspect the invention is directed to pharmaceutical compositions comprising 0.05 to 1000 mg of a compound of formula (I) or a pharmaceutically acceptable salt thereof and 0.1 to 2 g of one or more pharmaceutically acceptable excipients.

In a further aspect the invention is directed to a pharmaceutical composition for the treatment or prophylaxis of a disorder mediated by inappropriate PI3-kinase activity comprising a compound of formula (I) or a pharmaceutically acceptable salt thereof.

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.5 mg to 1 g, or from 1 mg to 700 mg, or from 5 mg to 100 mg of a compound of formula (I) or a pharmaceutically acceptable salt thereof.

The pharmaceutical compositions of the invention typically contain one compound of formula (I) or a pharmaceutically acceptable salt thereof.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or a pharmaceutically acceptable salt thereof when administered to a patient and interactions which would result in pharmaceutical compositions that are not pharmaceutically acceptable are avoided. In addition, each excipient must of course be pharmaceutically-acceptable eg of sufficiently high purity.

The compound of formula (I) or a pharmaceutically acceptable salt thereof and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Accordingly, in another aspect the invention is directed to process for the preparation of a pharmaceutical composition comprising a compound of formula (I) or a pharmaceutically acceptable salt thereof and one or more pharmaceutically acceptable excipients which comprises mixing the ingredients. A pharmaceutical composition comprising a compound of formula (I) or a pharmaceutically acceptable salt thereof may be prepared by, for example, admixture at ambient temperature and atmospheric pressure.

In one embodiment, the compounds of formula (I) or pharmaceutically acceptable salts thereof will be formulated for oral administration. In another embodiment, the compounds of formula (I) or pharmaceutically acceptable salts thereof will be formulated for inhaled administration. In a further embodiment, the compounds of formula (I) or pharmaceutically acceptable salts thereof will be formulated for intranasal administration.

In one aspect, the invention is directed to a solid oral dosage form such as a tablet or capsule comprising a safe and effective amount of a compound of formula (I) or a pharmaceutically acceptable salt thereof and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesuim stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of formula (I) or pharmaceutically acceptable salts thereof may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of formula (I) or pharmaceutically acceptable salts thereof may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of formula (I) or a pharmaceutically acceptable salt thereof. Syrups can be prepared by dissolving the compound of formula (I) or a pharmaceutically acceptable salt thereof in a suitably flavored aqueous solution, while elixirs are prepared through the use of a non-toxic alcoholic vehicle. Suspensions can be formulated by dispersing the compound of formula (I) or a pharmaceutically acceptable salt thereof in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

In another aspect, the invention is directed to a dosage form adapted for administration to a patient by inhalation, for example as a dry powder, an aerosol, a suspension, or a solution composition. In one embodiment, the invention is directed to a dosage form adapted for administration to a patient by inhalation as a dry powder. In a further embodiment, the invention is directed to a dosage form adapted for administration to a patient by inhalation via a nebulizer.

Dry powder compositions for delivery to the lung by inhalation typically comprise a compound of formula (I) or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation. Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom.

For example, the blisters may be arranged in a generally circular fashion on a disc-form blister pack, or the blisters may be elongate in form, for example comprising a strip or a tape. Each capsule, cartridge, or blister may, for example, contain between 20 µg-10 mg of the compound of formula (I) or a pharmaceutically acceptable salt thereof.

Aerosols may be formed by suspending or dissolving a compound of formula (I) or a pharmaceutically acceptable salt thereof in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (I) or a pharmaceutically acceptable salt thereof will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

There is thus provided as a further aspect of the invention a pharmaceutical aerosol formulation comprising a compound of formula (I) or a pharmaceutically acceptable salt thereof and a fluorocarbon or hydrogen-containing chlorofluorocarbon as propellant, optionally in combination with a surfactant and/or a cosolvent.

According to another aspect of the invention, there is provided a pharmaceutical aerosol formulation wherein the propellant is selected from 1,1,1,2-tetrafluoroethane, 1,1,1,2,3,3,3-heptafluoro-n-propane and mixtures thereof.

The formulations of the invention may be buffered by the addition of suitable buffering agents.

Capsules and cartridges for use in an inhaler or insufflator, of for example gelatine, may be formulated containing a powder mix for inhalation of a compound of formula (I) or a pharmaceutically acceptable salt thereof and a suitable powder base such as lactose or starch. Each capsule or cartridge may generally contain from 20 µg to 10 mg of the compound of formula (I) or pharmaceutically acceptable salt thereof. Alternatively, the compound of formula (I) or pharmaceutically acceptable salt thereof may be presented without excipients such as lactose.

The proportion of the active compound of formula (I) or pharmaceutically acceptable salt thereof in the local compositions according to the invention depends on the precise type of formulation to be prepared but will generally be within the range of from 0.001 to 10% by weight. Generally, for most types of preparations, the proportion used will be within the range of from 0.005 to 1%, for example from 0.01 to 0.5%. However, in powders for inhalation or insufflation the proportion used will normally be within the range of from 0.1 to 5%.

Aerosol formulations are preferably arranged so that each metered dose or "puff" of aerosol contains from 20 μg to 10 mg, preferably from 20 μg to 2000 μg, more preferably from about 20 μg to 500 μg of a compound of formula (I). Administration may be once daily or several times daily, for example 2, 3, 4 or 8 times, giving for example 1, 2 or 3 doses each time. The overall daily dose with an aerosol will be within the range from 100 μg to 10 mg, preferably from 200 μg to 2000 μg. The overall daily dose and the metered dose delivered by capsules and cartridges in an inhaler or insufflator will generally be double that delivered with aerosol formulations.

In the case of suspension aerosol formulations, the particle size of the particulate (e.g., micronised) drug should be such as to permit inhalation of substantially all the drug into the lungs upon administration of the aerosol formulation and will thus be less than 100 microns, desirably less than 20 microns, and in particular in the range of from 1 to 10 microns, such as from 1 to 5 microns, more preferably from 2 to 3 microns.

The formulations of the invention may be prepared by dispersal or dissolution of the medicament and a compound of formula (I) or a pharmaceutically acceptable salt thereof in the selected propellant in an appropriate container, for example, with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol formulations according to the invention may be measured by conventional techniques, for example, by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaeia 1988, pages A204-207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

The term "metered dose inhaler" or MDI means a unit comprising a can, a secured cap covering the can and a formulation metering valve situated in the cap. MDI system includes a suitable channelling device. Suitable channelling devices comprise for example, a valve actuator and a cylindrical or cone-like passage through which medicament may be delivered from the filled canister via the metering valve to the nose or mouth of a patient such as a mouthpiece actuator.

MDI canisters generally comprise a container capable of withstanding the vapour pressure of the propellant used such as a plastic or plastic-coated glass bottle or preferably a metal can, for example, aluminium or an alloy thereof which may optionally be anodised, lacquer-coated and/or plastic-coated (for example incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g. see Byron, above and WO96/32099). Preferably the canister is fitted with a cap assembly, wherein a drug-metering valve is situated in the cap, and said cap is crimped in place.

In one embodiment of the invention the metallic internal surface of the can is coated with a fluoropolymer, more preferably blended with a non-fluoropolymer. In another embodiment of the invention the metallic internal surface of the can is coated with a polymer blend of polytetrafluoroethylene (PTFE) and polyethersulfone (PES). In a further embodiment of the invention the whole of the metallic internal surface of the can is coated with a polymer blend of polytetrafluoroethylene (PTFE) and polyethersulfone (PES).

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, bromobutyl, EPDM, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™).

In various embodiments, the MDIs may also be used in conjunction with other structures such as, without limitation, overwrap packages for storing and containing the MDIs, including those described in U.S. Pat. Nos. 6,119,853; 6,179,118; 6,315,112; 6,352,152; 6,390,291; and 6,679,374, as well as dose counter units such as, but not limited to, those described in U.S. Pat. Nos. 6,360,739 and 6,431,168.

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method for preparing suspension aerosol formulations a metering valve is crimped onto an aluminium can to form an empty canister. The particulate medicament is added to a charge vessel and liquefied propellant together with the optional excipients is pressure filled through the charge vessel into a manufacturing vessel. The drug suspension is mixed before recirculation to a filling machine and an aliquot of the drug suspension is then filled through the metering valve into the canister. In one example bulk manufacturing method for preparing solution aerosol formulations a metering valve is crimped onto an aluminium can to form an empty canister. The liquefied propellant together with the optional excipients and the dissolved medicament is pressure filled through the charge vessel into a manufacturing vessel.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing.

Suspensions and solutions comprising a compound of formula (I) or a pharmaceutically acceptable salt thereof may also be administered to a patient via a nebulizer. The solvent or suspension agent utilized for nebulization may be any pharmaceutically-acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically-acceptable excipients may be added to the suspension or solution. The compound of formula (I) or pharmaceutically acceptable salt thereof may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of formula (I) or pharmaceutically acceptable salt thereof. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

In a further aspect, the invention is directed to a dosage form adapted for intranasal administration.

Formulations for administration to the nose may include pressurised aerosol formulations and aqueous formulations administered to the nose by pressurised pump. Formulations which are non-pressurised and adapted to be administered topically to the nasal cavity are of particular interest. Suitable formulations contain water as the diluent or carrier for this purpose. Aqueous formulations for administration to the lung or nose may be provided with conventional excipients such as buffering agents, tonicity modifying agents and the like. Aqueous formulations may also be administered to the nose by nebulisation.

The compounds of formula (I) or pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO05/044354, the entire content of which is hereby incorporated herein by reference.

The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. In one embodiment, the fluid dispenser is of the general type illustrated in FIGS. 30-40 of WO05/044354.

Pharmaceutical compositions adapted for intranasal administration wherein the carrier is a solid include a coarse powder having a particle size for example in the range 20 to 500 microns which is administered by rapid inhalation through the nasal passage from a container of the powder held close up to the nose. Suitable compositions wherein the carrier is a liquid, for administration as a nasal spray or as nasal drops, include aqueous or oil solutions of the compound of formula (I) or a pharmaceutically acceptable salt thereof.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or nonionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered by one or more applications per day to the affected area; over skin areas occlusive dressings may advantageously be used. Continuous or prolonged delivery may be achieved by an adhesive reservoir system.

For treatments of the eye or other external tissues, for example mouth and skin, the compositions may be applied as a topical ointment or cream. When formulated in an ointment, the compound of formula (I) or a pharmaceutically acceptable salt thereof may be employed with either a paraffinic or a water-miscible ointment base. Alternatively, the compound of formula (I) or pharmaceutically acceptable salt thereof may be formulated in a cream with an oil-in-water cream base or a water-in-oil base.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The compound and pharmaceutical formulations according to the invention may be used in combination with or include one or more other therapeutic agents, for example selected from anti-inflammatory agents, anticholinergic agents, β2-adrenoreceptor agonists, leukotriene antagonists (such as montelukast, zafirlukast or pranlukast), antiinfective agents, antihistamines, antigen immunotherapy, corticosteroids (such as fluticasone propionate, fluticasone furoate, beclomethasone diproprionate, budesonide, ciclesonide, mometasone furoate, triamcinolone or flunisolide), iNOS inhibitors, tryptase inhibitors, IKK2 inhibitors, p38 inhibitors, Syk inhibitors, elastase inhibitors, beta-2 integrin antagonists, adenosine a2a agonists, chemokine antagonists such as CCR3 antagonists or CCR4 antagonists, mediator release inhibitors (such as sodium chromoglycate), 5-lipoxygenase inhibitors (zyflo), DP1 antagonists, DP2 antagonists, PDE4 inhibitors, PI3-kinase inhibitors, PI4-kinase inhibitors, ITK inhibitors, LP (lysophosphatidic) inhibitors, FLAP (5-lipoxygenase activating protein) inhibitors (such as sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate), DMARDs (disease-modifying anti-rheumatic drugs) (such as methotrexate, leflunomide or azathioprine), monoclonal antibody therapy (such as anti-TSLP, anti-IgE, anti-TNF, anti-IL-5, anti-IL-6, anti-IL-12 or anti-IL-1), receptor therapies (such as etanercept), and/or antigen non-specific immunotherapies (such as interferon or other cytokines/chemokines, cytokine/chemokine receptor modulators, cytokine agonists or antagonists, or TLR agonists).

The invention thus provides, in a further aspect, a combination comprising a compound of formula (I) or a pharmaceutically acceptable salt thereof together with one or more other therapeutically active agents, for example selected from an anti-inflammatory agent, an anticholinergic agent, a β2-adrenoreceptor agonist, a leukotriene antagonist, an antiinfective agent, an antihistamine, antigen immunotherapy, a corticosteroid, an iNOS inhibitor, a tryptase inhibitor, an IKK2 inhibitor, a p38 inhibitor, a Syk inhibitor, an elastase inhibitor, a beta-2 integrin antagonist, an adenosine a2a agonist, a chemokine antagonist, a mediator release inhibitor, a 5-lipoxygenase inhibitors, a DP1 antagonist, a DP2 antagonist, a PDE4 inhibitor, a PI3-kinase inhibitor, a PI4-kinase inhibitor, an ITK inhibitor, a LP (lysophosphatidic) inhibitor, a FLAP (5-lipoxygenase activating protein) inhibitor, a DMARD, monoclonal antibody therapy, receptor therapy, and/or antigen non-specific immunotherapy.

In one embodiment, the invention encompasses a method of treating a disorder mediated by inappropriate PI3-kinase activity comprising administering a safe and effective amount of a combination comprising a compound of formula (I) or a pharmaceutically acceptable salt thereof together with one or more therapeutically active agents.

Certain compounds of the invention may show selectivity for PI3Kδ over other PI3-kinases. The invention thus provides, in a further aspect, a combination comprising a compound of formula (I) or a pharmaceutically acceptable salt thereof which is selective for PI3Kδ together with a compound or pharmaceutically acceptable salt thereof which is selective for another PI3-kinase, for example PI3Kγ.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimise the activity and/or stability and/or physical characteristics, such as solubility, of the therapeutic ingredient. It will be clear also that, where appropriate, the therapeutic ingredients may be used in optically pure form.

In one embodiment, the invention encompasses a combination comprising a compound of formula (I) or a pharmaceutically acceptable salt thereof together with a β2-adrenoreceptor agonist.

Examples of β2-adrenoreceptor agonists include salmeterol (which may be a racemate or a single enantiomer such as the R-enantiomer), salbutamol (which may be a racemate or a single enantiomer such as the R-enantiomer), formoterol (which may be a racemate or a single duastereomer such as the R,R-diastereomer), salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment, long-acting β2-adrenoreceptor agonists, for example, compounds which provide effective bronchodilation for about 12 hrs or longer, are preferred.

Other β2-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160.

Examples of β2-adrenoreceptor agonists include:
3-(4-{[6-({(2R)-2-hydroxy-2-[4-hydroxy-3-(hydroxymethyl)phenyl]ethyl}amino) hexyl]oxy}butyl)benzenesulfonamide;
3-(3-{[7-({(2R)-2-hydroxy-2-[4-hydroxy-3-hydroxymethyl)phenyl]ethyl}amino)heptyl]oxy}propyl) benzenesulfonamide;
4-{(1R)-2-[(6-{2-[(2,6-dichlorobenzy)oxy]ethoxy}hexyl) amino]-1-hydroxyethyl}-2-(hydroxymethyl) phenol;
4-{(1R)-2-[(6-{4-[3-(cyclopentylsulfonyl)phenyl] butoxy}hexyl)amino]-1-hydroxyethyl}-2-(hydroxymethyl)phenol;
N-[2-hydroxyl-5-[(1R)-1-hydroxy-2-[[2-4-[[(2R)-2-hydroxy-2-phenylethyl]amino]phenyl]-ethyl]amino]ethyl] phenyl]formamide;

N-2{2-[4-(3-phenyl-4-methoxyphenyl)aminophenyl]ethyl}-2-hydroxy-2-(8-hydroxy-2(1H)-quinolinon-5-yl)ethylamine; and 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

The $\beta_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

In one embodiment, the invention encompasses a combination comprising a compound of formula (I) or a pharmaceutically acceptable salt thereof together with a leukotriene antagonist. Suitable leukotriene antagonists include, for example, montelukast.

Suitable anti-inflammatory agents include corticosteroids. Suitable corticosteroids which may be used in combination with the compounds of formula (I) or pharmaceutically acceptable salts thereof are those oral and inhaled corticosteroids and their pro-drugs which have anti-inflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid (2-oxo-tetrahydro-furan-3S-yl) ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid cyanomethyl ester and 6α,9α-difluoro-11β-hydroxy-16α-methyl-17α-(1-methylcyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydoxy-16α-methyl-3-oxo-androsta-1,4-diene-17β-carbothioic acid S-fluoromethyl ester.

Examples of corticosteroids may include those described in WO2002/088167, WO2002/100879, WO2002/12265, WO2002/12266, WO2005/005451, WO2005/005452, WO2006/072599 and WO2006/072600.

Non-steroidal compounds having glucocorticoid agonism that may possess selectivity for transrepression over transactivation and that may be useful in combination therapy include those covered in the following patents: WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651 and WO03/08277. Further non-steroidal compounds are covered in: WO2006/000401, WO2006/000398 and WO2006/015870.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), tryptase and elastase inhibitors, beta-2 integrin antagonists and adenosine receptor agonists or antagonists (e.g. adenosine 2a agonists), cytokine antagonists, or inhibitors of cytokine synthesis, or 5-lipoxygenase inhibitors.

In one embodiment, the invention provides the use of the compounds of formula (I) in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxy-phenyl)cyclohexan-1-one and cis-[4-cya no-4-(3-cyclopropylmethoxy-4-difluoromethoxy-phenyl) cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep., 1996; this patent and the compounds it discloses are incorporated herein in full by reference.

Other compounds include AWD-12-281 from Elbion (Hofgen, N. et al. 15th EFMC Int Symp Med Chem (September 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L.J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther,1998, 284(1): 162), and T2585.

Further compounds are disclosed in the published international patent application WO04/024728 (Glaxo Group Ltd), WO04/056823 (Glaxo Group Ltd) and WO04/103998 (Glaxo Group Ltd) (e.g. Example 399 or 544 disclosed therein). Further compounds are also disclosed in WO2005/

058892, WO2005/090348, WO2005/090353, and WO2005/090354, all in the name of Glaxo Group Limited.

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Additional compounds are disclosed in WO 2005/037280, WO 2005/046586 and WO 2005/104745, incorporated herein by reference. The present combinations include, but are not limited to:
(3-endo)-3-(2,2-di-2-thienylethenyl)-8,8-dimethyl-8-azoniabicyclo[3.2.1]octane iodide;
(3-endo)-3-(2-cyano-2,2-diphenylethyl)-8,8-dimethyl-8-azoniabicyclo[3.2.1]octane bromide;
4-[hydroxy(diphenyl)methyl]-1-{2-[(phenylmethyl)oxy]ethyl}-1-azoniabicyclo[2.2.2]octane bromide; and
(1R,5S)-3-(2-cyano-2,2-diphenylethyl)-8-methyl-8-{2-[(phenylmethyl)oxy]ethyl}-8-azoniabicyclo[3.2.1]octane bromide.

Other anticholinergic agents include compounds which are disclosed in U.S. patent application 60/487981 including, for example:
(3-endo)-3-(2,2-di-2-thienylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane 4-methyl-benzenesulfonate;
(3-endo)-8,8-dimethyl-3-[2-phenyl-2-(2-thienypethenyl]-8-azoniabicyclo[3.2.1]octane bromide; and/or
(3-endo)-8,8-dimethyl-3-[2-phenyl-2-(2-pyridinyl)ethenyl]-8-azoniabicyclo[3.2.1]octane bromide.

Further anticholinergic agents include compounds which are disclosed in U.S. patent application 60/511009 including, for example:
(endo)-3-(2-methoxy-2,2-di-thiophen-2-yl-ethyl)-8,8-dimethyl-8-azonia-bicyclo[3.2.1]octane iodide;
3-((endo)-8-methyl-8-aza-bicyclo[3.2.1]oct-3-yl)-2,2-diphenyl-propionitrile;
(endo)-8-methyl-3-(2,2,2-triphenyl-ethyl)-8-aza-bicyclo[3.2.1]octane;
3-((endo)-8-methyl-8-aza-bicyclo[3.2.1]oct-3-yl)-2,2-diphenyl-propionamide;
3-((endo)-8-methyl-8-aza-bicyclo[3.2.1]oct-3-yl)-2,2-diphenyl-propionic acid;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
3-((endo)-8-methyl-8-aza-bicyclo[3.2.1]oct-3-yl)-2,2-diphenyl-propan-1-ol;
N-benzyl-3-((endo)-8-methyl-8-aza-bicyclo[3.2.1]oct-3-yl)-2,2-diphenyl-propionamide;
(endo)-3-(2-carbamoyl-2,2-diphenyl-ethyl)-8,8-dimethyl-8-azonia-bicyclo[3.2.1]octane iodide;
1-benzyl-3-[3-((endo)-8-methyl-8-aza-bicyclo[3.2.1]oct-3-yl)-2,2-diphenyl-propyl]-urea;
1-ethyl-3-[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-acetamide;
N-[3-((endo)-8-methyl-8-aza-bicyclo[3.2.1]oct-3-yl)-2,2-diphenyl-propyl]-benzamide;
3-((endo)-8-methyl-8-aza-bicyclo[3.2.1]oct-3-yl)-2,2-di-thiophen-2-yl-propionitrile;
(endo)-3-(2-cyano-2,2-di-thiophen-2-yl-ethyl)-8,8-dimethyl-8-azonia-bicyclo[3.2.1]octane iodide;
N-[3-((endo)-8-methyl-8-aza-bicyclo[3.2.1]oct-3-yl)-2,2-diphenyl-propyl]-benzenesulfonamide;
[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-methanesulfonamide; and/or
(endo)-3-{2,2-diphenyl-3-[(1-phenyl-methanoyl)-amino]-propyl}-8,8-dimethyl-8-azonia-bicyclo[3.2.1]octane bromide.

Further compounds include:
(endo)-3-(2-methoxy-2,2-di-thiophen-2-yl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
(endo)-3-(2-carbamoyl-2,2-diphenyl-ethyl)-8,8-dimethyl-8-azonia-bicyclo[3.2.1]octane iodide;
(endo)-3-(2-cyano-2,2-di-thiophen-2-yl-ethyl)-8,8-dimethyl-8-azonia-bicyclo[3.2.1]octane iodide; and/or
(endo)-3-{2,2-diphenyl-3-[(1-phenyl-methanoyl)-amino]-propyl}-8,8-dimethyl-8-azonia-bicyclo[3.2.1]octane bromide.

In one embodiment the invention provides a combination comprising a compound of formula (I) or a pharmaceutically acceptable salt thereof together with an H1 antagonist. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising a compound of formula (I) or a pharmaceutically acceptable salt thereof together with an H3 antagonist (and/or inverse agonist). Examples of H3 antagonists include, for example, those compounds disclosed in WO2004/035556 and in WO2006/045416. Other histamine receptor antagonists which may be used in combination with the compounds of the present invention include antagonists (and/or inverse agonists) of the H4 receptor, for example, the compounds disclosed in Jablonowski et al., *J. Med. Chem.* 46:3957-3960 (2003).

In one embodiment the invention provides a combination comprising a compound of formula (I) or a pharmaceutically acceptable salt thereof together with an anti-infective agent. The anti-infective agent may be an antibiotic, an antiviral or an antifungal. Examples of suitable antibiotics may include amoxicillin/clavulanate, flucloxacillin, cefalexin, cefixime, erythromycin, ciprofloxacin and tobramycin. Examples of suitable antivirals may include oseltamivir, zanamivir and ribavirin. Examples of suitable antifungals may include fluconazole and itraconazole.

In one embodiment the combination comprising a compound of formula (I) or a pharmaceutically acceptable salt thereof together with an anti-infective agent may be administered by inhalation. Examples of anti-infective agents particularly suitable for inhalation include those that may be inhaled or nebulized, for example, antibiotics such as tobramycin or ciprofloxacin, and antivirals such as zanamivir or ribavirin.

In one embodiment the invention provides a combination comprising a compound of formula (I) or a pharmaceutically acceptable salt thereof together with an anti-infective agent that has a compatible duration of action with the compound of formula (I). By the term "compatible duration of action" as used herein, is meant that the duration of action is such that both compounds may be administered to treat a particular patient, for example, they may be administered the same number of times each day such as once daily or 2, 3, 4 or 8 times.

The invention thus provides, in a further aspect, a combination comprising a compound of formula (I) or a pharmaceutically acceptable salt thereof together with a PDE4 inhibitor.

The invention thus provides, in a further aspect, a combination comprising a compound of formula (I) or a pharmaceutically acceptable salt thereof together with a $\beta_2$-adrenoreceptor agonist.

The invention thus provides, in a further aspect, a combination comprising a compound of formula (I) or a pharmaceutically acceptable salt thereof together with a leukotriene antagonist.

The invention thus provides, in a further aspect, a combination comprising a compound of formula (I) or a pharmaceutically acceptable salt thereof together with a corticosteroid.

The invention thus provides, in a further aspect, a combination comprising a compound of formula (I) or a pharmaceutically acceptable salt thereof together with a non-steroidal GR agonist.

The invention thus provides, in a further aspect, a combination comprising a compound of formula (I) or a pharmaceutically acceptable salt thereof together with an anticholinergic.

The invention thus provides, in a further aspect, a combination comprising a compound of formula (I) or a pharmaceutically acceptable salt thereof together with an antihistamine.

The invention thus provides, in a further aspect, a combination comprising a compound of formula (I) or a pharmaceutically acceptable salt thereof together with a PDE4 inhibitor and a $\beta_2$-adrenoreceptor agonist.

The invention thus provides, in a further aspect, a combination comprising a compound of formula (I) or a pharmaceutically acceptable salt thereof together with an anticholinergic and a PDE-4 inhibitor.

The invention thus provides, in a further aspect, a combination comprising a compound of formula (I) or a pharmaceutically acceptable salt thereof together with an anti-infective agent.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a compound of formula (I) or a pharmaceutically acceptable salt thereof together with another therapeutically active agent.

The invention thus provides, in a further aspect, a pharmaceutical composition comprising a combination of a compound of formula (I) or a pharmaceutically acceptable salt thereof together with a PDE4 inhibitor.

The invention thus provides, in a further aspect, a pharmaceutical composition comprising a combination of a compound of formula (I) or a pharmaceutically acceptable salt thereof together with a $\beta_2$-adrenoreceptor agonist.

The invention thus provides, in a further aspect, a pharmaceutical composition comprising a combination of a compound of formula (I) or a pharmaceutically acceptable salt thereof together with a leukotriene antagonist.

The invention thus provides, in a further aspect, a pharmaceutical composition comprising a combination of a compound of formula (I) or a pharmaceutically acceptable salt thereof together with a corticosteroid.

The invention thus provides, in a further aspect, a pharmaceutical composition comprising a combination of a compound of formula (I) or a pharmaceutically acceptable salt thereof together with a non-steroidal GR agonist.

The invention thus provides, in a further aspect, a pharmaceutical composition comprising a combination of a compound of formula (I) or a pharmaceutically acceptable salt thereof together with an anticholinergic.

The invention thus provides, in a further aspect, a pharmaceutical composition comprising a combination of a compound of formula (I) or a pharmaceutically acceptable salt thereof together with an antihistamine.

The invention thus provides, in a further aspect, a pharmaceutical composition comprising a combination of a compound of formula (I) or a pharmaceutically acceptable salt thereof together with a PDE4 inhibitor and a $\beta_2$-adrenoreceptor agonist.

The invention thus provides, in a further aspect, a pharmaceutical composition comprising a combination of a compound of formula (I) or a pharmaceutically acceptable salt thereof together with an anticholinergic and a PDE4 inhibitor.

The invention thus provides, in a further aspect, a pharmaceutical composition comprising a combination of a compound of formula (I) or a pharmaceutically acceptable salt thereof together with an anti-infective agent.

The invention will now be illustrated by way of the following non-limiting examples.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

The names of the Examples have been obtained using a compound naming programme which matches structure to name (e.g. ACD/Name Batch v 9.0).

When the name of a commercial supplier is given after the name of a compound or a reagent, this means that the compound is obtainable from a commercial supplier, such as the commercial supplier named. If not referenced herein the compound or reagent can be purchased from a standard supplier such as Sigma Aldrich, Lancaster, Fluorochem, TCI etc.

General Methods
LCMS (Liquid Chromatography Mass Spectroscopy)

LCMS analysis has been carried out using one of the following methods listed below.

LCMS Method A

The UPLC analysis was conducted on an Acquity UPLC CSH C18 column (50 mm×2.1 mm i.d. 1.7 μm packing diameter) at 40° C.

The solvents employed were:

A=0.1% v/v solution of formic acid in water.

B=0.1% v/v solution of formic acid in MeCN.

The gradient employed was:

| Time (min) | Flow (mL/min) | % A | % B |
|---|---|---|---|
| 0 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.

Injection volume: 0.5 μL
MS Conditions
MS: Waters ZQ
Ionisation mode: Alternate-scan Positive and Negative Electrospray
Scan Range: 100 to 1000 AMU
Scan Time: 0.27 s
Inter scan Delay: 0.10 s LCMS Method B The UPLC analysis was conducted on an Acquity UPLC CSH C18 column (50 mm×2.1 mm i.d. 1.7 μm packing diameter) at 40° C.

The solvents employed were:

A=10 mM ammonium bicarbonate in water adjusted to pH 10 with ammonia solution.

B=MeCN.

The gradient employed was:

| Time (min) | Flow (mL/min) | % A | % B |
|---|---|---|---|
| 0 | 1 | 97 | 3 |
| 0.05 | 1 | 97 | 3 |
| 1.50 | 1 | 5 | 95 |
| 1.90 | 1 | 5 | 95 |
| 2.00 | 1 | 97 | 3 |

The UV detection was a summed signal from wavelength of 210 nm to 350 nm.

Injection volume: 0.3 μL
MS Conditions
MS: Waters ZQ
Ionisation mode: Alternate-scan Positive and Negative Electrospray
Scan Range: 100 to 1000 AMU
Scan Time: 0.27 s
Inter scan Delay: 0.10 s LCMS Method C The analytical HPLC was conducted on a X-Select CSH C18 XP column (30 mm×4.6 mm i.d. 2.5 μm packing diameter) at 40° C.

The solvents employed were:

A=0.1% ammonia in water.

B=0.1% ammonia in MeCN.

The gradient employed was:

| Time (min) | Flow (mL/min) | % A | % B |
|---|---|---|---|
| 0 | 1.8 | 95 | 5 |
| 3 | 1.8 | 0 | 100 |
| 4 | 1.8 | 0 | 100 |

The mass spectra (MS) were recorded on a Waters ZQ mass spectrometer using electrospray positive ionisation or electrospray negative ionisation modes.

LCMS Method D

The analytical HPLC was conducted on a X-Select CSH C18 XP column (30 mm×4.6 mm i.d. 2.5 μm packing diameter) at 40° C.

The solvents employed were:

A=0.1% formic acid in water.

B=0.1% formic acid in MeCN.

The gradient employed was:

| Time (min) | Flow (mL/min) | % A | % B |
|---|---|---|---|
| 0 | 1.8 | 95 | 5 |
| 3 | 1.8 | 0 | 100 |
| 4 | 1.8 | 0 | 100 |

The mass spectra (MS) were recorded on a Waters ZQ mass spectrometer using electrospray positive ionisation or electrospray negative ionisation modes.

LCMS Method E

The analytical HPLC was conducted on a X-Select CSH C18 XP column (30 mm×4.6 mm i.d. 2.5 μm packing diameter) at 40° C.

The solvents employed were:

A=0.1% formic acid in water.

B=0.1% formic acid in MeCN.

The gradient employed was:

| Time (min) | Flow (mL/min) | % A | % B |
|---|---|---|---|
| 0 | 1.8 | 100 | 0 |
| 4 | 1.8 | 50 | 50 |

The mass spectra (MS) were recorded on a Waters ZQ mass spectrometer using electrospray positive ionisation or electrospray negative ionisation modes.

LCMS Method F

The analytical HPLC was conducted on a XSelect CSH C18 (150 mm×3.0 mm i.d. 2.5 μm packing diameter) at 35° C.

The solvents employed were:
A=5 mM ammonium bicarbonate in water.
B=MeCN.
The gradient employed was:

| Time (min) | Flow (mL/min) | % A | % B |
|---|---|---|---|
| 0 | 0.7 | 97 | 3 |
| 1 | 0.7 | 97 | 3 |
| 4 | 0.7 | 2 | 98 |
| 7 | 0.7 | 2 | 98 |
| 7.1 | 0.7 | 97 | 3 |
| 8 | 0.7 | 97 | 3 |

UV: 190 nm to 400 nm.
Mass Spectrometry Method:
MS: Agilent SQD—6130 Mass Detector
Ionisation mode: Electrospray Ionisation (ESI)
Polarity Switching: Positive/Negative
Scan range: 100-1000
Step Size: 0.10
Peak width: 0.080 min LCMS Method G The analytical HPLC was conducted on an Acquity BEH C18 (50 mm×2.1 mm i.d. 1.7 μm packing diameter) at 35° C.

The solvents employed were:
A=0.05% formic acid in water.
B=0.05% formic acid in MeCN.
The gradient employed was:

| Time (min) | Flow (mL/min) | % A | % B |
|---|---|---|---|
| 0 | 0.6 | 97 | 3 |
| 0.4 | 0.6 | 97 | 3 |
| 3.2 | 0.6 | 2 | 98 |
| 3.8 | 0.6 | 2 | 98 |
| 4.2 | 0.6 | 97 | 3 |
| 4.5 | 0.6 | 97 | 3 |

UV: 190 nm to 400 nm.
Mass Spectrometry Method:
MS: Waters SQD—3100 Mass Detector
Ionisation mode: Electrospray Ionisation (ESI)
Polarity Switching: Positive/Negative
Scan range: 100-1000 Scan time: 0.5 (secs) Inter scan delay: 0.1 (secs)

LCMS method H

The analytical HPLC was conducted on an Xbridge C18 (50 mm×4.6 mm i.d. 2.5 μm packing diameter) at 35° C.
The solvents employed were:
A=5 mM ammonium bicarbonate in water (pH 10).
B=MeCN.

The gradient employed was:

| Time (min) | Flow (mL/min) | % A | % B |
|---|---|---|---|
| 0 | 1.3 | 95 | 5 |
| 0.5 | 1.3 | 95 | 5 |
| 1.0 | 1.3 | 85 | 15 |
| 6.0 | 1.3 | 2 | 98 |
| 9.0 | 1.3 | 2 | 98 |
| 9.5 | 1.3 | 95 | 5 |
| 10.0 | 1.3 | 95 | 5 |

Mass Spectrometry Method:
MS: Waters TQD—Quattro micro API
Ionisation mode: Electrospray Ionisation (ESI)
Polarity Switching: Positive/Negative
Scan range: 100-1000
Scan time: 0.5 s
Inter scan delay: 0.1 s LCMS Method I The analytical HPLC was conducted on an Acquity BEH C18 (100 mm×2.1 mm i.d. 1.7 μm packing diameter) at 50° C.

The solvents employed were:
A=0.1% TFA in water.
B=0.1% TFA in MeCN.
The gradient employed was:

| Time (min) | Flow (mL/min) | % A | % B |
|---|---|---|---|
| 0 | 0.55 | 97 | 3 |
| 8.5 | 0.55 | 0 | 100 |
| 9 | 0.55 | 0 | 100 |
| 9.5 | 0.55 | 97 | 3 |
| 10.01 | 0.55 | 97 | 3 |

Mass Spectrometry Method:
MS: Waters SQD—3100 Mass Detector
Ionisation mode: Electrospray Ionisation (ESI)
Polarity Switching: Positive/Negative
Scan range: 100-1000
Scan time: 0.5 s
Inter scan delay: 0.1 s Mass Directed Automated Preparative HPLC The methods for the Mass Directed Automated Preparative HPLC used for the purification of compounds are described below:

Mass Directed Automated Preparative HPLC Column, Conditions and Eluent Method A

Column: Xselect CSH C18 column (150 mm×30 mm i.d. 5 μm packing diameter) at ambient temperature.

The solvents employed were:
A=10 mM ammonium bicaronate adjusted to pH 10 with ammonia in water.
B=MeCN.
Injection Volume: 1 mL
The DAD detection was 210 nm to 350 nm.
MS Conditions
MS: Waters ZQ
Ionisation mode: Alternate scan positive/negative Electrospray
Scan Range: 100 to 1000 AMU
Scan Time: 0.50 s
Inter scan Delay: 0.2 s Method B Column: Xselect CSH C18 column (150 mm×30 mm i.d. 5 μm packing diameter) at ambient temperature.

The solvents employed were:
A=0.1% v/v solution of formic acid in water
B=0.1% v/v solution of formic acid in MeCN.
Injection Volume: 1 mL
The DAD detection was 210 nm to 350 nm.
MS Conditions
MS: Waters ZQ
Ionisation mode: Alternate scan positive/negative Electrospray
Scan Range: 100 to 1000 AMU
Scan Time: 0.50 s
Inter scan Delay: 0.2 s Method C
Column: Xselect CSH C18 column (150 mm×30 mm i.d. 5 μm packing diameter) at ambient temperature.
The solvents employed were:
A=10 mM ammonium bicaronate in water adjusted to pH 10 with ammonia.
B=MeCN.
Injection Volume: 3 mL
The UV detection was for a signal wavelength at 254 nm.
MS Conditions
MS: Waters ZQ
Ionisation mode: Alternate scan positive/negative Electrospray
Scan Range: 100 to 1000 AMU
Scan Time: 0.50 s
Inter scan Delay: 0.2 s Preparative HPLC Column, Conditions and Eluent
The methods for the Preparative HPLC used for the purification of compounds are described below:

Method A:
Column: Kromosil Phenyl C18 (150 mm×25 mm, 10 μm packing diameter).
Mobile Phase A: 10 mM ammonium bicarbonate (aqueous).
Mobile Phase B: MeCN.
The gradient employed was:

| Time (min) | Flow (mL/min) | % A | % B |
| --- | --- | --- | --- |
| 0 | 25 | 100 | 0 |
| 10 | 25 | 90 | 10 |
| 12 | 25 | 88 | 12 |
| 12.5 | 25 | 87.5 | 12.5 |
| 15 | 25 | 85 | 15 |
| 15.5 | 25 | 84.5 | 15.5 |

Method B:
Column: Kromo Phenyl hexyl (150 mm×30 mm, 5 μm packing diameter).
Mobile Phase A: 10 mM ammonium bicarbonate (aqueous).
Mobile Phase B: MeCN.
The column was eluted with 35% of solvent B at a flow rate of 25 mL/min.

Method C:
Column: Xbridge C18 (250 mm×30 mm, 5 μm packing diameter).
Mobile Phase A: 10 mM ammonium bicarbonate (aqueous)
Mobile Phase B: MeCN:MeOH.
The gradient employed was:

| Time (min) | Flow (mL/min) | % A | % B |
| --- | --- | --- | --- |
| 0 | 25 | 80 | 20 |
| 1 | 25 | 80 | 20 |
| 8 | 25 | 45 | 55 |
| 14 | 25 | 45 | 55 |
| 14.1 | 25 | 0 | 100 |
| 20 | 25 | 0 | 100 |
| 20.1 | 25 | 80 | 20 |
| 25 | 25 | 80 | 20 |

Method D:
Column: Sunfire C18 (250 mm×30 mm, 5 μm packing diameter).
Mobile Phase A: 10 mM ammonium bicarbonate (aqueous).
Mobile Phase B: MeCN.
The gradient employed was:

| Time (min) | Flow (mL/min) | % A | % B |
| --- | --- | --- | --- |
| 0 | 30 | 40 | 60 |
| 12 | 30 | 40 | 60 |
| 12.1 | 30 | 0 | 100 |
| 15 | 30 | 0 | 100 |
| 15.1 | 30 | 40 | 60 |
| 18 | 30 | 40 | 60 |

Method E:
Column: Xbridge C18 (150 mm×19 mm, 5 μm packing diameter).
Mobile Phase A: 0.1% formic acid in water.
Mobile Phase B: MeCN.
The gradient employed was:

| Time (min) | Flow (mL/min) | % A | % B |
| --- | --- | --- | --- |
| 0 | 15 | 90 | 10 |
| 1 | 15 | 90 | 10 |
| 10 | 15 | 65 | 35 |
| 10.1 | 15 | 0 | 100 |
| 13.5 | 15 | 0 | 100 |
| 13.6 | 15 | 90 | 10 |
| 16 | 15 | 90 | 10 |

Method F:
Column: Xbridge C18 (150 mm×19 mm, 5 μm packing diameter).
Mobile Phase A: 10 mM ammonium bicarbonate (aqueous)
Mobile Phase B: MeCN.
The gradient employed was:

| Time (min) | Flow (mL/min) | % A | % B |
| --- | --- | --- | --- |
| 0 | 19 | 90 | 10 |
| 10 | 19 | 70 | 30 |
| 12 | 19 | 70 | 30 |
| 12.1 | 19 | 0 | 100 |
| 15 | 19 | 0 | 100 |
| 15.1 | 19 | 90 | 10 |
| 20 | 19 | 90 | 10 |

Method G:
Column: Kinetex Phenyl hexyl (150 mm×30 mm, 10 μm packing diameter).
Mobile Phase A: 10 mM ammonium bicarbonate (aqueous).
Mobile Phase B: MeCN.

The gradient employed was:

| Time (min) | Flow (mL/min) | % A | % B |
|---|---|---|---|
| 0 | 30 | 90 | 10 |
| 1 | 30 | 90 | 10 |
| 10.8 | 30 | 65 | 45 |
| 11.1 | 30 | 0 | 100 |
| 12.5 | 30 | 0 | 100 |
| 13 | 30 | 90 | 10 |
| 15 | 30 | 90 | 10 |

Method H:
Column: Sunfire C18 (250 mm×30 mm, 10 μm packing diameter).
Mobile Phase A: 10 mM ammonium bicarbonate (aqueous).
Mobile Phase B: MeCN.
The gradient employed was:

| Time (min) | Flow (mL/min) | % A | % B |
|---|---|---|---|
| 0 | 30 | 75 | 25 |
| 18 | 30 | 75 | 25 |
| 18.1 | 30 | 0 | 100 |
| 21 | 30 | 0 | 100 |
| 21.1 | 30 | 75 | 25 |
| 24 | 30 | 75 | 25 |

Method I:
Column: Xbridge C18 (250 mm×30 mm, 10 μm packing diameter).
Mobile Phase A: 10 mM ammonium bicarbonate (aqueous).
Mobile Phase B: MeCN.
The gradient employed was:

| Time (min) | Flow (mL/min) | % A | % B |
|---|---|---|---|
| 0 | 30 | 90 | 10 |
| 10 | 30 | 50 | 50 |
| 10.1 | 30 | 0 | 100 |
| 13 | 30 | 0 | 100 |
| 13.1 | 30 | 90 | 10 |
| 16 | 30 | 90 | 10 |

Method J:
Column: Kinetex C-8 (150 mm×30 mm, 10 μm packing diameter).
Mobile Phase A: 10 mM ammonium bicarbonate (aqueous).
Mobile Phase B: MeCN.
The gradient employed was:

| Time (min) | Flow (mL/min) | % A | % B |
|---|---|---|---|
| 0 | 30 | 90 | 10 |
| 1 | 30 | 90 | 10 |
| 10 | 30 | 50 | 50 |
| 10.1 | 30 | 0 | 100 |
| 14 | 30 | 0 | 100 |
| 14.1 | 30 | 90 | 10 |

Method K:
Column: Phenomenex LUNA C18 (250 mm×21.2 mm, 5 μm packing diameter).
Mobile Phase A: 10 mM ammonium bicarbonate (aqueous).
Mobile Phase B: MeCN.

The gradient employed was:

| Time (min) | Flow (mL/min) | % A | % B |
|---|---|---|---|
| 0 | 20 | 80 | 20 |
| 10 | 20 | 50 | 50 |
| 11.3 | 20 | 50 | 50 |
| 11.5 | 20 | 0 | 100 |
| 16 | 20 | 0 | 100 |
| 16.3 | 20 | 80 | 20 |
| 18 | 20 | 80 | 20 |

INTERMEDIATES AND EXAMPLES

Intermediate 1

N-(2-Bromopyridin-4-yl)-2,5-dichloropyridine-3-sulfonamide

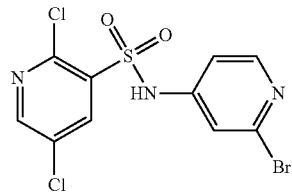 [SMILES: O=S(=O)(Nc1ccnc(Br)c1)c1cc(Cl)cnc1Cl]

To a solution of 2-bromopyridin-4-amine (75 g, 433 mmol) in pyridine (750 mL) stirred under nitrogen at 0° C. was added 2,5-dichloropyridine-3-sulfonyl chloride (128 g, 520 mmol) portionwise. The reaction mixture was stirred at room temperature for 16 h. After this time, pyridine was evaporated under reduced pressure to obtain a crude residue which was poured into ice water. The resulting solid was collected by filtration and dried. The solid was dissolved in EtOAc (2 L) and the organic layer was washed with 10% EDTA solution (2 L). The organic phase was dried over $Na_2SO_4$, filtered and concentrated under reduced pressure to afford the title compound (120 g) as a brown solid.
LCMS (Method G) $R_t$=2.16 min, $[M+H]^+$=381.9/383.9/385.9.

Intermediate 2

N-(2-Bromopyridin-4-yl)-5-chloro-2-methoxypyridine-3-sulfonamide

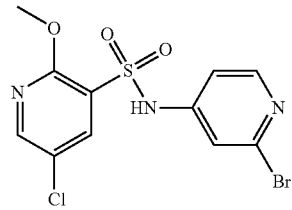 [SMILES: COc1ncc(Cl)cc1S(=O)(=O)Nc1ccnc(Br)c1]

Sodium methoxide solution (30% w/w, 600 mL, 157 mmol) was added dropwise to solid N-(2-bromopyridin-4-yl)-2,5-dichloropyridine-3-sulfonamide (60 g, 157 mmol) stirring under nitrogen at room temperature. The reaction mixture was then stirred at 80° C. for 1 h, then cooled to 0° C. and quenched with 20% citric acid solution (2 L). The resultant solid was collected by filtration and dried to afford the title compound (50 g) as a brown solid.

LCMS (Method G) R$_t$=2.31 min, [M+H]$^+$=377.9/379.9

Intermediate 3

1-(3-Fluoro-4-(4,4,5,5-tetramethyl-1,3,2-dioxaborolan-2-yl)benzyl)-4-isopropylpiperazine

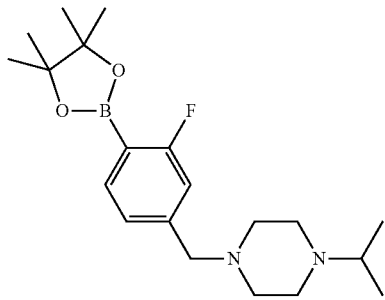 [SMILES: CC(C)N1CCN(Cc2ccc(B3OC(C)(C)C(C)(C)O3)c(F)c2)CC1]

Method A

To a solution of 4-bromo-3-fluorobenzaldehyde (100 g, 493 mmol), 4,4,4',4',5,5,5',5'-octamethyl-2,2'-bi(1,3,2-dioxaborolane) (150 g, 591 mmol) in 1,4-dioxane (1000 mL) was added potassium acetate (121 g, 1231 mmol). The reaction mixture was degassed with argon for 30 min then PdCl$_2$(dppf)-CH$_2$Cl$_2$ adduct (20.11 g, 24.63 mmol) was added. The resulting reaction mixture was stirred at 100° C. for 3 h. The reaction mixture was allowed to cool to room temperature, then filtered through celite and washed with 10% MeOH/DCM (2 L). The filtrate was concentrated under reduced pressure to afford a crude residue (140 g) as a black liquid. The above crude compound (140 g), sodium sulfate (80 g, 560 mmol) and 1-isopropylpiperazine (0.042 L, 280 mmol) in DCM (1.5 L) were stirred for 30 min, then sodium triacetoxyborohydride (178 g, 840 mmol) was added and the resulting mixture was stirred at room temperature for 4 h. The reaction mixture was diluted with DCM (3 L) and quenched with aqueous NaHCO$_3$ solution (3 L). The organic layer was separated, washed with water (2 L), dried over anhydrous Na$_2$SO$_4$, filtered and the filtrate was concentrated under reduced pressure to obtain a crude residue (180 g) as a brown liquid. The crude compound (180 g) was pre-adsorbed onto Florisil (250 g, 100-200 mesh) and purified by normal phase column chromatography on Florisil (100-200 mesh, 2.5 kg) eluting with hexane initially, then 5% MeOH in DCM. The desired fractions were combined and concentrated under reduced pressure to afford the title compound (150 g) as a light yellow liquid.

$^1$H NMR (400 MHz, DMSO-d$_6$) δ (ppm) 7.56-7.61 (m, 1H), 7.13 (d, J=7.7 Hz, 1H), 7.04 (d, J=10.3 Hz, 1H), 3.46 (s, 2H), 2.54-2.63 (m, 1H), 2.29-2.46 (m, 8H), 1.29 (s, 12H), 0.94 (d, J=6.58 Hz, 6H).

Method B

Charge 4-bromo-3-fluorobenzaldehyde (150.0 g), 4,4,4',4',5,5,5',5'-octamethyl-2,2'-bi(1,3,2-dioxaborolane) (205.7 g) and 1,4-dioxane (1.5 L) into a reaction vessel, charge KOAc (181.6 g) into the reaction vessel, degas the reaction vessel with N$_2$ three times, add Pd(dppf)Cl$_2$ (27.1 g) into the reaction vessel, adjust the reaction vessel to 90-100° C., stir the reaction vessel at 90-100° C. for 2 hrs. Check the reaction with TLC till the disappearance of 4-bromo-3-fluorobenzaldehyde (Mobile phase: 10% Ethyl acetate in n-heptane, Rf=0.6). Cool the reaction mixture to 20~25° C. then switch the solvent to ethyl acetate (1.5 L), filter the mixture through celite (150.0 g), wash the filtrate with water (300 ml×3), combine the organic phase and concentrate under reduced pressure to give the title compound (243.3 g) as black oil. The crude product was used for next step directly.

Charge 3-fluoro-4-(4,4,5,5-tetramethyl-1,3,2-dioxaborolan-2-yl)benzaldehyde (243.3 g), 1-isopropylpiperazine (103.9 g) and DCM (2.4 L) into a reaction vessel, stir the reaction mixture at 20-30° C. for 15-30 min, charge NaBH (OAc)$_3$ (410.5 g) into the reaction vessel. Adjust the reaction vessel to 20-30° C., stir the reaction vessel at 20-30° C. for 2 hrs. Switch the reaction solvent to ethyl acetate and wash with 5% aq. NaHCO$_3$ solution. Separate the organic phase and concentrate under reduced pressure to give the title compound (210 g, 78%th for two steps) as brown oil.

Method C

4-Bromo-3-fluorobenzaldehyde (18.8 kg, 92.6 mol) was dissolved in 2-methyltetrahydrofuran (86 kg) at ca. 20° C. Potassium acetate (23 kg) and 4,4,4',4',5,5,5',5'-octamethyl-2,2'-bi(1,3,2-dioxaborolane) (28.5 kg) were added in sequence and the reaction was stirred for 1 h at ca. 25° C. Nitrogen was bubbled through the mixture for 3 h at ca. 25° C. before [1,1'-Bis(diphenylphosphino)ferrocene]dichloropalladium(II) (0.7 kg) was added. Nitrogen was bubbled through the mixture for a further 3 h before the mixture was stirred for 7 h at ca. 80° C. The temperature was reduced to 25° C. and water (95 kg) was added. After stirring for 3 h the aqueous layer was discarded. The organic layer was concentrated to 18.8-37.6 L under reduced pressure while maintaining the temperature below 45° C. 2-Methyltetrahydrofuran (136 kg) was added in two portions during the concentration step. After completion of the concentration step, additional 2-methyltetrahydrofuran (86 kg) was added.

1-Isopropylpiperazine (13.7 kg) was added to the mixture over 3 h at ca. 25° C., before the mixture was stirred for 1 h. Sodium triacetoxyborohydride (50.8 kg) was added in portions and the reaction mixture was stirred for 4.5 h at ca. 28° C. Water (61 kg) was added over 5 h at ca. 28° C. and the resulting mixture was stirred for 2 h. 30% aqueous sodium hydroxide solution (54 kg) was added until the pH reached 7.0. The aqueous layer was discarded, before the organic layer was washed with an aqueous solution of 5% sodium bicarbonate and 10% sodium chloride (76 kg). Finally, 151.8 kg of a solution of the title compound (31.1 kg) in 2-methyltetrahydrofuran was obtained in 93% th yield.

Intermediate 4

5-Chloro-N-(2-(2-fluoro-4-((4-isopropylpiperazin-1-yl)methyl)phenyl)pyridin-4-yl)-2-methoxypyridine-3-sulfonamide A mixture of N-(2-bromopyridin-4-yl)-5-chloro-2-methoxypyridine-3-sulfonamide (35 g, 92 mmol), 1-(3- fluoro-4-(4,4,5,5-tetra methyl-1,3,2-dioxaborolan-2-yl)benzyl)-4-isopropylpiperazine (crude) (56.9 g, 157 mmol) and Na$_2$CO$_3$ (39.2 g, 370 mmol) in isopropanol (300 mL)/water (150 mL) was degassed using argon for 20 min and PdCl$_2$ (dppf)-CH$_2$Cl$_2$ adduct (3.77 g, 4.62 mmol) was then added. The reaction mixture was again degassed for 30 min under an argon atmosphere and then stirred under argon at 90° C. for 3 h. The reaction mixture was filtered through celite and the celite bed was washed with 10% MeOH in DCM (2×200 mL). The filtrate was concentrated under reduced pressure to obtain a crude residue which was acidified to pH 1-2 with 1M HCl (100 mL) and washed with EtOAc (2×500 mL). The mixture was stirred for 10 min and the organic layer was separated. The aqueous phase was adjusted to pH 8-9 using 25% ammonia solution in water and the product was extracted with 10% MeOH in DCM (2×1000 mL). All organic extracts were combined, dried over anhydrous Na$_2$SO$_4$ and filtered. The filtrate was concentrated under reduced pressure to afford the title compound (17.5 g) as a white solid.

LCMS (Method I) R$_t$=2.77 min, [M+H]$^+$=534.3

Intermediate 5

N-(2-(4-((4-(tert-Butyl)piperazin-1-yl)methyl)-2-fluorophenyl)pyridin-4-yl)-5-chloro-2-methoxypyridine-3-sulfonamide

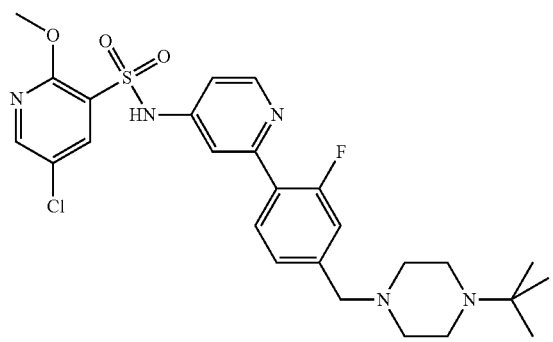 [SMILES: COc1ncc(Cl)cc1S(=O)(=O)Nc1ccnc(-c2ccc(CN3CCN(C(C)(C)C)CC3)cc2F)c1]

A vial was charged with N-(2-bromopyridin-4-yl)-5-chloro-2-methoxypyridine-3-sulfonamide (2230 mg, 5.89 mmol), (4-((4-(tert-butyl)piperazin-1-yl)methyl)-2-fluorophenyl)boronic acid (2600 mg, 8.84 mmol), sodium carbonate (2498 mg, 23.57 mmol) and PdCl$_2$(dppf) (431 mg, 0.589 mmol) in water (15 mL) and EtOH (15 mL). The vial was sealed and the reaction mixture was heated thermally at reflux for 30 min. The reaction mixture was filtered on celite and the celite pad was washed with MeOH. The filtrate was concentrated under reduced pressure. The residue was dissolved in 4:1 water (with an ammonium bicarbonate modifier adjusted to pH 10):MeOH (25 mL) and eluted on a reverse-phase C18 silica gel column using a gradient of 5% to 55% MeCN (containing 0.1% NH$_3$) in water (with an ammonium bicarbonate modifier adjusted to pH 10). The desired fractions were concentrated under reduced pressure to afford the title compound (3060 mg) as a yellow-brown solid.

LCMS (Method B) Rt=0.81 min, [M+H]$^+$=548.1.

Intermediate 6

(4-((4-(tert-Butyl)piperazin-1-yl)methyl)-2-fluorophenyl)boronic acid

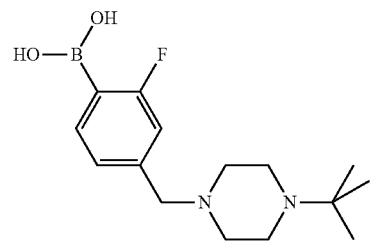 [SMILES: CC(C)(C)N1CCN(Cc2ccc(B(O)O)c(F)c2)CC1]

(2-Fluoro-4-formylphenyl)boronic acid (4996 mg, 29.8 mmol) and 1-(tert-butyl)piperazine (4232 mg, 29.8 mmol) in DCM (70 mL) were stirred for 30 min before addition of sodium triacetoxyborohydride (7584 mg, 35.8 mmol). The resulting solution was stirred for 18 h. The reaction was heated to 40° C. and stirred with molecular sieves for 1 h. Sodium triacetoxyborohydride (7584 mg, 35.8 mmol) was added and the mixture was stirred for a further 21 h. The reaction mixture was then concentrated under reduced pressure and eluted on a reverse-phase C18 silica gel column using a gradient of 0% to 20% MeCN (containing 0.1% NH$_3$) in water (with an ammonium bicarbonate modifier adjusted to pH 10). The desired fractions were concentrated under reduced pressure to afford the title compound (5243 mg) as a yellow solid.

LCMS (Method B) R$_t$=0.64 min, [M+H]$^+$=295.4.

Intermediate 7

5-Chloro-N-(2-(4-((4-isopropylpiperazin-1-yl)methyl)phenyl)pyridin-4-yl)-2-methoxypyridine-3-sulfonamide

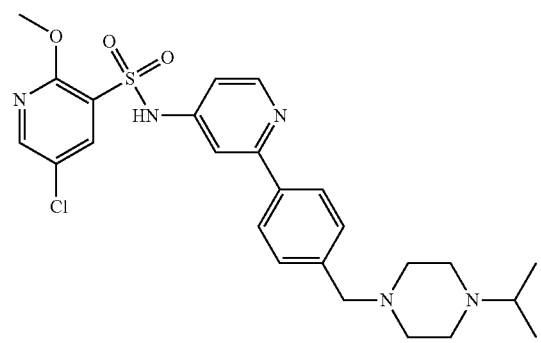

N-(2-Bromopyridin-4-yl)-5-chloro-2-methoxypyridine-3-sulfonamide (390 mg, 1.030 mmol), 1-isopropyl-4-(4-(4,4,5,5-tetramethyl-1,3,2-dioxaborolan-2-yl)benzyl)piperazine (709 mg, 2.060 mmol) and 2'-(dimethylamino)-2-biphenyl-palladium(II)-chloride dinorbornylphosphine complex (57.7 mg, 0.103 mmol) and tripotassium phosphate (656 mg, 3.09 mmol) were added to a microwave vial and dissolved in EtOH (7 ml) and water (3 mL). The reaction vessel was sealed and heated in a Biotage Initiator to 130° C. for 10 min. The reaction mixture was filtered through celite, washed with MeOH and concentrated in vacuo. The residues were dissolved in 1:1 MeOH:DMSO and purified by Mass Directed Automated Preparative HPLC (Method C). The solvent was evaporated in vacuo and the product further dried under a stream of nitrogen in the Radleys blowdown apparatus to afford the title compound (255 mg).

LCMS (Method B) $R_t$=0.77 min, $[M+H]^+$=516.5.

Intermediate 8

1-Isopropyl-4-(4-(4,4,5,5-tetramethyl-1,3,2-dioxaborolan-2-yl)benzyl)piperazine

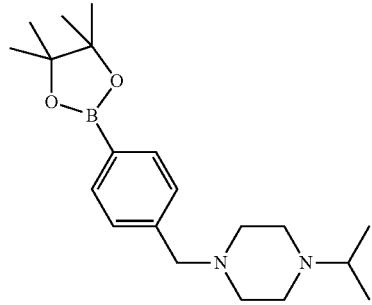 [SMILES: CC(C)N1CCN(Cc2ccc(B3OC(C)(C)C(C)(C)O3)cc2)CC1]

To a suspension of 2-(4-(bromomethyl)phenyl)-4,4,5,5-tetramethyl-1,3,2-dioxaborolane (2 g, 6.73 mmol) and potassium carbonate (1.210 g, 8.75 mmol) in DMF (20 mL) stirred at room temperature was added 1-isopropylpiperazine (1.349 mL, 9.43 mmol) dropwise. The reaction mixture was heated to 80° C. After 1 h, the reaction was cooled and concentrated in vacuo. The reaction mixture was dissolved in EtOAc (100 mL), washed with water (100 mL), the organic phase separated and the aqueous phase re-extracted with EtOAc (2×100 mL). The organic phases were combined, dried using a hydrophobic frit and evaporated in vacuo to afford the title compound (2.525 g) as an orange/brown oil.

LCMS (Method A) $R_t$=0.62 min, $[M+H]^+$=345.2.

Intermediate 9

5-Chloro-N-(2-(4-((dimethylamino)methyl)phenyl)pyridin-4-yl)-2-methoxypyridine-3-sulfonamide

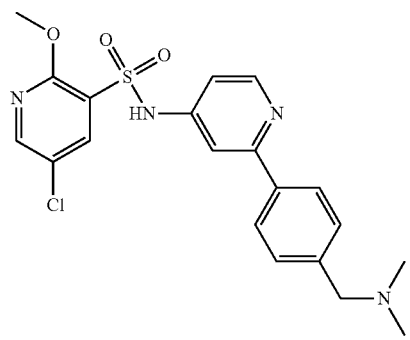 [SMILES: COc1ncc(Cl)cc1S(=O)(=O)Nc1ccnc(-c2ccc(CN(C)C)cc2)c1]

N-(2-Bromopyridin-4-yl)-5-chloro-2-methoxpyridine-3-sulfonamide (665 mg, 1.229 mmol), N,N-dimethyl-1-(4-(4,4,5,5-tetramethyl-1,3,2-dioxaborolan-2-yl)phenyl)methanamine (642 mg, 2.459 mmol), tripotassium phosphate (783 mg, 3.69 mmol) and 2'-(dimethylamino)-2-biphenyl-palladium(II)-chloride dinorbornylphosphine complex (34.5 mg, 0.061 mmol) were added to a microwave vial and dissolved in EtOH (7 mL) and water (3 mL). The reaction vessel was sealed and heated in a Biotage Initiator to 130° C. for 30 min. The reaction was cooled and the reaction mixture was filtered through celite, washed with MeOH and concentrated in vacuo. The residue was dissolved in 1:1 MeOH:DMSO and purified by Mass Directed Automated Preparative HPLC (Method C). The solvent was evaporated in vacuo and the product further dried under a stream of nitrogen in the Radleys blowdown apparatus to afford the title compound (104 mg).

LCMS (Method B) $R_t$=0.73 min, $[M+H]^+$=433.4.

Intermediate 10

N,N-Dimethyl-1-(4-(4,4,5,5-tetramethyl-1,3,2-dioxaborolan-2-yl)phenyl)methanamine

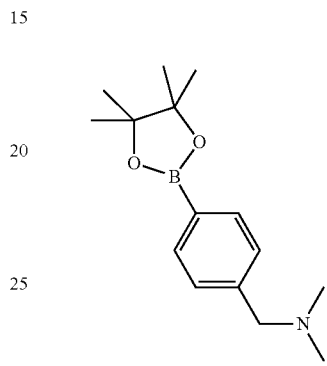

Dimethylamine hydrochloride (11.83 g, 145 mmol) and potassium carbonate (27.9 g, 202 mmol) were stirred together in acetone (250 mL) at room temperature for 10 min. A solution of 2-(4-(bromomethyl)phenyl)-4,4,5,5-tetramethyl-1,3,2-dioxaborolane (5 g, 16.84 mmol) in acetone (50 mL) was added dropwise to the reaction mixture over 20 min, and the reaction mixture was left to stir for 66 h at room temperature. The solvent was removed in vacuo and the residue was diluted with water (60 mL) and extracted with EtOAc (5×100 mL). The organic layers were combined, dried using a hyrdrophobic frit and the solvent was removed in vacuo to afford the title compound (2.89 g).

LCMS (Method B) $R_t$=1.25 min, $[M+H]^+$=262.5.

Intermediate 11

5-Chloro-N-(2-(3-fluoro-4-((4-isopropylpiperazin-1-yl)methyl)phenyl)pyridin-4-yl)-2-methoxypyridine-3-sulfonamide

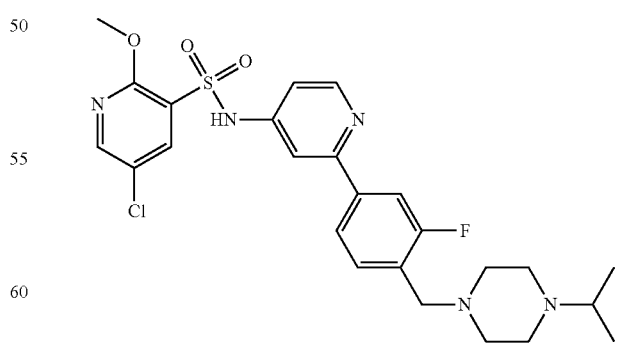

A vial was charged with N-(2-bromopyridin-4-yl)-5-chloro-2-methoxypyridine-3-sulfonamide (0.98 g, 2.59 mmol), (3-fluoro-4-((4-isopropylpiperazin-1-yl)methyl)phenyl)boronic acid (2.33 g, 4.16 mmol), tripotassium phosphate (1.06 g, 4.99 mmol) and XPhos Palladacycle (0.19 g, 0.257 mmol) in 4:1 EtOH:water (12.5 mL). The reaction vessel was sealed and heated thermally to 130° C. overnight. The reaction was stopped, the reaction mixture filtered through celite, washed with MeOH (60 mL) and the solvent removed in vacuo. The residue was loaded in DMSO and purified by reverse phase (C18) column chromatography eluting with a gradient of 0 to 40% MeCN (containing 0.1% NH₃) in water (with an ammonium bicarbonate modifier adjusted to pH 10). The appropriate fractions were combined and evaporated in vacuo to afford the title compound (598 mg) as an off-white solid.

LCMS (Method A) $R_t$=0.59 min, [M+H]⁺=534.4.

Intermediate 12

(3-Fluoro-4-((4-isopropylpiperazin-1-yl)methyl)phenyl)boronic acid

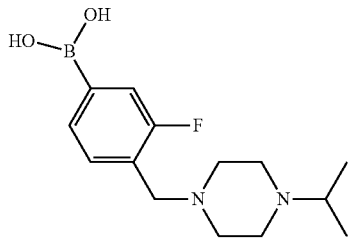 [SMILES: CC(C)N1CCN(Cc2ccc(B(O)O)cc2F)CC1]

To a suspension of 3-fluoro-4-formylphenyl)boronic acid (1.05 g, 6.25 mmol) in DCM (20 mL) was added 1-isopropylpiperazine (0.92 mL, 6.43 mmol) and the resulting solution was left to stir for 1 h, at which time sodium triacetoxyborohydride (2.01 g, 9.48 mmol) was added portionwise over 5 min. The mixture was left to stir for 4 h then concentrated in vacuo to afford the title product (3.91 g) as a yellow gum.

LCMS (Method B) Rt=0.66 min, [M+H]+=281.4.

Intermediate 13

N-(2-(4-((4-(tert-Butyl)piperazin-1-yl)methyl)phenyl)pyridin-4-yl)-5-chloro-2-methoxypyridine-3-sulfonamide

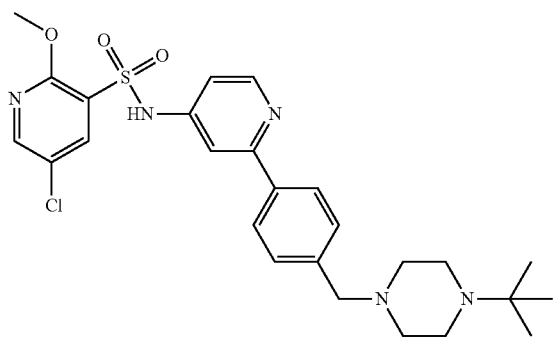 [SMILES: COc1ncc(Cl)cc1S(=O)(=O)Nc1ccnc(-c2ccc(CN3CCN(C(C)(C)C)CC3)cc2)c1]

A microwave vial was charged with N-(2-bromopyridin-4-yl)-5-chloro-2-methoxypyridine-3-sulfonamide (340 mg, 0.898 mmol), 1-(tert-butyl)-4-(4-(4,4,5,5-tetramethyl-1,3,2-dioxaborolan-2-yl)benzyl)piperazine (482 mg, 1.345 mmol), PdCl₂(dppf) (66 mg, 0.090 mmol), Na₂CO₃ (295 mg, 2.78 mmol), 1,4-dioxane (4 mL) and water (1 mL). The vial was sealed and the reaction mixture was heated at 100° C. for 30 min in the Biotage microwave system. The reaction mixture was filtered on celite and the celite pad was washed with MeOH. The filtrate was concentrated under reduced pressure. The residue was dissolved in 1:4 DCM:MeOH (~5 mL) and loaded onto a samplet, which was dried under high vacuum for 1 h. The samplet was then loaded onto a C18 reverse-phase silica cartridge and eluted with a gradient of 15% to 55% MeCN (containing 0.1% NH3) in water (with an ammonium bicarbonate modifier adjusted to pH 10). Collected fractions were concentrated under reduced pressure to afford the title compound (360 mg) as a brown solid.

LCMS (Method B) Rt=0.80 min, [M+H]⁺=530.3.

Intermediate 14

1-(tert-Butyl)-4-(4-(4,4,5,5-tetramethyl-1,3,2-dioxaborolan-2-yl)benzyl)piperazine

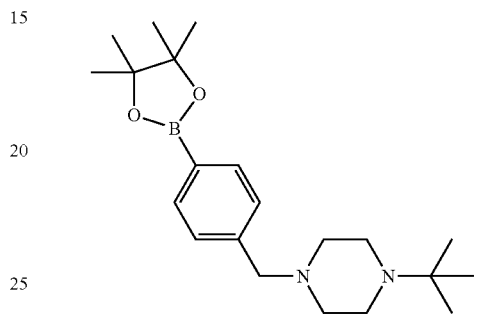

A mixture of 2-(4-(bromomethyl)phenyl)-4,4,5,5-tetramethyl-1,3,2-dioxaborolane (0.5 g, 1.684 mmol) and sodium carbonate (0.232 g, 2.189 mmol) in acetone (4 mL) was treated dropwise with a solution of 1-(tert-butyl)piperazine (0.239 g, 1.684 mmol) in acetone (1 mL). The reaction mixture was stirred for 24 h. The reaction mixture was concentrated under reduced pressure, and partitioned between 2:1 saturated NaCl solution:water (30 mL) and EtOAc (50 mL). The organic layer was separated and the aqueous layer was further extracted with EtOAc (50 mL). The organic layers were combined, dried using a hydrophobic frit and concentrated under reduced pressure to afford the title compound (482 mg) as a pale yellow oil that solidified overnight.

¹H NMR (400 MHz, DMSO-d₆) δ (ppm) 7.62 (d, J=8.0 Hz, 2H), 7.29 (d, J=8.0 Hz, 2H), 3.44 (s, 2H), 2.49 (br. s, 4H), 2.34 (br. s., 4H), 1.27-1.30 (m, 12H), 0.98 (s, 9H).

Intermediate 15

5-Chloro-N-(2-(4-((4-cyclobutylpiperazin-1-yl)methyl)phenyl)pyridin-4-yl)-2-methoxypyridine-3-sulfonamide

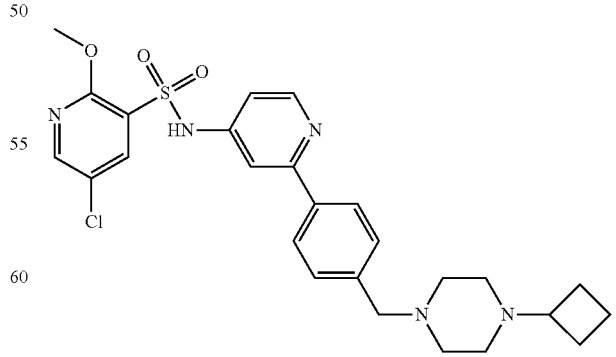

A microwave vial was charged with N-(2-bromopyridin-4-yl)-5-chloro-2-methoxypyridine-3-sulfonamide (267 mg, 0.705 mmol), 1-cyclobutyl-4-(4-(4,4,5,5-tetramethyl-1,3,2-dioxaborolan-2-yl)benzyl)piperazine (377 mg, 1.058 mmol), PdCl₂(dppf) (52 mg, 0.071 mmol), Na₂CO₃ (233 mg, 2.198 mmol), 1,4-dioxane (4 mL) and water (1 mL). The vial was sealed and the reaction mixture was heated at 100° C. for 30 min in the biotage microwave system. The reaction mixture was filtered on celite and the celite pad was washed with MeOH. The filtrate was concentrated under reduced pressure and the residue was dissolved in 1:4 DCM:MeOH (~5 mL), loaded onto a samplet, which was dried under high vacuum for 1 h. The samplet was then loaded onto a C18 reverse-phase silica cartridge and eluted with a gradient of 15% to 55% MeCN (containing 0.1% NH₃) in water (with an ammonium bicarbonate modifier adjusted to pH 10). Collected fractions were concentrated under reduced pressure to afford the title compound (207 mg) as a brown solid.

LCMS (Method B) $R_f$=0.83 min, [M+H]⁺=528.3.

Intermediate 16

1-Cyclobutyl-4-(4-(4,4,5,5-tetramethyl-1,3,2-dioxaborolan-2-yl)benzyl)piperazine

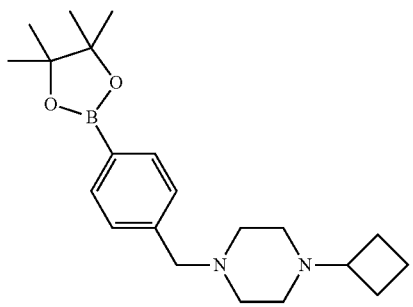 [SMILES: CC1(C)OB(c2ccc(CN3CCN(C4CCC4)CC3)cc2)OC1(C)C]

A mixture of 2-(4-(bromomethyl)phenyl)-4,4,5,5-tetramethyl-1,3,2-dioxaborolane (0.5 g, 1.684 mmol) and sodium carbonate (0.589 g, 5.56 mmol) in acetone (4 mL) was treated dropwise with a solution of 1-cyclobutylpiperazine, dihydrochloride (0.359 g, 1.684 mmol) in acetone (1 mL). The reaction mixture was stirred for 2 h. The reaction mixture was concentrated under reduced pressure and partitioned between 2:1 saturated NaCl solution:water (50 mL) and EtOAc (60 mL). The aqueous layer was further extracted with EtOAc (50 mL). The organic layers were combined, dried using a hydrophobic frit and concentrated under reduced pressure to afford the title compound (377 mg) as an off-white solid.

¹H NMR (400 MHz, DMSO-d₆) δ (ppm) 7.62 (d, J=8.1 Hz, 2H), 7.29 (d, J=8.1 Hz, 2H), 3.46 (s, 2H), 2.61-2.73 (m, 1H), 2.11-2.45 (m, 8H), 1.87-1.97 (m, 2H), 1.67-1.81 (m, 2H), 1.56-1.66 (m, 2H), 1.28 (s, 12H).

Intermediate 17

5-Chloro-N-(2-(2,6-difluoro-4-((4-isopropylpiperazin-1-yl)methyl)phenyl)pyridin-4-yl)-2-methoxypyridine-3-sulfonamide

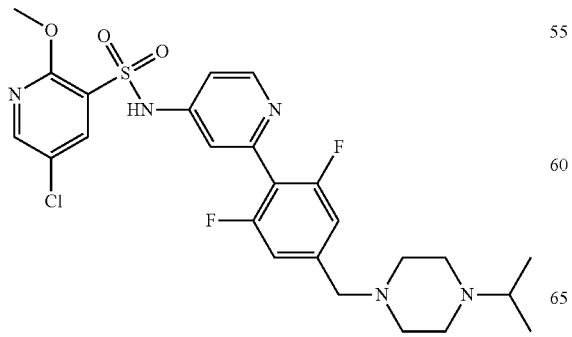

A microwave vial was charged with N-(2-bromopyridin-4-yl)-5-chloro-2-methoxpyridine-3-sulfonamide (200 mg, 0.528 mmol), 1-(3,5-difluoro-4-(4,4,5,5-tetramethyl-1,3,2-dioxaborolan-2-yl)benzyl)-4-isopropylpiperazine (300 mg, 0.789 mmol), PdCl₂(dppf) (40 mg, 0.055 mmol), Na₂CO₃ (192 mg, 1.812 mmol), 1,4-dioxane (4 mL) and water (1 mL). The vial was sealed and the reaction mixture was heated at 100° C. for 30 min in a biotage microwave system. Another portion of PdCl₂(dppf) (40 mg, 0.055 mmol) was added, the vial was sealed and the reaction mixture was heated at 130° C. for 45 min in a biotage microwave system. Further portions of PdCl₂(dppf) (40 mg, 0.055 mmol) and 1-(3,5-difluoro-4-(4,4,5,5-tetra methyl-1,3,2-dioxaborolan-2-yl)benzyl)-4-isopropyl piperazine (200 mg) were added, the vial was sealed and the reaction mixture was heated at 150° C. for 2 h in a biotage microwave system. The reaction mixture was filtered through celite and washed with MeOH. The filtrate was concentrated under reduced pressure. The residue was purified by C18 reverse-phase silica chromatography eluting with a gradient of 5% to 85% MeCN (containing 0.1% formic acid) in water (containing 0.1% formic acid). The desired fractions were concentrated under reduced pressure to afford the crude product (37 mg, probably formic acid form) as a yellow glass.

The reaction was repeated to obtain more material: a microwave vial was charged with N-(2-bromopyridin-4-yl)-5-chloro-2-methoxypyridine-3-sulfonamide (200 mg, 0.528 mmol), 1-(3,5-difluoro-4-(4,4,5,5-tetra methyl-1,3,2-dioxaborolan-2-yl)benzyl)-4-isopropylpiperazine (300 mg, 0.789 mmol), PdCl₂(dppf) (40 mg, 0.055 mmol), Na₂CO₃ (192 mg, 1.812 mmol), 1,4-dioxane (4 mL) and water (1 mL). The vial was sealed and the reaction mixture was heated at 150° C. for 120 min in a biotage microwave system. The reaction mixture was filtered on celite and washed with MeOH. The filtrate was concentrated under reduced pressure. The residues was purified by C18 reverse-phase silica chromatography eluting with a gradient of 5% to 85% MeCN (containing 0.1% formic acid) in water (containing 0.1% formic acid). The desired fractions were concentrated under reduced pressure to afford the crude product (54 mg, probably formic acid salt).

The combined crude products were purified by chromatography on reverse phase C18 silica eluting with a gradient of 5% to 85% MeCN (containing 0.1% NH₃) in water (with an ammonium bicarbonate modifier adjusted to pH 10) to afford, after concentration of the desired fractions under reduced pressure, the title compound (75 mg) as an off-white solid.

LCMS (Method A) Rt=0.63 min, [M+H]⁺=552.4.

Intermediate 18

1-(3,5-Difluoro-4-(4,4,5,5-tetramethyl-1,3,2-dioxaborolan-2-yl)benzyl)-4-isopropylpiperazine

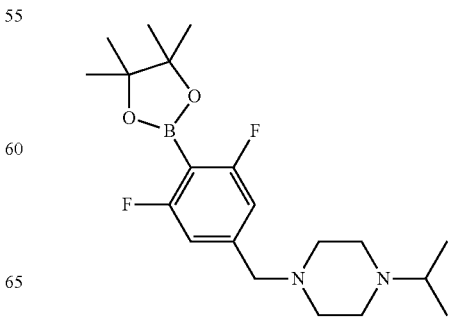

3,5-Difluoro-4-(4,4,5,5-tetramethyl-1,3,2-dioxaborolan-2-yl)benzaldehyde (1 g, 3.73 mmol) and 1-isopropylpiperazine (0.534 mL, 3.73 mmol) were stirred in DCM (20 mL) and acetic acid (0.200 mL) for 10 min at room temperature. Sodium triacetoxyborohydride (1.186 g, 5.60 mmol) was added and the reaction mixture was stirred for 72 h at room temperature under an atmosphere of nitrogen. The solvent was removed in vacuo and the residue was diluted with water (30 mL) and basified to pH 14 using 2M NaOH solution. The aqueous phase was extracted with DCM (3×30 mL). The organic layers were combined, dried using a hydrophobic frit and the solvent was removed in vacuo. The residue was attempted to be triturated with DCM (30 mL) but no precipitate was formed. The solvent was removed in vacuo to afford the title compound (1.220 g) as a light yellow oil.

$^1$H NMR (400 MHz, CDCl$_3$) δ (ppm) 6.86 (d, J=8.3 Hz, 2H), 3.46 (s, 2H), 2.61-2.71 (m, 1H), 2.41-2.60 (m, 8H), 1.38 (s, 12H), 1.05 (d, J=6.6 Hz, 6H).

Intermediate 19

N-(2-(4-((4-(sec-Butyl)piperazin-1-yl)methypphenyl)pyridin-4-yl)-5-chloro-2-methoxypyridine-3-sulfonamide

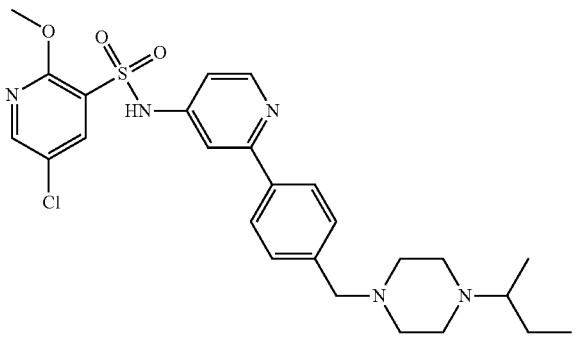 [SMILES: CCC(C)N1CCN(Cc2ccc(-c3cc(NS(=O)(=O)c4cc(Cl)cnc4OC)ccn3)cc2)CC1]

1-(sec-Butyl)-4-(4-(4,4,5,5-tetramethyl-1,3,2-dioxaborolan-2-yl)benzyl)piperazine (885 mg, 2.469 mmol), N-(2-bromopyridin-4-yl)-5-chloro-2-methoxypyridine-3-sulfonamide (850 mg, 2.245 mmol), Xphos palladacycle (166 mg, 0.224 mmol) and sodium carbonate (952 mg, 8.98 mmol) were added to a microwave vial followed by EtOH (6 mL) and water (2 mL). The vial was sealed and heated to 100° C. for 30 min in a microwave apparatus. The reaction mixture was then concentrated in vacuo and partitioned between EtOAc (200 mL) and saturated aqueous sodium hydrogen carbonate (200 mL), the aqueous phase was separated and extracted with further EtOAc (200 mL). The combined organic fractions were then passed through a hydrophobic frit and concentrated in vacuo to give an orange gum. The residue (dissolved in DMSO (~3 mL)) was purified by chromatography on reverse phase C18 silica eluting with a gradient of 5% to 45% MeCN (containing 0.1% NH$_3$) in water (with an ammonium bicarbonate modifier adjusted to pH 10) to afford, after concentration of the desired fractions under reduced pressure, the title compound (591 mg).

LCMS (Method B) R$_t$=0.90 min, [M+H]$^+$=530.4.

Intermediate 20

1-(sec-Butyl)-4-(4-(4,4,5,5-tetramethyl-1,3,2-dioxaborolan-2-yl)benzyl)piperazine

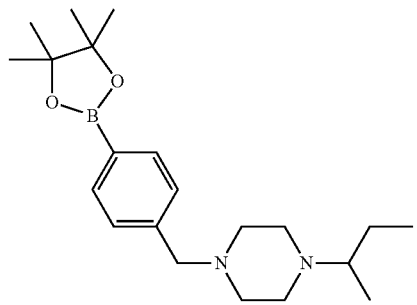 [SMILES: CCC(C)N1CCN(Cc2ccc(B3OC(C)(C)C(C)(C)O3)cc2)CC1]

1-(sec-Butyl)piperazine (available from Fluorochem, 620 µL, 4.20 mmol) was dissolved in acetone (20 mL), potassium carbonate (1.117 g, 8.08 mmol) was added and the reaction mixture stirred at room temperature for 10 min. 2-(4-(Bromomethyl)phenyl)-4,4,5,5-tetramethyl-1,3,2-dioxaborolane (1.2 g, 4.04 mmol) in acetone (20 mL) was added dropwise and the reaction mixture continued to stir at room temperature for a further 90 min. The reaction mixture was then concentrated in vacuo and partitioned between EtOAc (100 mL) and aqueous NaCl (100 mL), the aqueous phase was separated, extracted with further EtOAc (100 mL), the combined organic extracts were dried using a hydrophobic frit and concentrated in vacuo to afford the title compound (1.715 g, used crude in the next reaction).

LCMS (Method B) R$_t$=1.49 min, [M+H]$^+$=359.3, 65% a/a, and R$_t$=0.82 min, [M+H]$^+$=277.1, 32% a/a, corresponding to the parent boronic acid (believed to be formed in the LCMS by hydrolysis).

Intermediate 21

5-Chloro-N-(2-(2-fluoro-4-(pyrrolidin-1-ylmethyl)phenyl)pyridin-4-yl)-2-methoxypyridine-3-sulfonamide

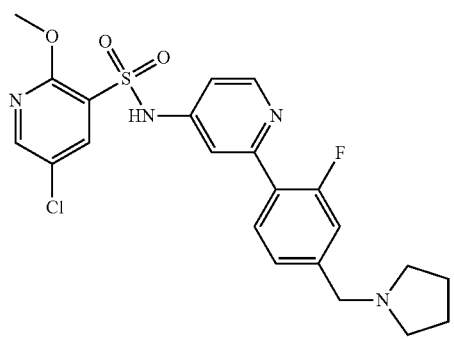 [SMILES: COc1ncc(Cl)cc1S(=O)(=O)Nc1ccnc(-c2ccc(CN3CCCC3)cc2F)c1]

N-(2-Bromopyridin-4-yl)-5-chloro-2-methoxpyridine-3-sulfonamide (153 mg, 0.404 mmol), (2-fluoro-4-(pyrrolidin-1-ylmethyl)phenyl)boronic acid (117 mg, 0.525 mmol), sodium carbonate (168 mg, 1.585 mmol) and Xphos palladacycle (30 mg, 0.041 mmol) were added to a microwave vial followed by EtOH (3 mL) and water (1 mL). The vial was sealed and heated in a biotage microwave to 100° C. for 30 min. Further portions of (2-fluoro-4-(pyrrolidin-1-ylmethyl)phenyl)boronic acid (117 mg, 0.525 mmol) and Xphos palladacycle (30 mg, 0.041 mmol) were added and the reaction mixture heated in the microwave at 100° C. for 45 min. The reaction mixture was concentrated in vacuo and purified by chromatography on reverse phase C18 silica eluting with a gradient of 20% to 40% MeCN (containing 0.1% $NH_3$) in water (with an ammonium bicarbonate modifier adjusted to pH 10). The appropriate fractions were combined and concentrated in vacuo to afford the title compound (102 mg) as a colourless gum.

LCMS (Method A) $R_t$=0.55 min, $[M+H]^+$=477.3.

Intermediate 22

(2-Fluoro-4-(pyrrolidin-1-ylmethyl)phenyl)boronic acid

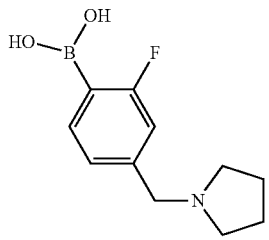 [SMILES: OB(O)c1ccc(CN2CCCC2)cc1F]

To a suspension of (2-fluoro-4-formylphenyl)boronic acid (3.3 g, 19.65 mmol) in DCM (50 mL) was added at room temperature pyrrolidine (1.640 mL, 19.65 mmol). Sodium triacetoxyborohydride (5.00 g, 23.58 mmol) was then added and the mixture stirred at room temperature for 18 h. The crude product was filtered on a small pad of silica, eluting with DCM-MeOH (85:1). The filtrate was evaporated to dryness to afford the title compound (1.1 g) as a yellow oil.

LCMS (Method C) $R_t$=1.04 min, $[M+H]^+$=224.2.

Intermediate 23

5-Chloro-N-(2-(3-fluoro-4-(pyrrolidin-1-ylmethyl)phenyl)pyridin-4-yl)-2-methoxypyridine-3-sulfonamide

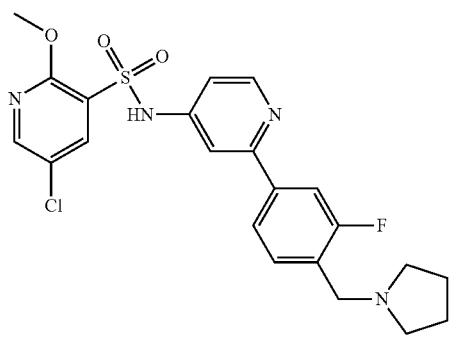 [SMILES: COc1ncc(Cl)cc1S(=O)(=O)Nc1ccnc(-c2ccc(CN3CCCC3)c(F)c2)c1]

1-(2-Fluoro-4-(4,4,5,5-tetramethyl-1,3,2-dioxaborolan-2-yl)benzyl)pyrrolidine (184 mg, 0.602 mmol), N-(2-bromopyridin-4-yl)-5-chloro-2-methoxypyridine-3-sulfonamide (152 mg, 0.401 mmol), sodium carbonate (172 mg, 1.623 mmol) and $PdCl_2$(dppf) (42 mg, 0.051 mmol) were added to a microwave vial followed by dioxane (4 mL) and water (1 mL). The vial was sealed and heated in a biotage microwave to 100° C. for 30 min. Another portion of N-(2-bromopyridin-4-yl)-5-chloro-2-methoxypyridine-3-sulfonamide (60 mg, 0.158 mmol) was added and the vial was sealed and heated in a biotage microwave to 100° C. for 15 min. The reaction mixture was concentrated in vacuo and purified by chromatography on reverse phase C18 silica eluting with a gradient of 20% to 40% MeCN (containing 0.1% $NH_3$) in water (with an ammonium bicarbonate modifier adjusted to pH 10). The appropriate fractions were combined and concentrated in vacuo to afford the title compound (84 mg) as a colourless gum.

LCMS (Method A) $R_t$=0.58 min, $[M+H]^+$=477.3.

Intermediate 24

1-(2-Fluoro-4-(4,4,5,5-tetramethyl-1,3,2-dioxaborolan-2-yl)benzyl)pyrrolidine

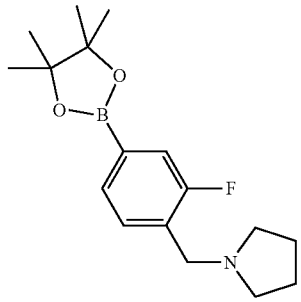 [SMILES: CC1(C)OB(c2ccc(CN3CCCC3)c(F)c2)OC1(C)C]

1-(4-Bromo-2-fluorobenzyl)pyrrolidine (3.4 g, 13.17 mmol), 4,4,4',4',5,5,5',5'-octamethyl-2,2'-bi(1,3,2-dioxaborolane) (3.68 g, 14.49 mmol), potassium acetate (2.6 g, 26.5 mmol) and $PdCl_2$(dppf) (0.080 g, 0.109 mmol) were sealed within a microwave vial. 1,4-Dioxane (20 mL) was added and the reaction mixture was evacuated and purged 5 times with nitrogen. The reaction mixture was heated to 100° C. under an atmosphere of nitrogen for 6 h. The reaction mixture was allowed to reach room temperature. Water was added and the product was extracted with DCM (3×100 mL). The organic phase was dried over $Na_2SO_4$, filtered and evaporated to dryness. The product was purified by chromatography on silica eluting with a gradient of 0 to 5% MeOH in DCM. The appropriate fractions were combined and concentrated in vacuo. Trituration of the residue in pentane afforded the title compound (800 mg) as a cream powder.

LCMS (Method D) $R_t$=1.64 min, $[M+H]^+$=306.3.

Intermediate 25

1-(4-Bromo-2-fluorobenzyl)pyrrolidine

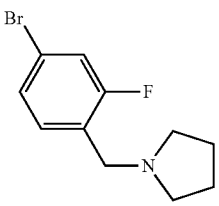 [SMILES: Fc1cc(Br)ccc1CN1CCCC1]

Pyrrolidine (1.4 g, 19.68 mmol) and potassium carbonate (5.16 g, 37.3 mmol) were mixed in acetone (100 mL) and the mixture was stirred at room temperature for 15 min. A solution of 4-bromo-1-(bromomethyl)-2-fluorobenzene (4 g, 14.93 mmol) in acetone (25 mL) was added dropwise over 20 min. The mixture was stirred at room temperature for 1 h. The solvent was removed in vacuo, poured into water (300 mL), and the product was extracted with DCM (2×100 mL). The organic phase was dried over $Na_2SO_4$, filtered off and evaporated to dryness. The residue was purified by silica chromatography eluting with a gradient 0 to 5% MeOH in DCM. The appropriate fractions were combined and concentrated in vacuo to afford the title compound (3.4 g) as a yellow oil.

LCMS (Method D) Rt=0.96 min, $[M+H]^+$=258.0/260.0.

Intermediate 26

5-Chloro-N-(2-(3,5-difluoro-4-((4-isopropylpiperazin-1-yl)methyl)phenyl)pyridin-4-yl)-2-methoxypyridine-3-sulfonamide

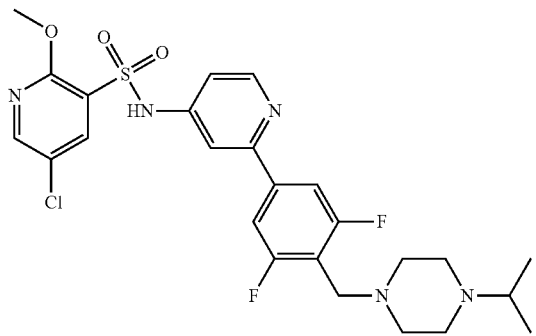

N-(2-Bromopyridin-4-yl)-5-chloro-2-methoxypyridine-3-sulfonamide (150 mg, 0.396 mmol), (3,5-difluoro-4-((4-isopropylpiperazin-1-yl)methyl)phenyl)boronic acid (154 mg, 0.515 mmol), sodium carbonate (168 mg, 1.585 mmol) and Xphos palladacycle (29 mg, 0.039 mmol) were added to a microwave vial followed by EtOH (3 mL) and water (1 mL). The vial was sealed and heated in a biotage microwave to 100° C. for 30 min. Additional portions of (3,5-difluoro-4-((4-isopropylpiperazin-1-yl)methyl)phenyl)boronic acid (154 mg, 0.515 mmol), Xphos palladacycle (29 mg, 0.039 mmol) and EtOH (3 mL) were added. The vial was sealed and heated in a biotage microwave 100° C. for 30 min. The reaction mixture was then concentrated in vacuo and purified by reverse phase C18 silica chromatography eluting with a gradient of 25% to 45% MeCN (containing 0.1% $NH_3$) in water (with an ammonium bicarbonate modifier adjusted to pH 10). The appropriate fractions were combined and concentrated in vacuo to afford the title compound (102 mg) as a white solid.

LCMS (Method A) $R_t$=0.66 min, $[M+H]^+$=552.5.

Intermediate 27

(3,5-Difluoro-4-((4-isopropylpiperazin-1-yl)methyl)phenyl)boronic acid

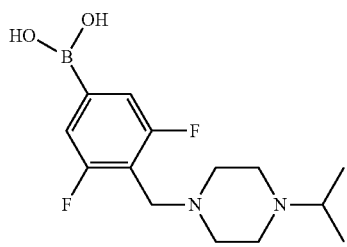 [SMILES: CC(C)N1CCN(Cc2c(F)cc(B(O)O)cc2F)CC1]

To a suspension of (3,5-difluoro-4-formylphenyl)boronic acid (3 g, 16.14 mmol) in DCM (50 mL) was added at room temperature 1-isopropylpiperazine (2.069 g, 16.14 mmol). Sodium triacetoxyborohydride (4.10 g, 19.36 mmol) was then added and the mixture stirred at room temperature for 18 h. The reaction mixture was filtered on a small pad of silica, eluting with DCM-MeOH (85:15). The solvent was evaporated to dryness to afford the title compound (1.4 g) as a yellow oil.

LCMS (Method E) Rt=1.35 min, $[M+H]^+$=299.1.

Intermediate 28

5-Chloro-2-methoxy-N-(2-(4-((4-(oxetan-3-yl)piperazin-1-yl)methyl)phenyl)pyridin-4-yl)pyridine-3-sulfonamide

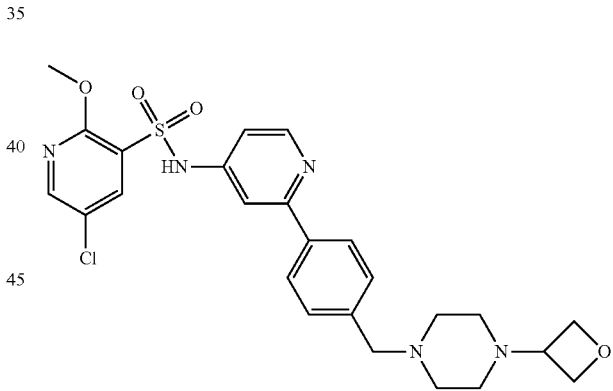

A microwave vial was charged with N-(2-bromopyridin-4-yl)-5-chloro-2-methoxypyridine-3-sulfonamide (98 mg, 0.259 mmol), 1-(oxetan-3-yl)-4-(4-(4,4,5,5-tetramethyl-1,3,2-dioxa borolan-2-yl)benzyl)piperazine (138 mg, 0.385 mmol), PdCl2(dppf) (20 mg, 0.027 mmol) and sodium carbonate (119 mg, 1.123 mmol) in 4:1 1,4-dioxane:water (1.25 mL). The reaction vessel was sealed and heated in a Biotage Initiator Microwave to 130° C. for 30 min. After cooling, the reaction mixture was filtered through celite, the solid washed with MeOH (40 mL) and the filtrate concentrated in vacuo. The residue was dissolved in 1:1 MeOH:DMSO (2×1 mL) and purified by Mass Directed Automated Preparative HPLC (Method A). The solvent was evaporated in vacuo to afford the title compound (89 mg) as a white solid.

LCMS (Method A) Rt=0.52 min, $[M+H]^+$=530.4.

Intermediate 29

1-(Oxetan-3-yl)-4-(4-(4,4,5,5-tetramethyl-1,3,2-dioxaborolan-2-yl)benzyl)piperazine

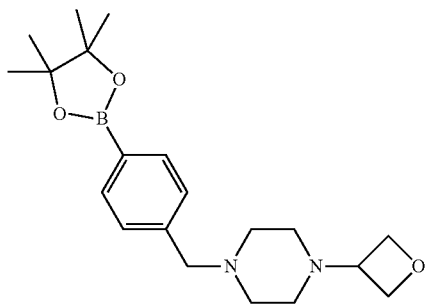 [SMILES: CC1(C)OB(c2ccc(CN3CCN(C4COC4)CC3)cc2)OC1(C)C]

To a stirred solution of 1-(oxetan-3-yl)piperazine (152 mg, 1.069 mmol) in acetone (5 mL) was added potassium carbonate (265 mg, 1.917 mmol) and the mixture left for 15 min when 2-(4-(bromomethyl)phenyl)-4,4,5,5-tetramethyl-1,3,2-dioxaborolane (200 mg, 0.673 mmol) was added. After 2 h, the reaction was stopped, the solvent removed in vacuo, the mixture redissolved in EtOAc (20 mL), partitioned with water (20 mL) and basified to pH 9 with aqueous sodium hydrogen carbonate. The organic layer was isolated, the aqueous was re-extracted with EtOAc (20 mL), the organics were combined, filtered using a hydrophobic frit and the solvent removed in vacuo to afford the title compound (219 mg) as a white solid.

$^1$H NMR (400 MHz, DMSO-$d_6$) δ (ppm) 7.62 (d, J=8.0 Hz, 2H), 7.30 (d, J=8.0 Hz, 2H), 4.50 (t, J=6.3 Hz, 2H), 4.40 (t, J=6.3 Hz, 2H), 3.48 (s, 2H), 3.34-3.42 (m, 1H), 2.16-2.45 (m, 8H), 1.29 (s, 12H).

Intermediate 30

5-Chloro-N-(2-(2,3-difluoro-4-((4-isopropylpiperazin-1-yl)methyl)phenyl)pyridin-4-yl)-2-methoxypyridine-3-sulfonamide

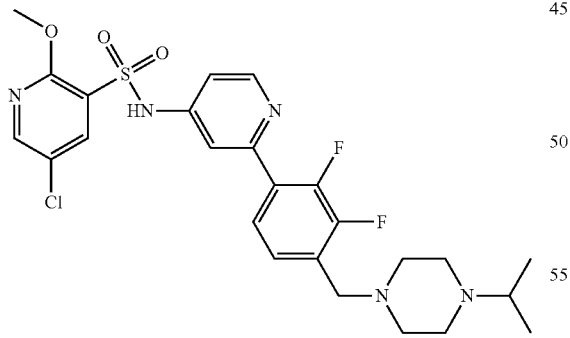

(2,3-Difluoro-4-((4-isopropylpiperazin-1-yl)methyl)phenyl)boronic acid (409 mg, 1.372 mmol), N-(2-bromopyridin-4-yl)-5-chloro-2-methoxypyridine-3-sulfonamide (525 mg, 1.387 mmol), sodium carbonate (419 mg, 3.95 mmol) and Xphos palladacycle (101 mg, 0.137 mmol) were added to a microwave vial followed by EtOH (3 mL) and water (1 mL). The vial was sealed and heated in a microwave at 100° C. for 1 h. MeOH (20 mL) was added and the solution was filtered through celite followed by elution with MeOH (20 mL). The solvent was evaporated in vacuo and the residue purified by reverse phase C18 silica chromatography eluting with a gradient of 20% to 55% MeCN (containing 0.1% NH$_3$) in water (with an ammonium bicarbonate modifier adjusted to pH 10). The appropriate fractions were combined and concentrated in vacuo to afford the title compound (359 mg) as a pale yellow gum.

LCMS (Method B) R$_t$=0.81 min, [M+H]$^+$=552.5.

Intermediate 31

(2,3-Difluoro-4-((4-isopropylpiperazin-1-yl)methyl)phenyl)boronic acid

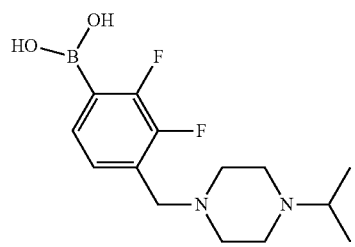 [SMILES: CC(C)N1CCN(Cc2ccc(B(O)O)c(F)c2F)CC1]

1-(4-Bromo-2,3-difluorobenzyl)-4-isopropylpiperazine (804 mg, 2.413 mmol), 4,4,4',4',5,5,5',5'-octamethyl-2,2'-bi (1,3,2-dioxaborolane) (735 mg, 2.90 mmol), potassium acetate (592 mg, 6.03 mmol), PdCl2(dppf) (88 mg, 0.121 mmol) and 1,4-dioxane (4 mL) were added to a microwave vial. The vial was sealed heated in the microwave instrument to 100° C. for 3 h. MeOH (10 mL) was added and the reaction mixture was filtered through celite and washed with MeOH (30 mL). The solvent was evaporated and the residue purified by reverse phase C18 silica chromatography eluting with a gradient of 5% to 60% MeCN (containing 0.1% NH$_3$) in water (with an ammonium bicarbonate modifier adjusted to pH 10). The appropriate fractions were combined and concentrated in vacuo to afford the title compound (409 mg) as a yellow oil.

$^1$H NMR (400 MHz, CDCl$_3$) includes δ (ppm) 7.38-7.48 (m, 1H), 7.10-7.21 (m, 1H), 3.64 (t, J=1.7 Hz, 2H), 2.63-2.71 (m, 1H), 2.56 (br. s., 8H), 1.06 (dd, J=1.1, 6.5 Hz, 6H).

Intermediate 32

1-(4-Bromo-2,3-difluorobenzyl)-4-isopropylpiperazine

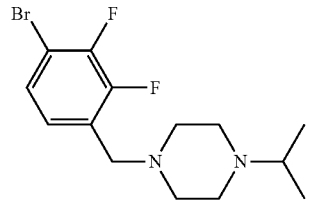 [SMILES: CC(C)N1CCN(Cc2ccc(Br)c(F)c2F)CC1]

1-Isopropylpiperazine (0.65 mL, 4.54 mmol) and 4-bromo-2,3-difluorobenzaldehyde (1 g, 4.52 mmol) were dissolved in DCM (10 mL) and stired in air at room temperature for 15 min. Sodium triacetoxyborohydride (1.439 g, 6.79 mmol) was added and the reaction was stirred for 2 h. The reaction mixture was left to stand over the weekend. Saturated aqueous sodium hydrogen carbonate (20 mL) was then added and the aqueous phase was separared and extracted with DCM (3×20 mL).

The combined organic solutions were dried over sodium sulfate, filtered and concentrated in vacuo. The crude product was purified by reverse phase C18 silica chromatography eluting with a gradient of 40% to 95% MeCN (containing 0.1% NH3) in water (with an ammonium bicarbonate modifier adjusted to pH 10). The appropriate fractions were combined and concentrated in vacuo to afford the title compound (804 mg) as a pale yellow oil.

LCMS (Method A) $R_t$=0.59 min, $[M+H]^+$=333.3/335.3.

Intermediate 33

5-Chloro-N-(2-(2-fluoro-4-((4-(oxetan-3-yl)piperazin-1-yl)methyl)phenyl)pyridin-4-yl)-2-methoxypyrid ine-3-sulfonamide

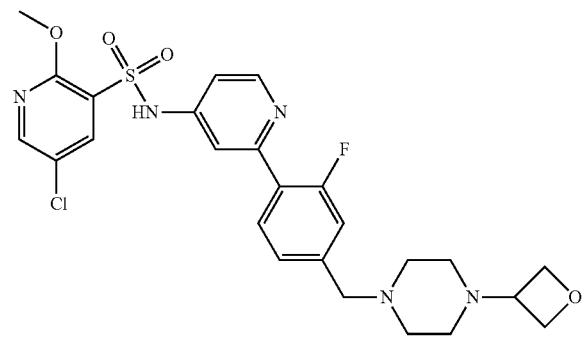 [SMILES: COc1ncc(Cl)cc1S(=O)(=O)Nc1ccnc(-c2ccc(CN3CCN(C4COC4)CC3)cc2F)c1]

To a stirred solution of 5-chloro-N-(2-(2-fluoro-4-formylphenyl)pyridin-4-yl)-2-methoxpyridine-3-sulfonamide (102 mg, 0.242 mmol) in DCM (3 mL) was added 1-(oxetan-3-yl)piperazine (42 mg, 0.295 mmol) in DCM (2 mL) and 3 drops of acetic acid. The reaction was left to stir for 1 h, when sodium triacetoxyborohydride (84 mg, 0.396 mmol) was added in one portion. After 4 h, the solvent was removed in vacuo and the residue was dissolved in 1:1 MeOH:DMSO (2×1 mL) and purified by Mass Directed Automated Preparative HPLC (Method A). The solvent was dried under a stream of nitrogen in the Radleys blowdown apparatus to afford the title compound (68 mg) as a white solid.

LCMS (Method A) $R_t$=0.54 min, $[M+H]^+$=548.4.

Intermediate 34

5-Chloro-N-(2-(2-fluoro-4-formylphenyl)pyridin-4-yl)-2-methoxypyridine-3-sulfonamide

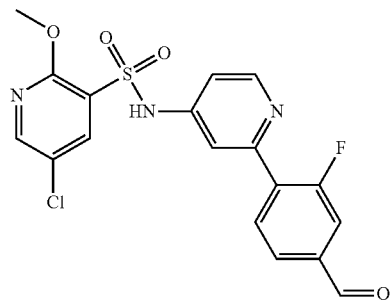 [SMILES: COc1ncc(Cl)cc1S(=O)(=O)Nc1ccnc(-c2ccc(C=O)cc2F)c1]

A microwave vial was equipped with N-(2-bromopyridin-4-yl)-5-chloro-2-methoxypyridine-3-sulfonamide (500 mg, 1.321 mmol), (2-fluoro-4-formylphenyl)boronic acid (444 mg, 2.64 mmol), tripotassium phosphate (841 mg, 3.96 mmol) and 2'-(dimethylamino)-2-biphenylyl-palladium(II) chloride dinorbornylphosphine complex (74.0 mg, 0.132 mmol) in 3:1 EtOH:water (1.3 mL). The reaction vessel was sealed and heated in a Biotage Initiator Microwave to 120° C. for 20 min. After cooling the reaction, the reaction mixture was filtered through celite, washed through with MeOH (20 mL) and the solvent removed in vacuo to afford the crude product as a brown oil. The sample was preabsorbed on florosil and purified by silica chromatography eluting with a gradient of 0 to 10% MeOH in DCM. The appropriate fractions were combined and evaporated in vacuo to afford the title compound (331 mg) as a yellow solid.

LCMS (Method A) $R_t$=0.98 min, $[M+H]^+$=422.3.

Intermediate 35

5-Chloro-N-(2-(4-((4-cyclobutylpiperazin-1-yl)methyl)-2-fluorophenyl)pyridin-4-yl)-2-methoxypyridine-3-sulfonamide

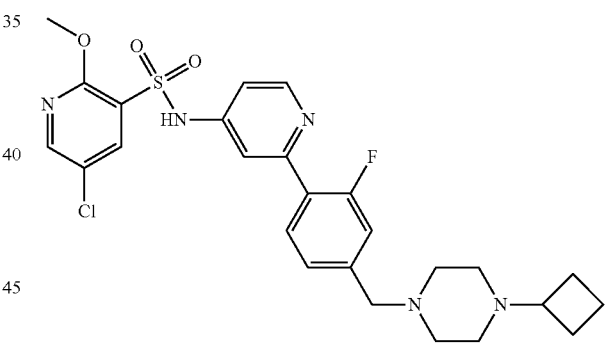

To a stirred solution of 5-chloro-N-(2-(2-fluoro-4-formylphenyl)pyridin-4-yl)-2-methoxypyridine-3-sulfonamide (103 mg, 0.244 mmol) in DCM (3 mL) was added 1-cyclobutylpiperazine dihydrochloride (available from Key Organics, 60 mg, 0.281 mmol) in DCM (2 mL) and 3 drops of acetic acid. The reaction was left to stir for 1 h, when sodium triacetoxyborohydride (85 mg, 0.401 mmol) was added in one portion. After 4 h, an additional portion of 1-cyclobutylpiperazine dihydrochloride (60 mg, 0.281 mmol) was added and the reaction was left to stir overnight. The solvent was removed in vacuo. The residue was dissolved in 1:1 MeOH:DMSO (2×1 mL) and purified by Mass Directed Automated Preparative HPLC (Method A). The solvent was evaporated in vacuo to afford the title compound (61 mg) as an off-white solid.

LCMS (Method A) $R_t$=0.60 min, $[M+H]^+$=546.3.

Intermediate 36

5-Chloro-N-(2-(2,5-difluoro-4-((4-isopropylpiperazin-1-yl)methyl)phenyl)pyridin-4-yl)-2-methoxypyridine-3-sulfonamide

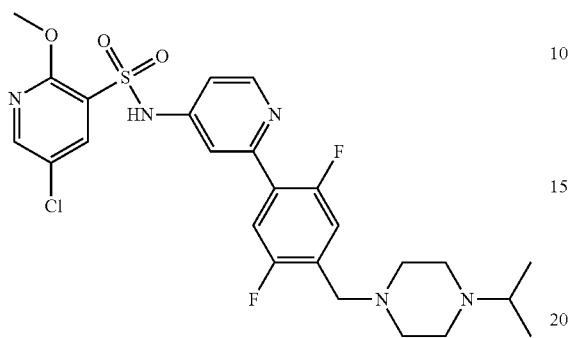 [SMILES: COc1ncc(Cl)cc1S(=O)(=O)Nc1ccnc(-c2ccc(CN3CCN(C4CCC4)CC3)cc2F)c1]

N-(2-Bromopyridin-4-yl)-5-chloro-2-methoxpyridine-3-sulfonamide (450 mg, 1.188 mmol), sodium carbonate (520 mg, 4.91 mmol), PdCl$_2$(dppf) (89 mg, 0.122 mmol) and 1-(2,5-difluoro-4-(4,4,5,5-tetramethyl-1,3,2-dioxaborolan-2-yl)benzyl)-4-isopropylpiperazine (615 mg, 1.617 mmol) were suspended in EtOH (3 mL) and water (3 mL). The reaction mixture was heated at 100° C. under an atmosphere of nitrogen for 1 h. The reaction mixture was cooled to room temperature and was directly purified by chromatography on reverse phase C18 silica eluting with a gradient of 5% to 60% MeCN (containing 0.1% NH$_3$) in water (with an ammonium bicarbonate modifier adjusted to pH 10). The desired fractions were concentrated under reduced pressure to afford the title compound (519 mg) as an off-white solid.

LCMS (Method A) R$_t$=0.63 min, [M+H]$^+$=552.2.

Intermediate 37

1-(2,5-Difluoro-4-(4,4,5,5-tetramethyl-1,3,2-dioxaborolan-2-yl)benzyl)-4-isopropylpiperazine

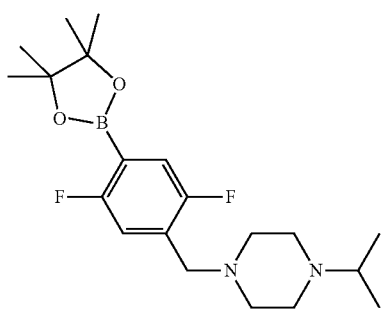 [SMILES: CC(C)N1CCN(Cc2cc(F)c(B3OC(C)(C)C(C)(C)O3)cc2F)CC1]

1-(4-Bromo-2,5-difluorobenzyl)-4-isopropylpiperazine (1.38 g, 4.14 mmol), 4,4,4',4',5,5,5',5'-octamethyl-2,2'-bi(1,3,2-dioxaborolane) (1.23 g, 4.84 mmol), PdCl$_2$(dppf) (0.152 g, 0.207 mmol), potassium acetate (1.02 g, 10.39 mmol) and 1,4-dioxane (8 mL) were added to a microwave vial. The vial was sealed heated thermally to 100° C. for 3 h. The reaction mixture was cooled to room temperature and was filtered through a pad of celite, washing the celite with MeOH (2×10 mL). The filtrate was concentrated under reduced pressure and the residue purified by chromatography on reverse phase (C18 silica) eluting with a gradient of 0 to 50% MeCN (containing 0.1% NH3) in water (with an ammonium bicarbonate modifier adjusted to pH 10) to afford, after concentration of the desired fractions under reduced pressure, the title compound (620 mg) as a yellow oil.

$^1$H NMR (400 MHz, CDCl3) δ (ppm) 7.32-7.39 (m, 1H), 7.07-7.15 (m, 1H), 3.57 (s, 2H), 2.63-2.71 (m, 1H), 2.56 (br. s., 8H), 1.36 (s, 12H), 1.05 (d, J=6.6 Hz, 6H)

Intermediate 38

1-(4-Bromo-2,5-difluorobenzyl)-4-isopropylpiperazine

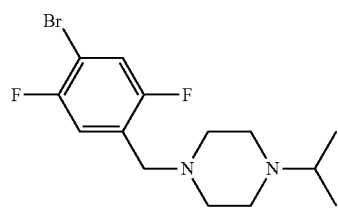 [SMILES: CC(C)N1CCN(Cc2cc(F)c(Br)cc2F)CC1]

4-Bromo-2,5-difluorobenzaldehyde (available from Fluorochem, 1 g, 4.52 mmol) and 1-isopropylpiperazine (0.65 mL, 4.54 mmol) in DCM (12 mL) were stirred for 15 min before addition of sodium triacetoxyborohydride (1.2 g, 5.66 mmol). The resulting solution was stirred for 15 h. Saturated aqueous sodium hydrogen carbonate (30 mL) was then added and the aqueous phase was separared and extracted with DCM (30 mL). The organic phase was dried (hydrophobic frit) and concentrated under reduced pressure. The residue (yellow oil) still contained some solid (presumed to be inorganics) so it was dissolved in EtOAC (50 mL) and was washed with water (2×50 mL). The organic phase was dried (hydrophobic frit) and was concentrated under reduced pressure to afford the title compound (1.38 g) as a yellow oil.

LCMS (Method A) R$_t$=0.57 min, [M+H]$^+$=333.3/335.3.

Intermediate 39

N-(2-(2-Fluoro-4-formylphenyl)pyridin-4-yl)-2-methoxy-5-morpholinopyridine-3-sulfonamide

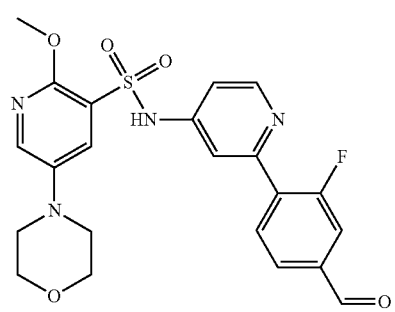 [SMILES: COc1ncc(N2CCOCC2)cc1S(=O)(=O)Nc1ccnc(-c2ccc(C=O)cc2F)c1]

A vial was charged with N-(2-chloropyridin-4-yl)-2-methoxy-5-morpholinopyridine-3-sulfonamide (2809 mg, 7.30 mmol), (2-fluoro-4-formylphenyl)boronic acid (2494 mg, 14.85 mmol), sodium carbonate (3100 mg, 29.2 mmol) and XPhos palladacycle (520 mg, 0.704 mmol) in water (8 mL) and 1,4-dioxane (24 mL). The vial was sealed and the reaction mixture was heated at 120° C. for 60 min thermally. The reaction mixture was filtered through celite and washed with MeOH. The filtrate was concentrated under reduced pressure. The residue was pre-absorbed on florisil and purified by chromatography on silica eluting with a gradient of 0 to 50% 3:1 EtOAc:EtOH in cyclohexane. The desired fractions were concentrated under reduced pressure and the residue was dissolved in the minimum amount of MeOH and sonicated. The precipitate was collected by filtration and dried to afford the title compound (874 mg) as a yellow solid.

LCMS (Method A) Rt=0.87 min, [M+H]+=473.3.

Intermediate 40

N-(2-Chloropyridin-4-yl)-2-methoxy-5-morpholinopyridine-3-sulfonamide

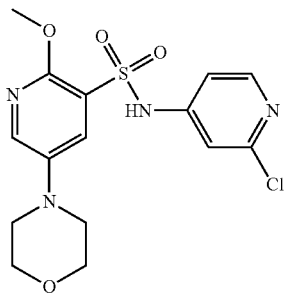 [SMILES: COc1ncc(N2CCOCC2)cc1S(=O)(=O)Nc1ccnc(Cl)c1]

A vial was charged with morpholine (8.10 mL, 93 mmol), 2-isobutyrylcyclohexanone (1.558 mL, 9.26 mmol), copper (I) iodide (588 mg, 3.09 mmol), potassium carbonate (6398 mg, 46.3 mmol), 5-bromo-N-(2-chloropyridin-4-yl)-2-methoxypyridine-3-sulfonamide (5843 mg, 15.43 mmol) and DMSO (60 mL). The vial was sealed, placed under vacuum then flushed with nitrogen (10 times), heated to 110° C. and left to stir for 18 h. The reaction was cooled and the reaction mixture added to water (200 mL), acidified to pH 1 with aqueous HCl (4M), extracted with EtOAc (200 mL) and the organic layer was separated. The aqueous layer was readjusted to pH 1 with aqueous HCl (4M) and re-extracted with EtOAc (2×200 mL). The organic layers were combined, filtered using a hydrophobic frit and concentrated under reduced pressure to afford the crude product as a brown oil that solidified. The residue was diluted with MeOH (30 mL) and sonicated. The tan precipitate was collected by filtration, washed with MeOH (5 mL), and dried to afford the title compound (3373 mg) as a tan solid.

LCMS (Method A) Rt=0.89 min, [M+H]+=385.0.

Intermediate 41

5-Bromo-N-(2-chloropyridin-4-yl)-2-methoxypyridine-3-sulfonamide

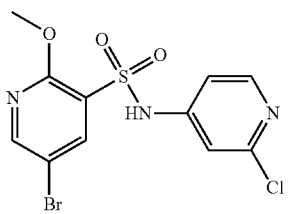 [SMILES: COc1ncc(Br)cc1S(=O)(=O)Nc1ccnc(Cl)c1]

A round bottomed flask was charged with 5-bromo-2-chloro-N-(2-chloropyridin-4-yl)pyridine-3-sulfonamide (8 g, 20.89 mmol). Sodium methoxide in MeOH (0.5 M, 200 mL, 100 mmol) was added and the reaction mixture was placed under vacuum then flushed with nitrogen, sealed, and heated at 100° C. for 6 h. The reaction mixture was concentrated under reduced pressure and the pH of the mixture was adjusted to 7 with aqueous HCl (4M). The residue was partitioned between water (100 mL) and EtOAc (200 mL). The organic layer was separated and the aqueous layer was re-extracted with EtOAc (200 mL). The pH of the aqueous layer was then adjusted to 6 with aqueous HCl (4M) and re-extracted with EtOAc (200 mL). The pH of the aqueous layer was then adjusted to 4 with aqueous HCl (4M), and re-extracted with EtOAc (200 mL). The organic layers were combined, dried using a hydrophobic frit, and concentrated under reduced pressure. The residue was then dissolved in the minimum amount of MeOH and sonicated. The precipitate was collected by filtration and dried to afford the title compound (6.531 g) as a tan solid.

LCMS (Method A) Rt=1.06 min, [M+H]+=379.9.

Intermediate 42

5-Bromo-2-chloro-N-(2-chloropyridin-4-yl)pyridine-3-sulfonamide

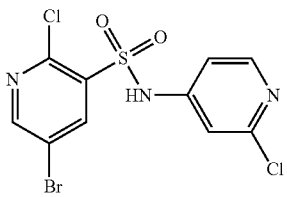 [SMILES: O=S(=O)(Nc1ccnc(Cl)c1)c1cc(Br)cnc1Cl]

To a solution of 5-bromo-2-chloropyridine-3-sulfonyl chloride (available from Enamine, 13.73 g, 47.2 mmol) in pyridine (50 mL, 618 mmol) was added portionwise 2-chloropyridin-4-amine (6.7 g, 52.1 mmol). The reaction mixture was stirred at room temperature for 3 h. The reaction mixture was concentrated under reduced pressure. The residue was treated with MeOH (50 mL) and the mixture was sonicated. The brown precipitate was collected by filtration, washed with MeOH (5 mL), dried, then dissolved in MeCN and concentrated under reduced pressure to afford the title compound (15.44 g) as a brown solid.

LCMS (Method A) Rt=0.64 min, [M+H]+=383.8.

Intermediate 43 tert-Butyl 4-(3-fluoro-4-(4-(2-methoxy-5-morpholinopyridine-3-sulfonamido)pyridin-2-yl)benzyl)piperazine-1-carboxylate, formic acid salt

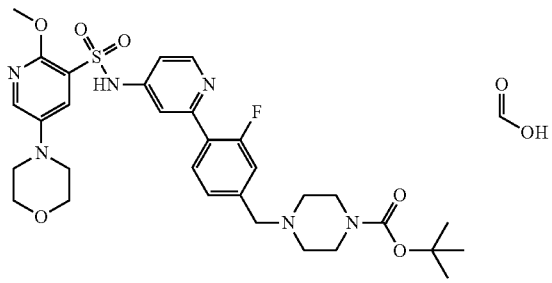 [SMILES: COc1ncc(N2CCOCC2)cc1S(=O)(=O)Nc1ccnc(-c2ccc(CN3CCN(C(=O)OC(C)(C)C)CC3)cc2F)c1 ; O=CO]

A vial was charged with tert-butyl 4-(4-(4-(5-chloro-2-methoxpyridine-3-sulfonamido)pyridin-2-yl)-3-fluorobenzyl)piperazine-1-carboxylate (1428 mg, 2.412 mmol), morpholine (0.5 mL, 5.72 mmol), sodium tert-butoxide (1415 mg, 14.72 mmol), Pd(OAc)$_2$ (69 mg, 0.307 mmol), RuPhos (234 mg, 0.501 mmol) and toluene (15 mL). The vial was sealed, heated thermally to 90° C. and left to stir for 30 min. The reaction mixture was filtered through celite and washed with MeOH. The filtrate was concentrated under reduced pressure. The residue was dissolved in 16:3:1 water (containing 0.1% formic acid):MeOH:DMSO (20 mL) and eluted on a C18 reverse-phase silica gel column with a gradient of 5% to 30% MeCN (containing 0.1% formic acid) in water (containing 0.1% formic acid). The desired fractions were concentrated under reduced pressure to afford the title compound (1.128 g) as a dark brown solid.

LCMS (Method A) R$_t$=0.66 min, [M+H]$^+$=643.2.

Intermediate 44 tert-Butyl 4-(4-(4-(5-chloro-2-methoxypyridine-3-sulfonamido)pyridin-2-yl)-3-fluorobenzyl)piperazine-1-carboxylate

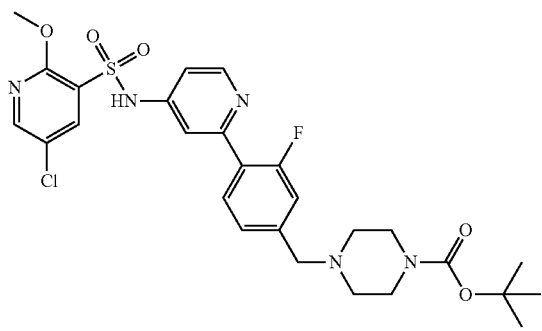 [SMILES: COc1ncc(Cl)cc1S(=O)(=O)Nc1ccnc(-c2ccc(CN3CCN(C(=O)OC(C)(C)C)CC3)cc2F)c1]

tert-Butyl piperazine-1-carboxylate (904 mg, 4.85 mmol) and (2-fluoro-4-formylphenyl)boronic acid (799 mg, 4.76 mmol) in DCM (20 mL) were stirred for 15 min before addition of sodium triacetoxyborohydride (1350 mg, 6.37 mmol). The resulting solution was stirred for 45 min. The reaction mixture was concentrated under reduced pressure. Sodium carbonate (1341 mg, 12.66 mmol), PdCl$_2$(dppf) (72 mg, 0.098 mmol), N-(2-bromopyridin-4-yl)-5-chloro-2-methoxypyridine-3-sulfonamide (1199 mg, 3.17 mmol), EtOH (10 mL) and water (10 mL) were added to the residue, and the reaction was heated at reflux (100° C.) for 1.5 h. The reaction mixture was filtered through celite and washed with MeOH. The filtrate was concentrated under reduced pressure. The residue was dissolved in 13:4:2 water (with an ammonium bicarbonate modifier adjusted to pH 10):MeOH:DMSO (19 mL) and eluted on a C18 reverse-phase silica gel column with a gradient of 15% to 70% MeCN (containing 0.1% NH$_3$) in water (with an ammonium bicarbonate modifier adjusted to pH 10). The desired fractions were concentrated under reduced pressure to afford the title compound (1.428 g) as a brown solid.

LCMS (Method B) R$_t$=0.96 min, [M+H]$^+$=594.3.

Intermediate 45

5-Chloro-2-(dimethylamino)-N-(2-(2-fluoro-4-((4-isopropylpiperazin-1-yl)methyl)phenyl)pyridin-4-yl)pyridine-3-sulfonamide

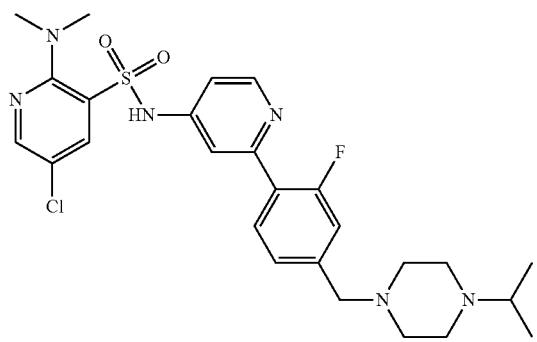 [SMILES: CC(C)N1CCN(Cc2ccc(-c3cc(NS(=O)(=O)c4cc(Cl)cnc4N(C)C)ccn3)c(F)c2)CC1]

To a stirred suspension of 5-chloro-2-(dimethylamino)-N-(2-(2-fluoro-4-formylphenyl)pyridin-4-yl)pyridine-3-sulfonamide (50 mg, 0.115 mmol) in MeOH (2 mL) and acetic acid (0.2 mL) was added 1-isopropylpiperazine (29.5 mg, 0.230 mmol) at room temperature. The reaction mixture was stirred for 2 h at room temperature and 2-picolineborane (18.40 mg, 0.172 mmol) was then added. The reaction mixture was allowed to stirr for 16 h at 50° C. The reaction solvent was evaporated to get a crude residue (90 mg). The reaction was repeated to obtain more material: to a stirred suspension of 5-chloro-2-(dimethylamino)-N-(2-(2-fluoro-4-formylphenyl)pyridin-4-yl)pyridine-3-sulfonamide (450 mg, 1.035 mmol) in MeOH (6 mL) and acetic acid (0.5 mL) was added 1-isopropylpiperazine (265 mg, 2.070 mmol) at room temperature. The reaction mixture was stirred for 2 h at room temperature and 2-picolineborane (166 mg, 1.552 mmol) was then added. The reaction mixture was allowed to stir for 16 h at 50° C. The reaction solvent was evaporated to get a crude residue (1.1 g). Both residues (90 mg and 1.1 g) were combined and purified by Preparative-HPLC (Method G). Collected fractions were evaporated to afford the title compound (500 mg) as off white solid.

LCMS (Method G) R$_t$=1.64 min, [M+H]$^+$=547.2.

Intermediate 46

5-Chloro-2-(dimethylamino)-N-(2-(2-fluoro-4-formylphenyl)pyridin-4-yl)pyridine-3-sulfonamide

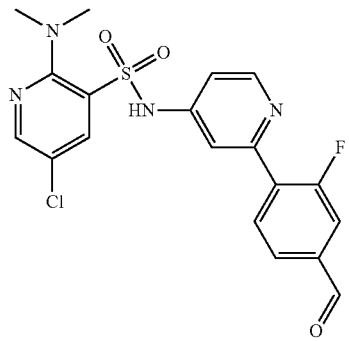 [SMILES: CN(C)c1ncc(Cl)cc1S(=O)(=O)Nc1ccnc(-c2ccc(C=O)cc2F)c1]

To a stirred solution of N-(2-bromopyridin-4-yl)-5-chloro-2-(dimethylamino)pyridine-3-sulfonamide (2 g, 5.11 mmol) in 1,4-dioxane (20 mL) and water (6 mL) was added (2-fluoro-4-formylphenyl)boronic acid (0.943 g, 5.62 mmol) and $K_3PO_4$ (2.71 g, 12.77 mmol) then the reaction mixture was degassed for 30 min. To the reaction mixture was added Xphos pre-catalyst $2^{nd}$ generation (0.201 g, 0.255 mmol) and the mixture was again degassed for 15 min and then heated at 110° C. for 16 h. The reaction mixture was filtered through celite, washed with 10% MeOH/DCM and the solvent evaporated to get a crude residue. The residue was purified by silica gel column chromatography (100-200 μm), eluting with 40% EtOAc in n-hexane. The desired fractions were evaporated to afford the title compound (1 g) as brown solid.

LCMS (Method G) $R_t$=2.14 min, $[M+H]^+$=435.1.

Intermediate 47

N-(2-Bromopyridin-4-yl)-5-chloro-2-(dimethyl-amino)pyridine-3-sulfonamide

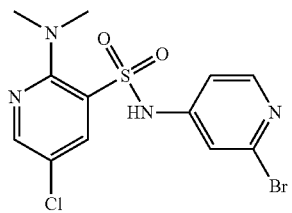 [SMILES: CN(C)c1ncc(Cl)cc1S(=O)(=O)Nc1ccnc(Br)c1]

To a solution of N-(2-bromopyridin-4-yl)-2,5-dichloro-pyridine-3-sulfonamide (13 g, 33.9 mmol) in EtOH (50 mL) was added dimethylamine (85 mL, 170 mmol), and the reaction was stirred for 16 h at 100° C. in sealed tube. The reaction mixture was evaporated to get a crude compound (17 g), which was purified by silica gel column chromatography (100-200 μm) eluting with 5% MeOH in DCM. The desired fractions were evaporated desired column fractions to afford the title compound (6 g) as brown solid.

LCMS (Method G) $R_t$=2.29 min, $[M+H]^+$=391.0/393.0.

Intermediate 48

N-(2-(4-((4-(tert-Butyl)piperazin-1-yl)methyl)-2-fluorophenyl)pyridin-4-yl)-5-chloro-2-(dimethyl-amino)pyridine-3-sulfonamide

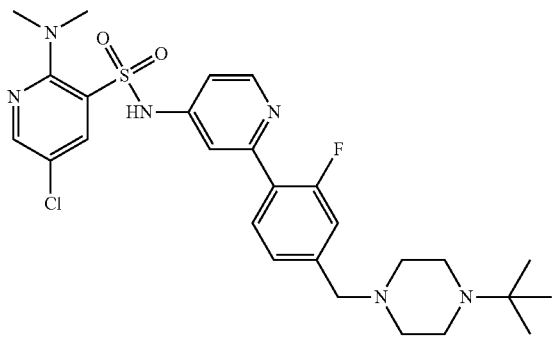 [SMILES: CN(C)c1ncc(Cl)cc1S(=O)(=O)Nc1ccnc(-c2ccc(CN3CCN(C(C)(C)C)CC3)cc2F)c1]

To a stirred suspension of 5-chloro-2-(dimethylamino)-N-(2-(2-fluoro-4-formylphenyl)pyridin-4-yl)pyridine-3-sulfonamide (50 mg, 0.115 mmol) in MeOH (2 mL) and acetic acid (0.2 mL) was added 1-(tert-butyl)piperazine (32.7 mg, 0.230 mmol) at room temperature. The reaction mixture was stirred for 2 h at room temperature then 2-picolineborane (18.40 mg, 0.172 mmol) was added and the reaction mixture was allowed to stir for 16 h at 50° C. The reaction solvent was evaporated to afford a crude residue (86 mg) as yellow gum. The reaction was repeated to obtain more material: to a stirred suspension of 5-chloro-2-(dimethylamino)-N-(2-(2-fluoro-4-formylphenyl)pyridin-4-yl)pyridine-3-sulfonamide (450 mg, 1.035 mmol) in MeOH (6 mL) and acetic acid (0.5 mL) was added 1-(tert-butyl)piperazine (294 mg, 2.070 mmol) at room temperature. The reaction mixture was stirred for 2 h at room temperature then 2-picolineborane (166 mg, 1.552 mmol) was added. The reaction mixture was allowed to stir for 16 h at 50° C. The reaction solvent was evaporated to get a crude residue (1.2 g). Both crude residues were combined and purified by Preparative-HPLC (Method I). The desired fractions were evaporated to afford the title compound (350 mg) as an off white solid.

LCMS (Method G) $R_t$=1.70 min, $[M+H]^+$=561.3.

Intermediate 49

5-Chloro-N-(2-(2-fluoro-4-((4-isopropylpiperazin-1-yl)methyl)phenyl)pyridin-4-yl)-2-methoxy-N-methylpyridine-3-sulfonamide

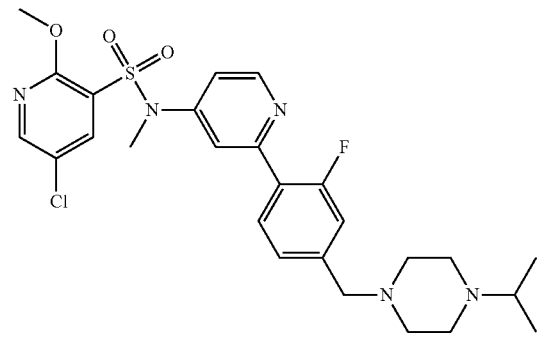 [SMILES: COc1ncc(Cl)cc1S(=O)(=O)N(C)c1ccnc(-c2ccc(CN3CCN(C(C)C)CC3)cc2F)c1]

N-(2-Bromopyridin-4-yl)-5-chloro-2-methoxy-N-methylpyridine-3-sulfonamide (660 mg, 1.681 mmol) was dissolved in EtOH (6 mL) and water (2.0 mL). To this was added (2-fluoro-4-((4-isopropylpiperazin-1-yl)methyl)phenyl)boronic acid (706 mg, 2.52 mmol), sodium carbonate (713 mg, 6.72 mmol) and [1,1'-bis(diphenylphosphino)ferrocene]dichloropalladium(II) (37.0 mg, 0.050 mmol) and the reaction mixture heated to 100° C. for 2 h. The reaction mixture was then concentrated in vacuo and partitioned between EtOAc (50 mL) and water (50 mL), the pH was adjusted to ~10 with 1 M NaOH. The aqueous phase was then separated and extracted with further EtOAc (50 mL), the combined organic extracts were dried by passing through a hydrophobic frit and concentrated in vacuo to give an orange gum. The orange gum was purified by reverse phase C18 column chromatography, eluting with a gradient of 50% to 75% MeCN (containing 0.1% $NH_3$) in water (with an ammonium bicarbonate modifier adjusted to pH 10). The appropriate fractions were combined and concentrated in vacuo to afford the title compound (300 mg) as a brown gum.

LCMS (Method B) $R_t$=1.34 min, $[M+H]^+$=548.1.

Intermediate 50

(2-Fluoro-4-((4-isopropylpiperazin-1-yl)methyl)phenyl)boronic acid

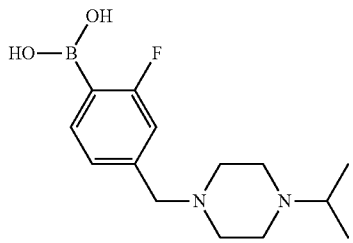 [SMILES: CC(C)N1CCN(Cc2ccc(B(O)O)c(F)c2)CC1]

(2-Fluoro-4-formylphenyl)boronic acid (8.15 g, 48.5 mmol) and 1-isopropylpiperazine (6.94 mL, 48.5 mmol) in DCM (100 mL) were stirred for 15 min before addition of sodium triacetoxyborohydride (12.34 g, 58.2 mmol). The resulting solution was stirred for 2 h. The reaction mixture was then concentrated under reduced pressure and the residue was purified by reverse-phase C18 silica chromatography eluting with a gradient of 0 to 20% MeCN (containing 0.1% $NH_3$) in water (with an ammonium bicarbonate modifier adjusted to pH 10). The desired fractions were concentrated under reduced pressure to afford the title compound (11.7 g) as a yellow solid.

LCMS (Method B) $R_t$=0.56 min, $[M+H]^+$=281.3.

Intermediate 51

N-(2-Bromopyridin-4-yl)-5-chloro-2-methoxy-N-methylpyridine-3-sulfonamide

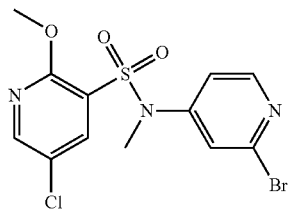 [SMILES: COc1ncc(Cl)cc1S(=O)(=O)N(C)c1ccnc(Br)c1]

N-(2-Bromopyridin-4-yl)-5-chloro-2-methoxpyridine-3-sulfonamide (1.4 g, 3.70 mmol) was dissolved in anhydrous DMF (10 mL), to this was added potassium carbonate (0.613 g, 4.44 mmol) and iodomethane (0.277 mL, 4.44 mmol) and the reaction mixture stirred at room temperature for 18 h. Further iodomethane (0.277 mL, 4.44 mmol) was added and the reaction mixture continued to stir at room temperature for 3 h. The reaction mixture was then concentrated in vacuo and partitioned between EtOAc (200 mL) and saturated aqueous $NH_4Cl$ (200 mL). The aqueous phase was separated and extracted with further EtOAc (200 mL), the combined organic extracts were then concentrated in vacuo and purified by silica chromatography eluting with a gradient of 0 to 50% EtOAc in cyclohexane to afford the title compound (960 mg).

LCMS (Method B) $R_t$=1.16 min, $[M+H]^+$=391.9/393.9/395.9.

Intermediate 52

5-Chloro-N-ethyl-N-(2-(2-fluoro-4-((4-isopropylpiperazin-1-yl)methyl)phenyl)pyridin-4-yl)-2-methoxypyridine-3-sulfonamide

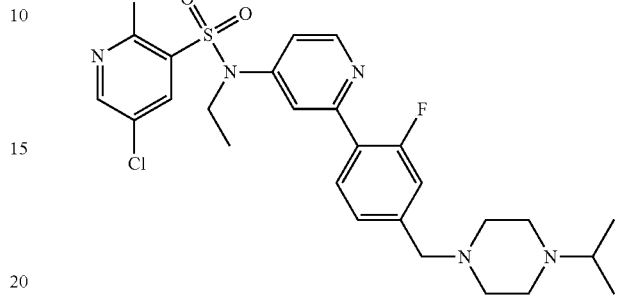

Potassium carbonate (0.548 g, 3.96 mmol) and iodoethane (0.320 mL, 3.96 mmol) were added to a solution of N-(2-bromopyridin-4-yl)-5-chloro-2-methoxypyridine-3-sulfonamide (1 g, 2.64 mmol) in anhydrous DMF (10 mL) placed in a vial. The vial was sealed and stirred room temperature for 18 h. Further iodoethane (0.107 mL, 1.321 mmol) was added and the reaction mixture continued to stir for 18 h. The reaction mixture was then concentrated in vacuo and partitioned between EtOAc (100 mL) and saturated aqueous NaCl (100 mL). The aqueous phase was separated and extracted with further EtOAc (100 mL), the combined organic solutions were then concentrated in vacuo to afford a brown oil (1.079 g). This brown oil (1.079 g, 2.65 mmol), (2-fluoro-4-((4-isopropylpiperazin-1-yl)methyl)phenyl)boronic acid (1.115 g, 3.98 mmol), [1,1'-bis(diphenylphosphino)ferrocene]dichloropalladium(II) (0.058 g, 0.080 mmol) and sodium carbonate (1.125 g, 10.61 mmol) were dissolved in EtOH (15 mL) and water (5 mL) and the reaction mixture was heated to 100° C. for 4 h. Further portions of [1,1'-bis(diphenylphosphino)ferrocene]dichloropalladium(II) (0.058 g, 0.080 mmol) and (2-fluoro-4-((4-isopropylpiperazin-1-yl)methyl)phenyl)boronic acid (0.743 g, 2.65 mmol) were added and the reaction mixture stirred at 100° C. for 18 h. The reaction mixture was then concentrated in vacuo and partitioned between EtOAc (100 mL) and saturated aqueous sodium bicarbonate (100 mL), the aqueous phase was separated and extracted with further EtOAc (100 mL). The combined organic solutions were concentrated in vacuo and purified by ion exchange $NH_2$ SPE, eluting with a gradient of 0 to 100% EtOAc in cyclohexane. The appropriate fractions were combined and concentrated in vacuo to afford the title compound (785 mg) as an orange oil.

LCMS (Method B) $R_t$=1.39 min, $[M+H]^+$=562.1.

Intermediate 53 tert-Butyl (2-bromopyridin-4-yl)carbamate

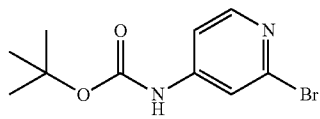

Charge 2-bromopyridin-4-amine (100.0 g), Et3N (64.8 g) and DCM (1.0 L) into the reaction vessel, stir the reaction mixture at 20-30° C. for 15-30 min. Charge DMAP (3.5 g) into the reaction vessel, add (Boc)₂O (416.3 g) dropwise into the reaction vessel. Stir the reaction vessel at 20-30° C. for 16 h, check the reaction with HPLC. Wash the reaction mixture with water (2 L). Separate the organic phase and concentrate under reduced pressure to give crude product as yellow solid. Slurry the obtained solid with MeOH (300.0 mL) at 20-30° C. for 30 min, then filter to get the title compound (171.2 g) as off-white solid.

Intermediate 54

5-Bromo-2-chloropyridine-3-sulfonyl chloride

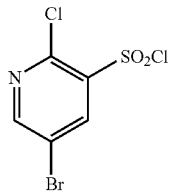

Method A
Step A: Charge water (2.1 L) into a first reaction vessel, adjust the temperature to −5-0° C. Charge SOCl₂ (550.0 g) to the reaction vessel slowly at −5-0° C., stir the solution at 0-5° C. for 18 h. Add CuCl (1.34 g) to the reaction vessel and adjust the temperature to about −15° C. Step B: Charge 5-bromo-2-chloropyridin-3-amine (140.0 g) and concentrated HCl (1.4 L) into a second reaction vessel, adjust the temperature to about −15° C. Add NaNO₂ (84.2 g) to the reaction vessel slowly to maintain the temperature at about −5° C., stir the mixture at around −5° C. for 15-30 min.

Transfer the mixture in the second reaction vessel to the first reaction vessel slowly and maintain the temperature of the first reaction vessel around −10° C. Stir the resulting mixture in the first reaction vessel at −10° C. for 2 h. Filter the mixture and collect the solid. Dry the solid under reduced pressure at 45-55° C. for 18 h to give crude product (159.2 g) as light yellow solid.

Purification: Treat crude product (320 g) with EtOAc (700 mL). Stir the mixture for 5 min. Filter the mixture and wash the solid (inorganic salt) with EtOAc (100 mL). Concentrate the filtrate under reduced pressure to about 300 mL. Add n-heptane (300 mL) to the mixture and concentrate. Dry the product under reduced pressure at 35-40° C. for 18 h to give the title compound (292 g) as orange solid.
Method B
In vessel 1, thionyl chloride (110.0 kg) was added into water (430 kg) at ca. 0° C. The mixture was stirred at ca. 3° C. for 7 h before copper(I) chloride (0.27 kg) was added at ca. 3° C.

In vessel 2, 5-bromo-2-chloropyridin-3-amine (28.2 kg, 136 Mol) was mixed with 35% aqueous hydrochloric acid solution (202 kg) at ca. 5° C. A solution of sodium nitrite (8.5-14.1 kg) in water (19.7-25.4 kg) was then added at ca. −10° C.

The solution in Vessel 2 was added to the solution in vessel 1 while maintaining the temperature at ca. −7° C. The reaction mixture was stirred for 2 h at ca. −2° C. The solid solid product was isolated by filtration and dried in vacuo at ca. 23° C. for 18 h. 30.9 kg of the title compound was obtained in 66%th yield and 84.3% assay.

Intermediate 55 tert-Butyl (2-(2-fluoro-4-((4-isopropylpiperazin-1-yl)methyl)phenyl)pyridin-4-yl)carbamate

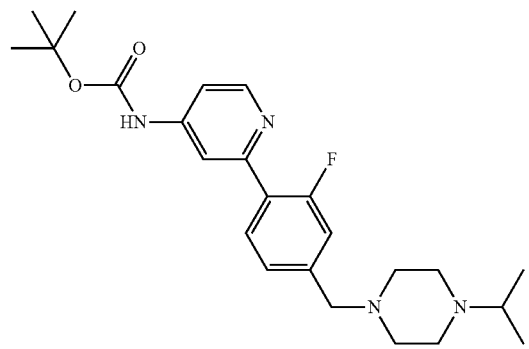 [SMILES: CC(C)N1CCN(Cc2ccc(-c3cc(NC(=O)OC(C)(C)C)ccn3)c(F)c2)CC1]

Charge tert-butyl (2-bromopyridin-4-yl)carbamate (187.3 g), 1-(3-fluoro-4-(4,4,5,5-tetramethyl-1,3,2-dioxaborolan-2-yl)benzyl)-4-isopropylpiperazine (200.0 g), Na₂CO₃ (212.8 g), IPA (1.4 L) and water (470 mL) into a reaction vessel, degas the reaction vessel with N₂ three times. Charge PdCl₂(dppf) (18.4 g) into the reaction vessel, adjust the reaction vessel to 80-90° C., stir the reaction mixture at 80-90° C. for 18 h. Check the reaction with HPLC. Cool the reaction mixture to 20-30° C., filter through celite (200.0 g) and concentrate the filtrate under reduced pressure to remove most of IPA. Charge DCM (1.0 L) into the residue and stir for 15-30 min. Separate the organic phase and wash with water (2×1.0 L), the DCM solution of the title compound was stored at 20-30° C. and used for next step directly.

Intermediate 56

2-(2-Fluoro-4-((4-isopropylpiperazin-1-yl)methyl)phenyl)pyridin-4-amine

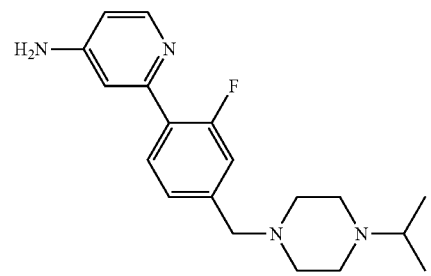 [SMILES: CC(C)N1CCN(Cc2ccc(-c3cc(N)ccn3)c(F)c2)CC1]

Method A
Charge tert-butyl (2-(2-fluoro-4-((4-isopropylpiperazin-1-yl)methyl)phenyl)pyridin-4-yl)carbamate (318.2 g, in DCM) and 2N HCl (3.0 L) into a reaction vessel. Stir the reaction mixture at 20-30° C. for 18 h. Check the reaction with HPLC till the disappearance of tert-butyl (2-(2-fluoro-4-((4-isopropylpiperazin-1-yl)methyl)phenyl)pyridin-4-yl)carbamate. Separate the aqueous layer and wash with EtOAc (2×1.0 L). Adjust the pH to 9-10 with aqueous ammonia, then extract with EtOAc (2×1.0 L). Combine the organic phase and wash with water (2×1.0 L). Separate the organic layer and concentrate to get the title compound (161.6 g) as a black oil.

Method B

2-Bromopyridin-4-amine (11.5 kg) and a solution of 1-(3-fluoro-4-(4,4,5,5-tetramethyl-1,3,2-dioxaborolan-2-yl)benzyl)-4-isopropylpiperazine in 2-methyltetrahydrofuran (145.4 kg of solution, containing 29.8 kg/82.3 Mol of 1-(3-fluoro-4-(4,4,5,5-tetramethyl-1,3,2-dioxaborolan-2-yl)benzyl)-4-isopropylpiperazine) were dissolved in 2-methyltetrahydrofuran (ca. 53 kg). Sodium carbonate (35.0 kg) and water (75 kg) were added. Nitrogen was bubbled through the mixture for 3 h at ca. 25° C. [1,1'-Bis(diphenylphosphino)ferrocene]dichloropalladium(II) (1.36 kg) was added, before nirogen was bubbled through the mixture for 3 h at ca. 25° C. The mixture was stirred for 16 h at ca. 73° C. The temperature was reduced to ca. 33° C. and water (89 kg) was added. The resulting mixture was stirred for 2 h before the aqueous layer was discarded. The organic layer was filtered through a flash silica gel column (3 kg). Water (60 kg) was added to the organic layer. 20% citric acid aqueous solution (110 kg) was added until pH=4-6. The organic layer was discarded and n-heptane (60 kg) was added to the aqueous layer. 30% sodium hydroxide aqueous solution (51 kg) was added at 10° C., adjusting pH=8-9. The temperature was adjusted to ca. 8° C. and the solution was seeded with 2-(2-fluoro-4-((4-isopropylpiperazin-1-yl)methyl)phenyl)pyridin-4-amine (0.10 kg). The resulting suspension was stirred for 2 h. 30% sodium hydroxide aqueous solution (15 kg) was added to adjust pH=10-11. The suspension was further aged for 15 h at ca. 8° C. The solid product was isolated by filtration, before being dissolved in acetone (262.0 kg) at ca. 40° C. The resulting solution was concentrated to 30 L under reduced pressure, maintaining the temperature below 35° C. Water (65 kg) was added over 3 h at ca. 8° C. and the suspension was stirred for 2 h. Water (45 kg) was added over 3.5 h at ca. 8° C. before the suspension was aged for 6 h at 4° C. The solid product was collected by filtration and dried for 48 h at ca.28° C. under reduced pressure. Finally, 20.1 kg of the title compound was obtained in 76% th yield.

Intermediate 57

5-Bromo-2-chloro-N-(2-(2-fluoro-4-((4-isopropylpiperazin-1-yl)methyl)phenyl)pyridin-4-yl)pyridine-3-sulfonamide

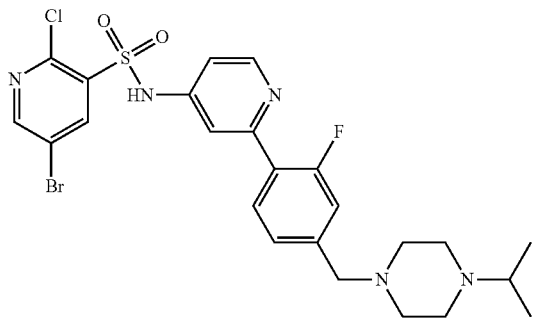 [SMILES: CC(C)N1CCN(Cc2ccc(-c3cc(NS(=O)(=O)c4cc(Br)cnc4Cl)ccn3)c(F)c2)CC1]

Method A

Charge 2-(2-fluoro-4-((4-isopropylpiperazin-1-yl)methyl)phenyl)pyridin-4-amine (65.6 g) and DCM (656 mL) into a reaction vessel under N2 atmosphere. Add 5-bromo-2-chloropyridine-3-sulfonyl chloride (87.4 g) into the solution portionwise. Stir the mixture at 15-25° C. for 15 min. Add Et₃N (83.2 mL) to the mixture slowly over 15 min. The resulting mixture was stirred at 15-25° C. for 16 h. Additional 5-bromo-2-chloropyridine-3-sulfonyl chloride (29.1 g) was added. The reaction mixture was stirred for another 20 h before quench with aqueous Na₂CO₃ solution (15%, 300 mL). The organic layer was separated and washed with 2N HCl (600 mL). Discard the organic layer. The aqueous layer was basified to pH=10 with aqueous ammonia solution, washed with of DCM (600 mL), and separated. The organic layer was concentrated under reduced pressure to give crude product (105 g) as yellow foam, with compound 2-(2-fluoro-4-((4-isopropylpiperazin-1-yl)methyl)phenyl)pyridin-4-amine and bis-sulfonyl byproduct as impurities.

Method B 2-(2-fluoro-4-((4-isopropylpiperazin-1-yl)methyl)phenyl)pyridin-4-amine (14.8 kg corrected by assay, 45.1 Mol) was dissolved in dichloromethane (160 kg). The solution was concentrated to 44.4-59.2 L under reduced pressure, maintaining the temperature below 50° C. Dichloromethane (326 kg) was added in two portions during the concentration step. 5-bromo-2-chloropyridine-3-sulfonyl chloride (24.6 kg corrected by assay) and triethylamine (18.2 kg) were added while maintaining the contents temperature below 30° C. The reaction mixture was stirred for 5 h at ca. 25° C. 5% sodium bicarbonate aqueous solution (74 kg—calculated from water 1.3-1.4 wt and 7% sodium bicarbonate 3.6-3.7 wt) was added and the mixture was stirred for 20 h at ca. 23° C. The aqueous phase was discarded. 2.5% sodium bicarbonate aqueous solution (74 kg—calculated from water 3.1-3.2 wt and 7% sodium bicarbonate 1.8-1.9 wt) was added into the organic phase and the resulting mixture was stirred for 20 h at 23° C. The aqueous phase was discarded. The organic layer was concentrated to 29.6-44.4 L. Methanol (322 kg) was added in three portions during the concentration in order to displace dichloromethane. Finally, a solution of the title compound in methanol (containing 18 kg of the title compound corrected by assay) was obtained with 73.8% purity.

Intermediate 58

5-Bromo-N-(2-(2-fluoro-4-((4-isopropylpiperazin-1-yl)methyl)phenyl)pyridin-4-yl)-2-methoxypyridine-3-sulfonamide

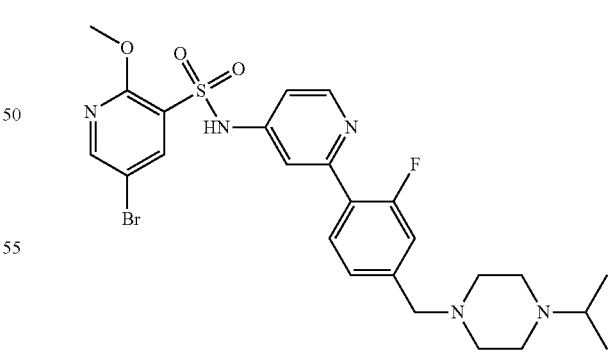

Method A

Charge 5-bromo-2-chloro-N-(2-(2-fluoro-4-((4-isopropylpiperazin-1-yl)methyl)phenyl)pyridin-4-yl)pyridine-3-sulfonamide (38 g) and MeOH (304 mL) into a reaction vessel. Add NaOMe (17.6 g) to the solution portionwise. Stir the resulting mixture at 70° C. for 3 h. Cool the reaction mixture to 15-25° C. Concentrate the reaction mixture to ~450 mL.

Dilute the mixture with DCM (200 mL) and extract with water (400 mL). Separate the aqueous layer and adjust the pH to about 3 with 2N HCl. Add DCM (300 mL) to the aqueous solution. Further adjust the pH of this mixture to about 10 with aqueous ammonia solution. Separate the organic layer and wash the aqueous layer with DCM (2×150 mL). Combine the organic layers and concentrate to dryness under reduced pressure to give of the title compound (81.0 g) as light yellow foam.

Method B

To a solution of 5-bromo-2-chloro-N-(2-(2-fluoro-4-((4-isopropylpiperazin-1-yl)methyl)phenyl)pyridin-4-yl)pyridine-3-sulfonamide in methanol (18 kg, 30.9 Mol) was added a solution of sodium hydroxdide in methanol (26.0 kg, 1.4-1.5 wt), maintaining the temperature below 30° C. The mixture was stirred for 14 h at ca. 67° C. The reaction mixture was concentrated to 36-54 L under reduced pressure, maintaining the temperature below 50° C. Dichloromethane (113 kg) and process water (280 kg) were added. The two layers were separated and the organic layer was discarded. To the aqueous layer were added dichloromethane (105 kg) and 2 N aqueous hydrochloric acid (48 kg), adjusting the pH to ca. 4. 25% aqueous ammonia solution (3 kg) was added at 25° C. until the pH was adjusted to ca. 7.8. The two layers were separated and the aqueous layer was discarded. To the organic layer was added tert-butyl methyl ether (45 kg). The mixture was seeded with 5-bromo-N-(2-(2-fluoro-4-((4-isopropylpiperazin-1-yl)methyl)phenyl) pyridin-4-yl)-2-methoxypyridine-3-sulfonamide (0.199 kg) before being stirred for 16 h at 33° C. tert-Butyl methyl ether (180 kg) was added while concentrating to a volume of 72-90 L. The resulting suspension was aged for 2.5 h at 3° C. before the solid was isolated by centrifuge. The solid product was dried in vacuo at ca. 38° C. to afford 18.8 kg of the title compound in 70% th yield.

Intermediate 59

Rac-5-Chloro-N-(2-(4-(((2S,6R)-2,6-dimethylmorpholino)methyl)-2-fluorophenyl)pyridin-4-yl)-2-methoxypyridine-3-sulfonamide

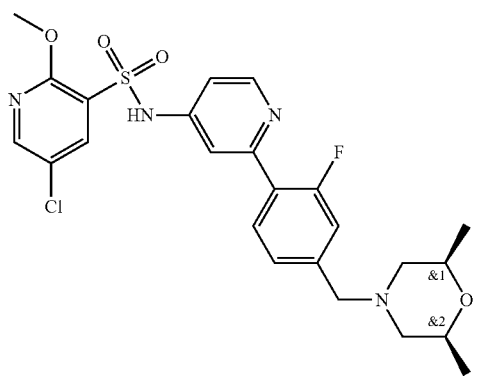 [SMILES: COc1ncc(Cl)cc1S(=O)(=O)Nc1ccnc(-c2ccc(CN3C[C@@H](C)O[C@@H](C)C3)cc2F)c1]

To a solution of 5-chloro-N-(2-(2-fluoro-4-formylphenyl) pyridin-4-yl)-2-methoxpyridine-3-sulfonamide (200 mg, 0.474 mmol), rac-(2R,6S)-2,6-dimethylmorpholine (82 mg, 0.711 mmol) in MeOH (0.2 mL) and acetic acid (5 mL) under nitrogen was added 2-picolineborane (75 mg, 0.711 mmol) portionwise over one minute at 0° C. After stirring for 16 h at 50° C., the mixture was quenched with saturated aqueous sodium bicarbonate solution (5 mL) and extracted with DCM (2×10 mL). The combined organic extracts were washed with brine (10 mL), dried over sodium sulfate, filtered and concentrated in vacuo to afford the title compound (150 mg) as a brown solid.

LCMS (Method G) $R_t$=1.57 min, $[M+H]^+$=519.1/521.0.

Intermediate 60

Rac-5-Chloro-N-(2-(4-(((2S,6R)-2,6-dimethylmorpholino)methyl)-2-fluorophenyppyridin-4-yl)-2-ethoxypyridine-3-sulfonamide

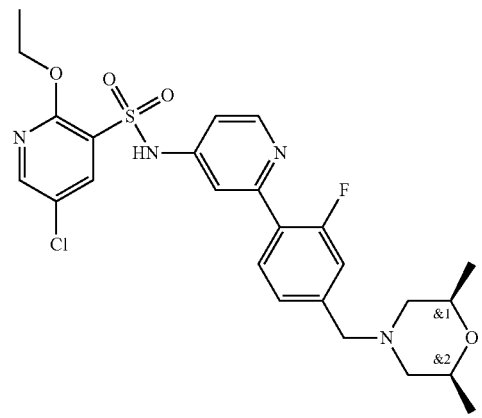 [SMILES: CCOc1ncc(Cl)cc1S(=O)(=O)Nc1ccnc(-c2ccc(CN3C[C@@H](C)O[C@@H](C)C3)cc2F)c1]

A solution of 5-chloro-2-ethoxy-N-(2-(2-fluoro-4-formylphenyl)pyridin-4-yl)pyridine-3-sulfonamide (900 mg, 2.065 mmol), rac-(2R,6S)-2,6-dimethylmorpholine (238 mg, 2.065 mmol) in MeOH (10 mL) and acetic acid (0.1 mL) was stirred for 15 min. 2-Picolineborane (331 mg, 3.10 mmol) was added and the mixture was stirred at 50° C. for 16 h. The mixture was quenched with saturated aqueous sodium bicarbonate solution (20 mL) and extracted with DCM (60 mL). The organic phase was washed with brine (30 mL), dried over sodium sulfate, filtered and concentrated in vacuo to afford the title compound (350 mg) as a brown solid.

LCMS (Method G) $R_t$=1.70 min, $[M+H]^+$=535.2.

Intermediate 61

5-Chloro-2-ethoxy-N-(2-(2-fluoro-4-formylphenyl) pyridin-4-yl)pyridine-3-sulfonamide and

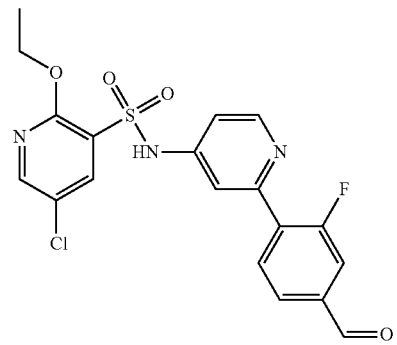 [SMILES: CCOc1ncc(Cl)cc1S(=O)(=O)Nc1ccnc(-c2ccc(C=O)cc2F)c1]

A stirred solution of N-(2-bromopyridin-4-yl)-5-chloro-2-ethoxypyridine-3-sulfonamide (900 mg, 2.292 mmol), (2-fluoro-4-formylphenyl)boronic acid (462 mg, 2.75 mmol) and Na$_2$CO$_3$ (972 mg, 9.17 mmol) in isopropanol (10 mL) water (3.33 mL) in a sealed tube was degassed with argon for 15 min at room temperature. PdCl$_2$(dppf)-CH$_2$Cl$_2$ adduct (94 mg, 0.115 mmol) was added and the mixture was degassed again using argon for 10 min. The reaction mixture was heated in the sealed tube at 90° C. for 4 h. The mixture was filtered through celite, washed with 10% MeOH/DCM (50 mL) and the solvent removed in vacuo. The residue was triturated with diethyl ether (2×20 mL) to afford the crude product (900 mg). The crude product was used for next step directly.

Intermediate 62

N-(2-bromopyridin-4-yl)-5-chloro-2-ethoxypyridine-3-sulfonamide

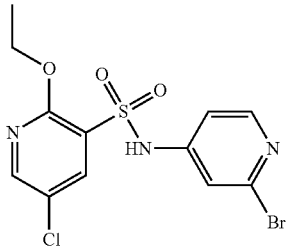 [SMILES: CCOc1ncc(Cl)cc1S(=O)(=O)Nc1ccnc(Br)c1]

To a stirred solution of N-(2-bromopyridin-4-yl)-2,5-dichloropyridine-3-sulfonamide (1 g, 2.61 mmol) in ethanol (10 mL) under nitrogen at room temperature sodium ethoxide (10 mL, 2.61 mmol) was added dropwise. The reaction mixture was stirred at 80° C. for 1 h then cooled to room temperature and concentrated in vacuo. The residue was taken up in 10% aqueous citric acid solution (50 mL) and the resulting precipitate was isolated by filtration to afford the title compound (0.9 g) as a brown solid.

LCMS (Method G) R$_t$=2.29 min, [M+H]$^+$=391.9/393.9.

Example 1

N-(2-(2-Fluoro-4-((4-isopropylpiperazin-1-yl)methyl)phenyl)pyridin-4-yl)-2-methoxy-5-morpholinopyridine-3-sulfonamide Method A

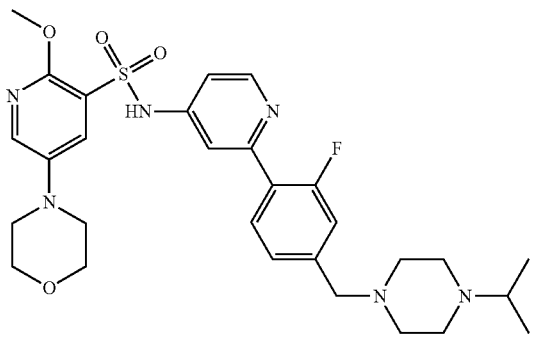 [SMILES: COc1ncc(N2CCOCC2)cc1S(=O)(=O)Nc1ccnc(-c2ccc(CN3CCN(C(C)C)CC3)cc2F)c1]

A 1 L sealed tube was charged with 5-chloro-N-(2-(2-fluoro-4-((4-isopropylpiperazin-1-yl)methyl)phenyl)pyridin-4-yl)-2-methoxypyridine-3-sulfonamide (20 g, 37.4 mmol), sodium tert-butoxide (10.80 g, 112 mmol) and morpholine (6.53 mL, 74.9 mmol) in dry toluene (400 mL). The above reaction mixture was degassed using argon for 30 min and 2-dicyclohexylphosphino-2',6'-diisopropoxybiphenyl (1.748 g, 3.74 mmol) was added followed by Pd(OAc)$_2$ (0.420 g, 1.872 mmol). The resulting reaction mixture was stirred at 90° C. for 3 h. The mixture was cooled to room temperature then diluted with EtOAc (1 L) and filtered through celite. The bed of celite was washed with an excess of EtOAc (500 mL) and the filtrates were combined and concentrated under reduced pressure. The residue was dissolved in water (500 mL) and the pH adjusted to 2-3 using 1M HCl (50 mL). The aqueous layer was extracted with EtOAc (2×500 mL). After separation, the aqueous layer was adjusted to pH 8-9 using aqueous ammonia solution (25%) then extracted with 10% MeOH in DCM (2×500 mL). The organic extracts were combined, dried over anhydrous sodium sulfate, filtered and concentrated under reduced pressure to afford the title compound (19 g) as an off-white foam.

The product (19 g) was further purified by silica gel chromatography using the GRACE REVELERIS instrument. The material was split into two lots (10 g and 9 g). Purification-1 (10 g, lot-1): the crude compound (10 g) was pre-absorbed onto silica gel (10 g, 100-200 mesh) and purified using a 120 g silica cartridge eluting with 6% MeOH in DCM (containing 0.1% NH$_3$ (aqueous)). The desired fractions were combined and evaporated under reduced pressure to afford 7.5 g of an off-white foam. Purification-2 (9 g crude, lot-2): The crude compound (9 g) was purified using the exact same method to afford 7 g as an off-white foam. The two batches (7.5 g and 7 g) were combined and dissolved in MeOH (150 mL) to obtain a clear solution, which was stirred for 30 min. The white solid which crystallised from the solution was collected by filtration, washed with diethylether (100 mL) and dried to afford the title compound (12 g) as a white solid.

LCMS (Method F) R$_t$=3.47 min, [M+H]$^+$=584.8

$^1$H NMR for N-(2-(2-fluoro-4-((4-isopropylpiperazin-1-yl)methyl)phenyl)pyridin-4-yl)-2-methoxy-5-morpholinopyridine-3-sulfonamide:

$^1$H NMR (600 MHz, DMSO-d6) ppm 1.00 (d, J=6.6 Hz, 6H), 2.39-2.47 (m, 4H), 2.53-2.58 (m, 4H), 2.70-2.75 (m, 1H), 3.04-3.08 (m, 4H), 3.52 (s, 2H), 3.71-3.76 (m, 4H), 3.83 (s, 3H), 6.97 (dd, J=5.6, 1.7 Hz, 1H), 7.20 (d, J=11.0 Hz, 1H), 7.21-7.23 (m, 1H), 7.39 (br s, 1H), 7.77 (t, J=8.2 Hz, 1H), 7.84 (d, J=3.0 Hz, 1H), 8.03 (d, J=3.0 Hz, 1H), 8.32 (br d, J=5.6 Hz, 1H), 11.01 (br s, 1H).

Method B

Charge 5-bromo-N-(2-(2-fluoro-4-((4-isopropylpiperazin-1-yl)methyl)phenyl)pyridin-4-yl)-2-methoxypyridine-3-sulfonamide (80 g), morpholine (24.1 mL), NaOtBu (26.6 g) and toluene (800 mL) to a flask. Purge the mixture with N$_2$ 3 times before adding Pd$_2$(dba)$_3$ (2.6 g) and Johnphos (3.3 g). Stir the mixture at 80° C. for 1 h. Cool the reaction mixture to 10-20° C. before condensing to ~300 mL. Dilute the mixture with EtOAc (300 mL) and wash with water (600 mL). Separate the aqueous layer and acidify to pH=3-4 with 2 N HCl. Wash the aqueous solution with EtOAc (2×300 mL). Adjust the pH of aqueous solution to 7-8 with aqueous ammonia. Wash the solution with DCM/MeOH (10/1, 2×400 mL). Combine the organic layers and concentrate to give 54 g of crude product as yellow foam. Recrystallisation of this crude product with MeOH/MeCN (1/3, 8 volumes) to give 31 g of product with 92.9% purity. Further recrystallization with MeOH/DCM (7/3, 6 volumes) and dried under reduced pressure at 40-45° C. for 18 h to give the title compound (22 g) as white solid with 98.9% purity.
Method C Into a vessel containing 5-bromo-N-(2-(2-fluoro-4-((4-isopropylpiperazin-1-yl)methyl)phenyl)pyridin-4-yl)-2-methoxypyridine-3-sulfonamide (16.0 kg corrected by assay, 27.7 Mol) were added toluene (65.0 kg), tris(dibenzylideneacetone)dipalladium(0) (0.60 kg), (2-Biphenyl)di-tert-butylphosphine (0.77 kg) and sodium tert-butoxide (5.8 kg) in sequence. Morpholine (5.4 kg) was added at 25° C. The reaction mixture was stirred for 1.5 h at ca. 83° C. before water (48.7 kg) was added at ca. 25° C. Tetrahydrofuran (6.5 kg) was added and the resulting mixture was filtered. The layers were separated and the organic layer was discarded. To the aqueous layer, tetrahydrofuran (100 kg), toluene (46.0 kg) and sodium chloride (8.0 kg) were added. N-Acetyl-L-cysteine (9.9 kg) was added at ca. 25° C., adjusting the pH to ca. 7.8. The mixture was stirred for 4 h at ca. 25° C. before the two layers were separated. The aqueous layer was extracted twice with tetrahydrofuran (2×100 kg) and twice with toluene (2×40.0 kg). The four organic layers were combined.

$1^{st}$ cycle to remove Palladium residues and $1^{st}$ crystallisation: To the combined organic layer was added silicathiol (1.7 kg). The mixture was stirred for 16 h at ca. 48° C. before being filtered. The resulting solution was circulated through a CUNO cartridge at ca. 48° C. for 16 h before tetrahydrofuran (16 kg) was added. Methanol (195 kg) was added in three portions while concentrating in vacuo to 48-64 L to remove tetrahydrofuran. The solution was heated to ca. 63° C., stirred for 4 h then cooled to ca. 3° C. over 3 h, before being stirred for 8 h. The solid was isolated by filtration.

$2^{nd}$ cycle to remove Palladium residues and $2^{nd}$ crystallisation: The wet solid was dissolved in tetrahydrofuran (210 kg) at ca. 60° C. The temperature was reduced to ca. 25° C. and silicathiol (1.6 kg) was added. The mixture was stirred at ca. 48° C. for 16 h before being filtered. The resulting solution was circulated through a CUNO cartridge at ca. 48° C. for 16 h before tetrahydrofuran (16 kg) was added. Methanol (194 kg) was added in three portions while concentrating in vacuo to 48-64 L to remove tetrahydrofuran. The solution was heated to ca. 63° C., stirred for 3.5 h, before being cooled to ca. 3° C. and stirred for 8 h. The solid was isolated by centrifuge and washed with methanol (24 kg).

$3^{rd}$ cycle to remove Palladium residues and $3^{rd}$ crystallisation: The wet solid was dissolved in tetrahydrofuran (210.0 kg) at ca. 60° C. The temperature was reduced to ca. 25° C. and silicathiol (1.8 kg) was added. The mixture was stirred at ca. 48° C. for 19.5 h before being filtered. The resulting solution was circulated through a CUNO cartridge at ca. 48° C. for 16 h before tetrahydrofuran (16 kg) was added. Methanol (201 kg) was added in three portions while concentrating in vacuo to 48-64 L to remove tetrahydrofuran. The solution was heated to ca. 63° C. and stirred for 3 h, before being cooled to ca. 3° C. and stirred for 8 h. The solid was isolated by centrifuge and washed with methanol (24 kg).

The solid product was dried for 36 h at ca. 48° C. under reduced pressure to afford 10.2 kg of the title compound in 96.0% assay and 61% th yield.
Method D In a first vessel, intermediate grade N-(2-(2-fluoro-4-((4-isopropylpiperazin-1-yl)methyl)phenyl)pyridin-4-yl)-2-methoxy-5-morpholinopyridine-3-sulfonamide (8.0 kg corrected by assay, 13.7 Mol) was dissolved in dimethylsulfoxide (53.6 kg) at ca. 73° C. The resulting solution was transferred to a second vessel.

Into the second vessel containing the dimethylsulfoxide solution was added isopropyl alcohol (20 kg) at ca. 72° C. The mixture was cooled to ca. 41° C. over 0.5 h. The mixture was cooled, seeded with authentic N-(2-(2-fluoro-4-((4-isopropylpiperazin-1-yl)methyl)phenyl)pyridin-4-yl)-2-methoxy-5-morpholinopyridine-3-sulfonamide (0.17 kg, 0.01-0.03 wt) and the resulting suspension was stirred for 18 h at ca. 41° C. Isopropyl alcohol (104.0 kg) was added over 20 h at ca. 41° C. and the suspension was stirred for 3 h. The mixture was cooled to ca. 5° C. over 8 h and aged for 8 h. The solid was isolated by centrifuge and washed with isopropyl alcohol (16.0 kg).

The solid product was dried for 36 h at ca. 41° C. under reduced pressure to afford 6.3 kg of the title compound.

Example 2

N-(2-(4-((4-(tert-Butyl)piperazin-1-yl)methyl)-2-fluorophenyl)pyridin-4-yl)-2-methoxy-5-morpholinopyridine-3-sulfonamide

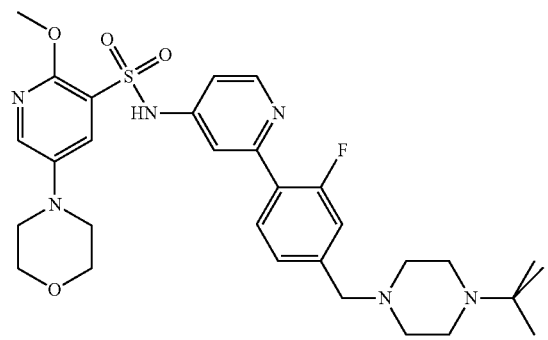 [SMILES: COc1ncc(N2CCOCC2)cc1S(=O)(=O)Nc1ccnc(-c2ccc(CN3CCN(C(C)(C)C)CC3)cc2F)c1]

A round bottomed flask was charged with N-(2-(4-((4-(tert-butyl)piperazin-1-yl)methyl)-2-fluorophenyl)pyridin-4-yl)-5-chloro-2-methoxypyridine-3-sulfonamide (3060 mg, 5.58 mmol), morpholine (1 mL, 11.43 mmol), sodium tert-butoxide (3425 mg, 35.6 mmol), Pd(OAc)$_2$ (127 mg, 0.566 mmol), RuPhos (523 mg, 1.121 mmol) and toluene (40 mL). The system was sealed, heated thermally under an atmosphere of nitrogen to 90° C. and stirred for 30 min. The reaction mixture was filtered through celite and washed with MeOH. The filtrate was concentrated under reduced pressure. The residue was dissolved in 23:3 water (containing 0.1% formic acid):MeOH and eluted on a C18 reverse-phase silica gel column using a 5% to 25% gradient of MeCN (containing 0.1% formic acid) in water (containing 0.1% formic acid). The desired fractions were concentrated under reduced pressure. The residue was dissolved in DMSO (8×3 mL), and re-purified by chromatography on a Sunfire C18 column eluting with a gradient of 5% to 25% MeCN (containing 0.1% formic acid) in water (containing 0.1% formic acid). The impure fractions were combined, concentrated under reduced pressure, then re-purified by chromatography using a Sunfire C18 column and eluting with a gradient of MeCN/water (with formic acid modifier). The desired fractions were concentrated under reduced pressure. The pure residues from the purifications were combined and eluted on a C18 reverse-phase silica gel column using a gradient of 5% to 55% MeCN (containing 0.1% NH$_3$) in water (with an ammonium bicarbonate modifier adjusted to pH 10). The desired fractions were concentrated under reduced pressure. The residue was dissolved in the minimum amount of MeOH and a white solid crystallised. The solid was collected by filtration and dried to afford the title compound (972 mg) as a white solid.

LCMS (Method A) $R_t$=0.52 min, [M+H]$^+$=599.4.

Example 3

N-(2-(4-((4-Isopropylpiperazin-1-yl)methyl)phenyl)pyridin-4-yl)-2-methoxy-5-morpholinopyridine-3-sulfonamide

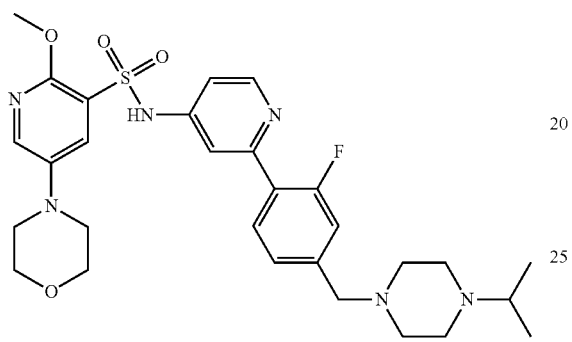

To a microwave vial was added 5-chloro-N-(2-(4-((4-isopropylpiperazin-1-yl)methyl)phenyl)pyridin-4-yl)-2-methoxypyridine-3-sulfonamide (45 mg, 0.087 mmol), morpholine (0.015 mL, 0.174 mmol) and sodium tert-butoxide (25.1 mg, 0.262 mmol), bis[tris(2-methylphenyl)phosphine]palladium (6.24 mg, 8.72 µmol), BrettPhos (9.36 mg, 0.017 mmol) and tetrahydrofuran (1 mL). The reaction vessel was sealed, purged with nitrogen and heated in a Biotage Initiator to 100° C. for 30 min. After cooling the reaction, the reaction mixture was filtered through celite and concentrated in vacuo. The residue was dissolved in 1:1 MeOH:DMSO (1 mL) and purified by Mass Directed Automated Preparative HPLC (Method A). The solvent was evaporated in vacuo and the product further dried under a stream of nitrogen in the Radleys blowdown apparatus to afford the title compound (12 mg).

LCMS (Method B) $R_t$=0.68 min, [M+H]$^+$=567.6.

Example 4

N-(2-(4-((Dimethylamino)methyl)phenyl)pyridin-4-yl)-2-methoxy-5-morpholinopyridine-3-sulfonamide

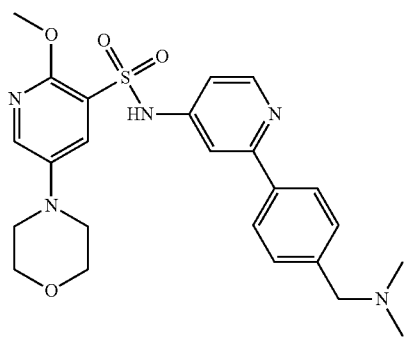 [SMILES: COc1ncc(N2CCOCC2)cc1S(=O)(=O)Nc1ccnc(-c2ccc(CN(C)C)cc2)c1]

A microwave vial was charged with 5-chloro-N-(2-(4-((dimethylamino)methyl)phenyl)pyridin-4-yl)-2-methoxypyridine-3-sulfonamide (100 mg, 0.231 mmol), morpholine (0.040 mL, 0.462 mmol) and DavePhos (13.64 mg, 0.035 mmol), sodium tert-butoxide (133 mg, 1.386 mmol), Pd$_2$(dba)$_3$ (10.58 mg, 0.012 mmol) and tetrahydrofuran (4 mL). The reaction vessel was sealed and heated in a Biotage Initiator to 120° C. for 30 min. After cooling the reaction, the reaction mixture was filtered through celite and concentrated in vacuo to afford the crude product. The residue was dissolved in 1:1 MeOH:DMSO (1 mL) and purified by Mass Directed Automated Preparative HPLC (Method B). The solvent was evaporated in vacuo to give the crude product (69 mg). The product was dissolved in 1:1 MeOH:DMSO and repurified by C18 reverse-phase silica gel chromatography using an MeCN:H$_2$O (with an ammonium bicarbonate modifier adjusted to pH 10) solvent system (chromatography performed to remove residual formic acid from the first purification). The solvent was evaporated in vacuo to afford the title compound (22 mg).

LCMS (Method A) $R_t$=0.43 min, [M+H]$^+$=484.1.

Example 5

N-(2-(3-Fluoro-4-((4-isopropylpiperazin-1-yl)methyl)phenyl)pyridin-4-yl)-2-methoxy-5-morpholinopyridine-3-sulfonamide

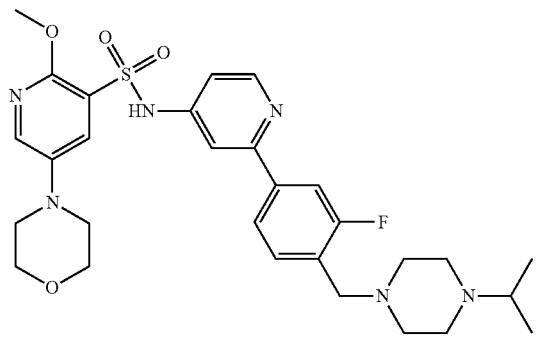

A vial was charged with 5-chloro-N-(2-(3-fluoro-4-((4-isopropylpiperazin-1-yl)methyl)phenyl)pyridin-4-yl)-2-methoxypyridine-3-sulfonamide (49 mg, 0.092 mmol), morpholine (0.017 mL, 0.194 mmol), Pd(OAc)$_2$ (2.5 mg, 0.011 mmol), sodium tert-butoxide (52 mg, 0.541 mmol) and RuPhos (9 mg, 0.019 mmol) in toluene (1 mL). The reaction vessel was sealed and heated thermally to 90° C. overnight. The reaction was stopped, the solvent removed in vacuo and the residue was dissolved in 1:1 MeOH:DMSO (1 mL) and purified by Mass Directed Automated Preparative HPLC (Method B). The solvent was dried under a stream of nitrogen in the Radleys blowdown apparatus to give the crude product, presumed as the formic salt. The sample was dissolved in MeOH and purified by reverse phase (C18) column chromatography eluting with a gradient of 0 to 40% MeCN (containing 0.1% NH$_3$) in water (with an ammonium bicarbonate modifier adjusted to pH 10). The appropriate fractions were combined and evaporated in vacuo to afford the title compound (15.4 mg).

LCMS (Method A) $R_t$=0.52 min, [M+H]$^+$=585.3.

Example 6

N-(2-(4-((4-(tert-Butyl)piperazin-1-yl)methyl)phenyl)pyridin-4-yl)-2-methoxy-5-morpholinopyridine-3-sulfonamide

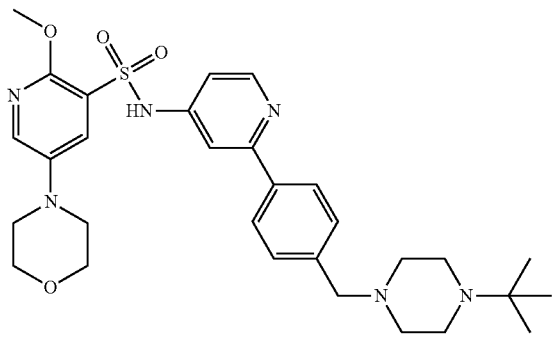 [SMILES: COc1ncc(N2CCOCC2)cc1S(=O)(=O)Nc1ccnc(-c2ccc(CN3CCN(C(C)(C)C)CC3)cc2)c1]

A vial was charged with N-(2-(4-((4-(tert-butyl)piperazin-1-yl)methyl)phenyl)pyridin-4-yl)-5-chloro-2-methoxypyridine-3-sulfonamide (100 mg, 0.189 mmol), morpholine (0.04 mL, 0.464 mmol), sodium tert-butoxide (109 mg, 1.132 mmol), Pd(OAc)$_2$ (4.24 mg, 0.019 mmol), RuPhos (17.61 mg, 0.038 mmol), and toluene (5 mL). The vial was heated at 90° C. thermally for 2 h. The reaction mixture was filtered through celite and washed with MeOH. The filtrate was concentrated under reduced pressure. The residue was dissolved in MeOH (2×1 mL) and purified by Mass Directed Automated Preparative HPLC (Method B). The desired fractions were concentrated under reduced pressure, then the residue was dissolved in MeOH (2×1 mL) and repurified by Mass Directed Automated Preparative HPLC (Method A). The desired fractions were concentrated under reduced pressure to afford the title compound (41 mg) as a white solid.

LCMS (Method A) R$_t$=0.50 min, [M+H]$^+$=581.6.

Example 7

N-(2-(4-((4-Cyclobutylpiperazin-1-yl)methypphenyl)pyridin-4-yl)-2-methoxy-5-morpholinopyridine-3-sulfonamide

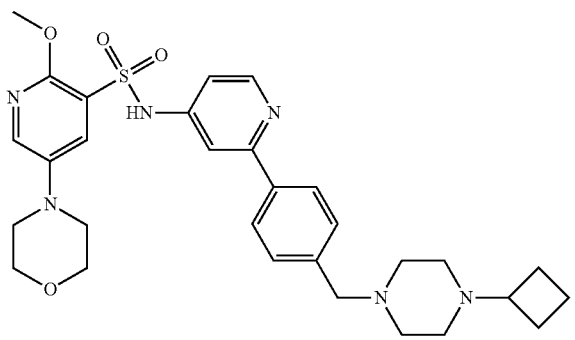 [SMILES: COc1ncc(N2CCOCC2)cc1S(=O)(=O)Nc1ccnc(-c2ccc(CN3CCN(C4CCC4)CC3)cc2)c1]

A vial was charged with 5-chloro-N-(2-(4-((4-cyclobutylpiperazin-1-yl)methyl)phenyl)pyridin-4-yl)-2-methoxypyridine-3-sulfonamide (103.5 mg, 0.196 mmol), morpholine (0.04 mL, 0.464 mmol), sodium tert-butoxide (113 mg, 1.176 mmol), Pd(OAc)$_2$ (4.40 mg, 0.020 mmol), RuPhos (18.29 mg, 0.039 mmol), and toluene (5 mL). The vial was heated at 90° C. thermally for 2 h. The reaction mixture was filtered through celite and washed with MeOH. The filtrate was concentrated under reduced pressure. The residue was dissolved in MeOH (2×1 mL) and purified by Mass Directed Automated Preparative HPLC (Method B). The desired fractions were concentrated under reduced pressure, then the residue was dissolved in MeOH (1×1 mL) and repurified by Mass Directed Automated Preparative HPLC (Method A). The desired fractions were concentrated under reduced pressure to afford the title compound (47 mg) as a cream-coloured solid.

LCMS (Method A) R$_t$=0.50 min, [M+H]$^+$=579.6.

Example 8

N-(2-(2,6-Difluoro-4-((4-isopropylpiperazin-1-yl)methyl)phenyl)pyridin-4-yl)-2-methoxy-5-morpholinopyridine-3-sulfonamide

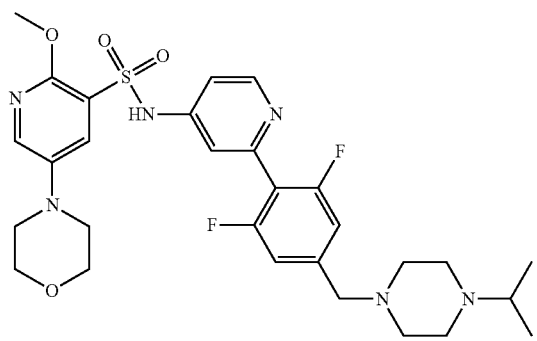

A vial was charged with 5-chloro-N-(2-(2,6-difluoro-4-((4-isopropylpiperazin-1-yl)methyl)phenyl)pyridin-4-yl)-2-methoxypyridine-3-sulfonamide (70 mg, 0.127 mmol), morpholine (0.03 mL, 0.348 mmol), sodium tert-butoxide (73 mg, 0.760 mmol), Pd(OAc)$_2$ (3 mg, 0.013 mmol), RuPhos (12 mg, 0.026 mmol), and toluene (4 mL). The vial was heated at 90° C. thermally for 2.5 h and left standing at room temperature overnight. The reaction mixture was concentrated under reduced pressure. The residue was dissolved in MeOH (2×1 mL) and purified purified by Mass Directed Automated Preparative HPLC (Method B). The desired fractions were concentrated under nitrogen blowdown, then the residue was purified by chromatography on reverse phase C18 silica eluting with a gradient of 5% to 85% MeCN (containing 0.1% NH$_3$) in water (with an ammonium bicarbonate modifier adjusted to pH 10) to afford, after concentration of the desired fractions under reduced pressure, the title compound (32 mg) as a white solid.

LCMS (Method A) R$_t$=0.57 min, [M+H]$^+$=603.5.

Example 9

N-(2-(4-((4-(sec-Butyl)piperazin-1-yl)methyphenyl)pyridin-4-yl)-2-methoxy-5-morpholinopyridine-3-sulfonamide

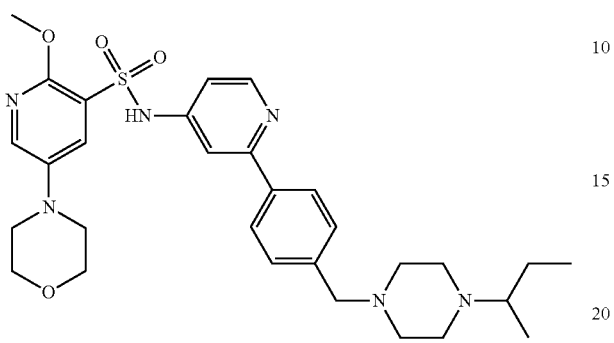

Morpholine (0.066 mL, 0.755 mmol), N-(2-(4-((4-(sec-butyl)piperazin-1-yl)methyl)phenyl)pyridin-4-yl)-5-chloro-2-methoxypyridine-3-sulfonamide (200 mg, 0.377 mmol), sodium tert-butoxide (218 mg, 2.264 mmol), Pd(OAc)$_2$ (8.47 mg, 0.038 mmol) and RuPhos (35.2 mg, 0.075 mmol) were added to a vial followed by toluene (2 mL). The vial was sealed and heated to 90° C. for 18 h. The reaction mixture was then concentrated in vacuo, the residue was dissolved in 1:1 MeOH:DMSO (3×1 mL) and purified by Mass Directed Automated Preparative HPLC (Method B). The desired fractions were concentrated in vacuo, the crude product was dissolved in 1:1 MeOH:DMSO (2×1 mL) and repurified by Mass Directed Automated Preparative HPLC (Method A). The desired fractions were concentrated in vacuo to afford the title compound (109.6 mg).

LCMS (Method B) R$_t$=0.82 min, [M+H]$^+$=581.7.

Example 10

N-(2-(2-Fluoro-4-(pyrrolidin-1-ylmethyl)phenyl)pyridin-4-yl)-2-methoxy-5-morpholinopyridine-3-sulfonamide

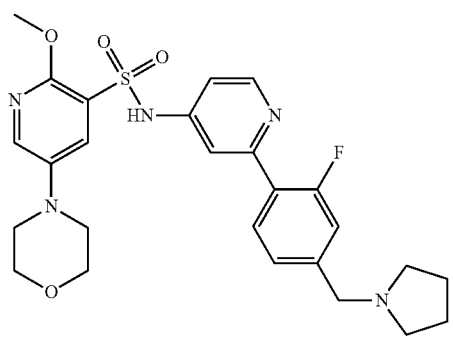 [SMILES: COc1ncc(N2CCOCC2)cc1S(=O)(=O)Nc1ccnc(-c2ccc(CN3CCCC3)cc2F)c1]

A microwave vial was charged with 5-chloro-N-(2-(2-fluoro-4-(pyrrolidin-1-ylmethyl)phenyl)pyridin-4-yl)-2-methoxypyridine-3-sulfonamide (309 mg, 0.648 mmol), morpholine (0.113 mL, 1.296 mmol), sodium tert-butoxide (375 mg, 3.90 mmol), Pd(OAc)$_2$ (16 mg, 0.071 mmol), RuPhos (60.5 mg, 0.130 mmol) and toluene (5 mL). The system was sealed, heated thermally under an atmosphere of nitrogen to 90° C. and left to stir for 30 min. The reaction mixture was filtered through celite and washed with MeOH. The filtrate was concentrated under reduced pressure. The residue was dissolved in DMSO (4 mL) and purified by Mass Directed Automated Preparative HPLC (Method B). The desired fractions were concentrated under reduced pressure. The residue was then dissolved in DMSO (1 mL) and repurified by chromatography on reverse phase C18 silica eluting with a gradient of 5% to 55% MeCN (containing 0.1% NH$_3$) in water (with an ammonium bicarbonate modifier adjusted to pH 10). The desired fractions were concentrated under reduced pressure. The residue was dissolved in the minimum amount of MeOH, the precipitate which formed was collected by filtration and dried to afford the title compound (82 mg) as a white solid.

LCMS (Method A) R$_t$=0.47 min, [M+H]$^+$=528.2.

Example 11

N-(2-(3-Fluoro-4-(pyrrolidin-1-ylmethyl)phenyl)pyridin-4-yl)-2-methoxy-5-morpholinopyridine-3-sulfonamide

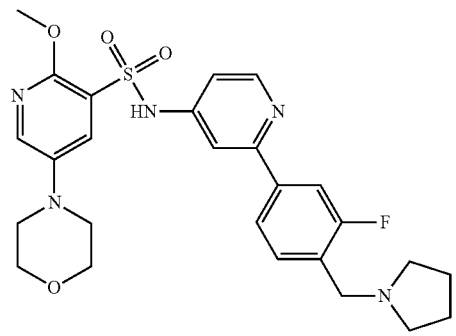 [SMILES: COc1ncc(N2CCOCC2)cc1S(=O)(=O)Nc1ccnc(-c2ccc(CN3CCCC3)c(F)c2)c1]

5-Chloro-N-(2-(3-fluoro-4-(pyrrolidin-1-yl methyl)phenyl)pyridin-4-yl)-2-methoxypyridine-3-sulfonamide (39 mg, 0.082 mmol), sodium tert-butoxide (47.1 mg, 0.491 mmol), Pd(OAc)$_2$ (1.836 mg, 8.18 µmol), RuPhos (7.63 mg, 0.016 mmol), morpholine (0.019 mL, 0.221 mmol) and toluene (2 mL) were added to a vial. The vial was sealed and heated at 90° C. for 3 h. Additional portions of palladium acetate (5 mg, 0.022 mmol) and RuPhos (8 mg, 0.017 mmol) were added and the reaction mixture was stirred at 90° C. for 1.5 h. MeOH (6 mL) was added and the reaction mixture filtered through celite and washed with MeOH (6 mL). The solvent was removed in vacuo. The residue was dissolved in DMSO (1 mL) and purified by Mass Directed Automated Preparative HPLC (Method B). The desired fractions were evaporated by nitrogen blowdown. The residue was repurified by chromatography on reverse phase C18 silica eluting with a gradient of 5% to 80% MeCN (containing 0.1% NH$_3$) in water (with an ammonium bicarbonate modifier adjusted to pH 10). The appropriate fractions were combined and concentrated in vacuo to afford the title compound (10 mg) as a white solid.

LCMS (Method A) R$_t$=0.52 min, [M+H]$^+$=528.5.

Example 12

N-(2-(3,5-Difluoro-4-((4-isopropylpiperazin-1-yl)methyl)phenyl)pyridin-4-yl)-2-methoxy-5-morpholinopyridine-3-sulfonamide

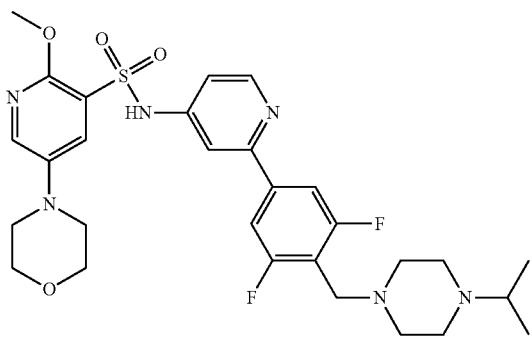 [SMILES: COc1ncc(N2CCOCC2)cc1S(=O)(=O)Nc1ccnc(-c2cc(F)c(CN3CCN(C(C)C)CC3)c(F)c2)c1]

5-Chloro-N-(2-(3,5-difluoro-4-((4-isopropylpiperazin-1-yl)methyl)phenyl)pyridin-4-yl)-2-methoxypyridine-3-sulfonamide (50 mg, 0.091 mmol), sodium tert-butoxide (51 mg, 0.531 mmol), Pd(OAc)$_2$ (5 mg, 0.022 mmol), RuPhos (9 mg, 0.019 mmol), morpholine (0.021 mL, 0.245 mmol) and toluene (2 mL) were added to a vial. The vial was sealed and heated at 90° C. for 2.5 h. The solvent was evaporated and the residue disolved in DMSO (1 mL) and purified by Mass Directed Automated Preparative HPLC (Method B). The desired fractions were evaporated by nitrogen blowdown. The residue was repurified by chromatography on reverse phase C18 silica eluting with a gradient of 5% to 80% MeCN (containing 0.1% NH$_3$) in water (with an ammonium bicarbonate modifier adjusted to pH 10). The appropriate fractions were combined and concentrated in vacuo to afford the title compound (22 mg) as a white solid.

LCMS (Method A) R$_t$=0.60 min, [M+H]$^+$=603.5.

Example 13

2-Methoxy-5-morpholino-N-(2-(4-((4-(oxetan-3-yl)piperazin-1-yl)methyl)phenyppyridin-4-yl)pyridine-3-sulfonamide

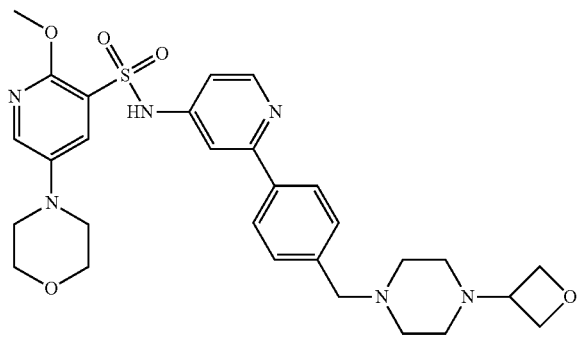 [SMILES: COc1ncc(N2CCOCC2)cc1S(=O)(=O)Nc1ccnc(-c2ccc(CN3CCN(C4COC4)CC3)cc2)c1]

A vial was charged with 5-chloro-2-methoxy-N-(2-(4-((4-(oxetan-3-yl)piperazin-1-yl)methyl)phenyl)pyridin-4-yl)pyridine-3-sulfonamide (90 mg, 0.170 mmol), morpholine (30 μL, 0.348 μmol), sodium tert-butoxide (82 mg, 0.849 mmol), Pd(OAc)$_2$ (4 mg, 0.018 mmol) and RuPhos (16 mg, 0.034 mmol) in toluene (1 mL). The vial was sealed and heated to 90° C. for 6 h. The reaction was cooled, filtered through celite, the solid washed through with MeOH (30 mL) and the filtrate evaporated in vacuo. The residue was dissolved in 1:1 MeOH:DMSO (2×1 mL) and purified by Mass Directed Automated Preparative HPLC (Method B). The solvent was removed under a stream of nitrogen in the Radleys blowdown apparatus to give the required product, presumed as the formic acid salt. The residue was dissolved in DMSO and repurified by reverse phase C18 silica chromatography eluting with a gradient of 0 to 50% MeCN (containing 0.1% NH$_3$) in water (with an ammonium bicarbonate modifier adjusted to pH 10). The appropriate fractions were combined and evaporated in vacuo to afford the title compound (19 mg).

LCMS (Method A) R$_t$=0.46 min, [M+H]$^+$=581.5.

Example 14

N-(2-(2,3-Difluoro-4-((4-isopropylpiperazin-1-yl)methyl)phenyl)pyridin-4-yl)-2-methoxy-5-morpholinopyridine-3-sulfonamide

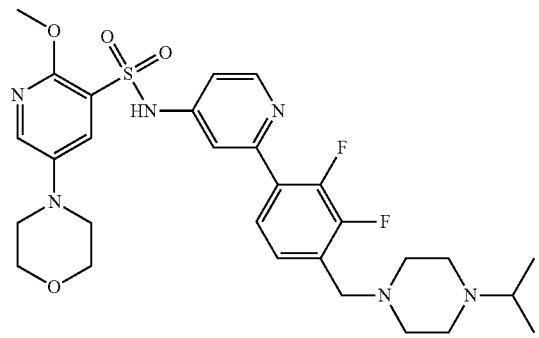

5-Ch loro-N-(2-(2,3-difluoro-4-((4-isopropylpiperazin-1-yl)methyl)phenyl)pyridin-4-yl)-2-methoxypyridine-3-sulfonamide (160 mg, 0.290 mmol), morpholine (0.068 mL, 0.783 mmol), sodium tert-butoxide (167 mg, 1.739 mmol), Pd(OAc)$_2$ (13.01 mg, 0.058 mmol), RuPhos (27.0 mg, 0.058 mmol) and toluene (2 mL) were added to a vial. The vial was sealed and heated theremally to 90° C. for 3 h. The reaction mixture was filtered through celite and washed with MeOH (40 mL). The filtrate was concentrated and the residue was disolved in DMSO (1 mL) and purified by Mass Directed Automated Preparative HPLC (Method B). The desired fractions were evaporated by nitrogen blowdown. The residue was repurified by reverse phase C18 silica chromatography eluting with a gradient of 0 to 80% MeCN (containing 0.1% NH$_3$) in water (with an ammonium bicarbonate modifier adjusted to pH 10). The appropriate fractions were combined and concentrated in vacuo to afford the title compound (24 mg) as a pale yellow solid.

LCMS (Method A) R$_t$=0.57 min, [M+H]$^+$=603.6.

Example 15

N-(2-(2-Fluoro-4-((4-(oxetan-3-yl)piperazin-1-yl)methyl)phenyl)pyridin-4-yl)-2-methoxy-5-morpholinopyridine-3-sulfonamide, 3 formic acid salt

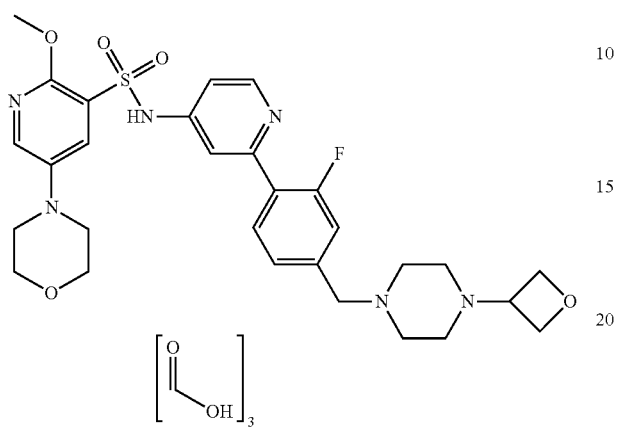

A vial was charged with 5-chloro-N-(2-(2-fluoro-4-((4-(oxetan-3-yl)piperazin-1-yl)methyl)phenyl)pyridin-4-yl)-2-methoxypyridine-3-sulfonamide (51 mg, 0.093 mmol), morpholine (0.020 mL, 0.229 mmol), sodium tert-butoxide (53 mg, 0.551 mmol), Pd(OAc)$_2$ (2.2 mg, 9.80 μmol) and RuPhos (9 mg, 0.019 mmol) and toluene (2 mL). The vial was sealed, heated to 90° C. for 2 h. Additional portions of morpholine (0.020 mL, 0.229 mmol), Pd(OAc)$_2$ (2.2 mg, 9.80 μmol) and RuPhos (9 mg, 0.019 mmol) were added and the reaction stirred overnight. The solvent was removed in vacuo and the residue was dissolved in 1:1 MeOH:DMSO (1 mL) and purified by Mass Directed Automated Preparative HPLC (Method B). The solvent was dried under a stream of nitrogen in the Radleys blowdown apparatus to afford the title compound (15 mg) as an off-white solid.

LCMS (Method B) R$_t$=0.60 min, [M+H]$^+$=599.6.

Example 16

N-(2-(4-((4-Cyclobutylpiperazin-1-yl)methyl)-2-fluorophenyppyridin-4-yl)-2-methoxy-5-morpholinopyridine-3-sulfonamide, 2.5 formic acid salt

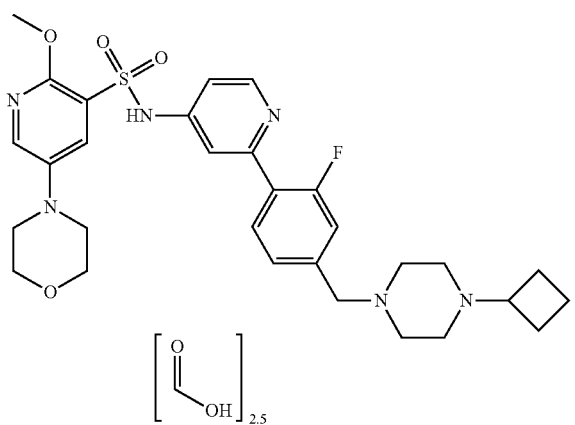

A vial was charged with 5-chloro-N-(2-(4-((4-cyclobutylpiperazin-1-yl)methyl)-2-fluorophenyl)pyridin-4-yl)-2-methoxypyridine-3-sulfonamide (48 mg, 0.088 mmol), morpholine (0.020 mL, 0.229 mmol), sodium tert-butoxide (51 mg, 0.531 mmol), Pd(OAc)$_2$ (2.0 mg, 8.91 μmol) and RuPhos (8.6 mg, 0.018 mmol) in toluene (2 mL). The vial was sealed, heated to 90° C. for 2 h. The solvent was removed in vacuo and the residue was dissolved in 1:1 MeOH:DMSO (1 mL) and purified by Mass Directed Automated Preparative HPLC (Method B). The solvent was dried under a stream of nitrogen in the Radleys blowdown apparatus to afford the title compound (12 mg), as an off-white solid.

LCMS (Method B) R$_t$=0.74 min, [M+H]$^+$=597.5.

Example 17

N-(2-(2,5-Difluoro-4-((4-isopropylpiperazin-1-yl)methyl)phenyl)pyridin-4-yl)-2-methoxy-5-morpholinopyridine-3-sulfonamide

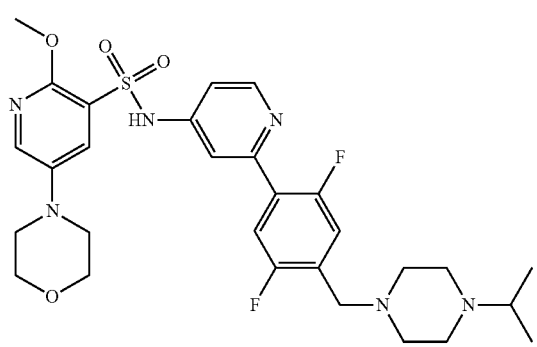

A mixture of 5-chloro-N-(2-(2,5-difluoro-4-((4-isopropylpiperazin-1-yl)methyl)phenyl)pyridin-4-yl)-2-methoxypyridine-3-sulfonamide (516 mg, 0.935 mmol), morpholine (0.164 mL, 1.869 mmol), sodium tert-butoxide (539 mg, 5.61 mmol), Pd(OAc)$_2$ (20.99 mg, 0.093 mmol), RuPhos (87 mg, 0.187 mmol) and toluene (5 mL) was heated thermally to 90° C. under an atmosphere of nitrogen for 3 h. The reaction mixture was cooled to room temperature, filtered through celite and washed with MeOH. The filtrate was concentrated under reduced pressure. The residue was purified by C18 reverse-phase silica gel column eluting with a gradient of 5% to 25% MeCN (containing 0.1% formic acid) in water (containing 0.1% formic acid). The desired fractions were concentrated under reduced pressure. The residue was repurified by reverse phase preparative chromatography using a Sunfire C18 column eluting with a gradient of 5% to 35% MeCN (containing 0.1% formic acid) in water (containing 0.1% formic acid). The desired fractions were concentrated under reduced pressure and the residue was repurified by reverse phase C18 silica chromatography eluting with a gradient of 5% to 55% MeCN (containing 0.1% NH$_3$) in water (with an ammonium bicarbonate modifier adjusted to pH 10). The collected fractions were concentrated under reduced pressure and dried in the oven (40° C.) for 72 h to afford the title compound (139 mg) as an off-white solid.

LCMS (Method A) R$_t$=0.57 min, [M+H]$^+$=603.4.

Example 18

N-(2-(2-Fluoro-4-((4-(2-methoxyethyl)piperazin-1-yl)methyl)phenyl)pyridin-4-yl)-2-methoxy-5-morpholinopyridine-3-sulfonamide, 1.2 formic acid salt

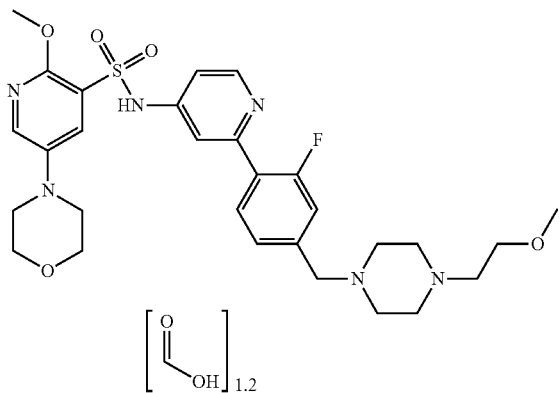

To a stirred suspension of N-(2-(2-fluoro-4-formylphenyl)pyridin-4-yl)-2-methoxy-5-morpholinopyridine-3-sulfonamide (40 mg, 0.085 mmol) in MeOH (0.45 mL) and acetic acid (0.05 mL), was added 1-(2-methoxyethyl)piperazine (14.42 mg, 0.100 mmol). The resulting solution was stirred for 30 min when 2-picolineborane (13.58 mg, 0.127 mmol) was added and the solution stirred at 50° C. overnight. After cooling, the solvent was removed by nitrogen blowdown. The residue was dissolved in 1:1 MeOH:DMSO (1 mL) and purified by Mass Directed Automated Preparative HPLC (Method B). The solvent was dried under a stream of nitrogen in the Radleys blowdown apparatus to afford the title compound (29.2 mg).

LCMS (Method A) $R_t$=0.51 min, $[M+H]^+$=601.1.

Similarly prepared were:

| Example Number | Name | Structure | Precursor | Purification Method | LCMS $R_t$ (min) | $[M + H]^+$ |
|---|---|---|---|---|---|---|
| Example 19 | N-(2-(2-fluoro-4-((3-methylpyrrolidin-1-yl)methyl)phenyl)pyridin-4-yl)-2-methoxy-5-morpholino pyridine-3-sulfonamide | 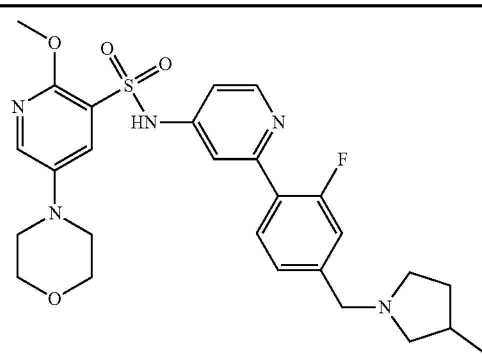 | 3-methyl-pyrrolidine | A | 0.53 | 542.1 |
| Example 20 | N-(2-(2-fluoro-4-((2-methylpyrrolidin-1-yl)methyl)phenyl)pyridin-4-yl)-2-methoxy-5-morpholino pyridine-3-sulfonamide | 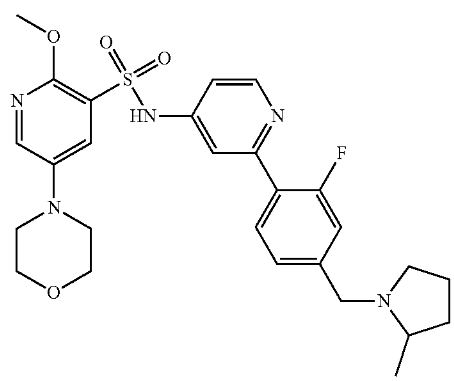 [SMILES: COc1ncc(N2CCOCC2)cc1S(=O)(=O)Nc1ccnc(-c2ccc(CN3CCCC3C)cc2F)c1] | 2-methyl-pyrrolidine | A | 0.51 | 542 |
| Example 21 | N-(2-(2-fluoro-4-(piperidin-1-ylmethyl)phenyl)pyridin-4-yl)-2-methoxy-5-morpholino pyridine-3-sulfonamide, formic acid salt | 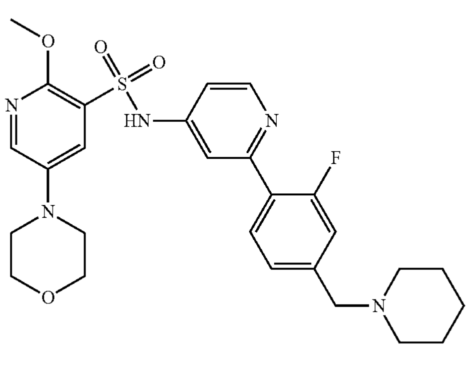 [SMILES: COc1ncc(N2CCOCC2)cc1S(=O)(=O)Nc1ccnc(-c2ccc(CN3CCCCC3)cc2F)c1] | piperidine | B | 0.52 | 542.1 |

| Example Number | Name | Structure | Precursor | Purification Method | LCMS $R_t$ (min) | $[M + H]^+$ |
|---|---|---|---|---|---|---|
| | | ![formic acid structure] | | | | |

Example 22

N-(2-(2-Fluoro-4-((4-(2-hydroxypropan-2-yl)piperidin-1-yl)methyl)phenyl)pyridin-4-yl)-2-methoxy-5-morpholinopyridine-3-sulfonamide

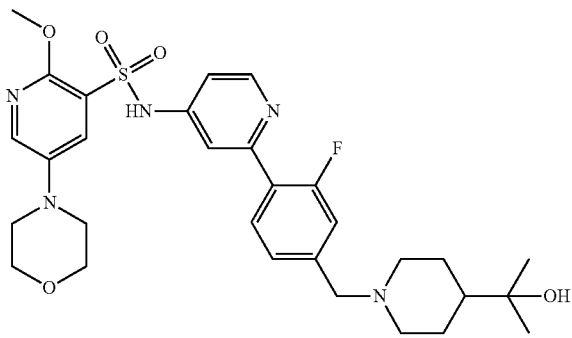 [SMILES: COc1ncc(N2CCOCC2)cc1S(=O)(=O)Nc1ccnc(-c2ccc(CN3CCC(C(C)(C)O)CC3)cc2F)c1]

To a stirred solution of N-(2-(2-fluoro-4-formylphenyl)pyridin-4-yl)-2-methoxy-5-morpholinopyridine-3-sulfonamide (99 mg, 0.210 mmol) in MeOH (1 mL) and acetic acid (0.1 mL) was added 2-(piperidin-4-yl)propan-2-ol (34 mg, 0.237 mmol) and the reaction left to stir at room temperature for 30 min, when 2-picolineborane (32 mg, 0.299 mmol) was added in one charge. After stirring over the weekend, the solvent was removed in vacuo and the residue dissolved in 1:1 MeOH:DMSO (2×1 mL) and purified by Mass Directed Automated Preparative HPLC (Method A). The solvent was evaporated in vacuo to afford the title compound (82 mg) as a white solid.

LCMS (Method B) $R_t$=0.69 min, $[M+H]^+$=600.2.

Example 23

N-(2-(4-(((cis)-2,6-Dimethylmorpholino)methyl)phenyl)pyridin-4-yl)-2-methoxy-5-morpholinopyridine-3-sulfonamide

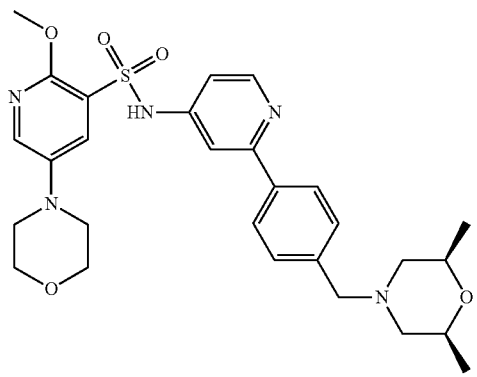 [SMILES: COc1ncc(N2CCOCC2)cc1S(=O)(=O)Nc1ccnc(-c2ccc(CN3C[C@@H](C)O[C@@H](C)C3)cc2)c1]

To a solution of (4-(bromomethyl)phenyl)boronic acid (1 g, 4.65 mmol), in 2-methyltetrahydrofuran (15 mL) was added (cis)-2,6-dimethylmorpholine (0.536 g, 4.65 mmol) at room temperature. The reaction mixture was stirred at room temperature for 2 h. The reaction mixture was filtered through celite, washed with EtOAc (50 mL) and the filtrate was evaporated to crude (4-(((cis)-2,6-dimethylmorpholino)methyl)phenyl)boronic acid (1.6 g).

To a stirred solution of N-(2-chloropyridin-4-yl)-2-methoxy-5-morpholinopyridine-3-sulfonamide (250 mg, 0.650 mmol) in 1,4-dioxane (8 mL) and water (2 mL), was added a portion of the crude (4-(((cis)-2,6-dimethylmorpholino)methyl)phenyl)boronic acid (405 mg), $K_3PO_4$ (344 mg, 1.624 mmol) at room temperature. The reaction mixture was degassed for 30 min at room temperature. Xphos precatalyst $2^{nd}$ generation (51.1 mg, 0.065 mmol) was added at room temperature and the reaction mixture was degassed again for 30 min at room temperature. The sealed tube was stirred for 18 h at 110° C. The reaction mixture was filtered through celite and washed with EtOAc (100 mL). The filtrate was evaporated and the residue (500 mg) was purified by Preparative-HPLC (Method B). Collected fractions were lyophilized to afford the title compound (54 mg) as a white solid.

LCMS (Method G) $R_t$=1.40 min, $[M+H]^+$=554.3.

Example 24

2-Methoxy-5-morpholino-N-(2-(4-(morpholinomethyl)phenyl)pyridin-4-yl)pyridine-3-sulfonamide

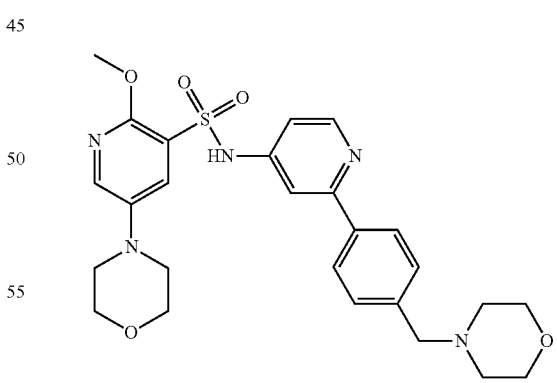

To a solution of (4-(bromomethyl)phenyl)boronic acid (1 g, 4.65 mmol), in 2-methyltetrahydrofuran (15 mL) was added morpholine (0.405 g, 4.65 mmol) at room temperature. The reaction mixture was stirred at room temperature for 2 h. The reaction mixture was filtered on celite, washed with EtOAc (50 mL) and the filtrate was evaporated to afford crude (4-(morpholinomethyl)phenyl)boronic acid (1.5 g).

To a stirred solution of N-(2-chloropyridin-4-yl)-2-methoxy-5-morpholinopyridine-3-sulfonamide (250 mg, 0.650 mmol) in 1,4-dioxane (8 mL) and water (2 mL), was added a portion of crude (4-(morpholinomethyl)phenyl)boronic acid (359 mg, 1.624 mmol), K₃PO₄ (344 mg, 1.624 mmol) at room temperature. The reaction mixture was degassed for 30 min at room temperature. Xphos precatalyst 2$^{nd}$ generation (25.5 mg, 0.032 mmol) was added at room temperature. The reaction mixture was degassed again for 30 min at room temperature. The sealed tube was stirred for 18 h at 110° C. The reaction mixture was filtered through celite, washed with EtOAc (100 mL) and the filtrate was evaporated. The residue (400 mg) was purified by Preparative-HPLC (Method C). Collected fractions were lyophilized to afford the title compound (116 mg) as a white solid.

LCMS (Method G) $R_t$=1.29 min, [M+H]$^+$=526.3.

Example 25

N-(2-(2-Fluoro-4-(piperazin-1-ylmethyl)phenyl)pyridin-4-yl)-2-methoxy-5-morpholinopyridine-3-sulfonamide

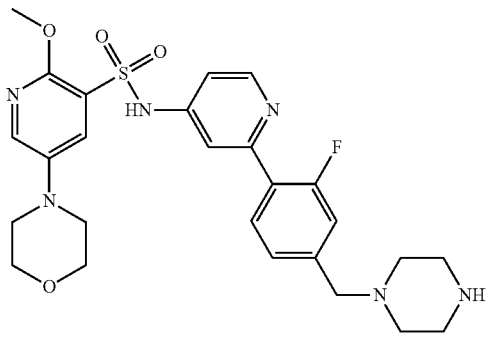 [SMILES: COc1ncc(N2CCOCC2)cc1S(=O)(=O)Nc1ccnc(-c2ccc(CN3CCNCC3)cc2F)c1]

A round bottomed flask was charged with tert-butyl 4-(3-fluoro-4-(4-(2-methoxy-5-morpholinopyridine-3-sulfonamido)pyridin-2-yl)benzyl)piperazine-1-carboxylate (1128 mg, 1.755 mmol) and DCM (10 mL). Trifluoroacetic acid (1.5 mL, 19.60 mmol) was then added, the vessel was sealed and the reaction was stirred at room temperature for 16 h. The reaction mixture was concentrated under reduced pressure. The residue was dissolved in 4:9 DMSO:water (with an ammonium bicarbonate modifier adjusted to pH 10) and eluted on a C18 reverse-phase silica gel column using a gradient of 5% to 95% MeCN (containing 0.1% NH3) in water (with an ammonium bicarbonate modifier adjusted to pH 10). The desired fractions were concentrated under reduced pressure, dissolved in the minimum amount of 50:50 DCM:MeOH and the precipitate which formed, was collected by filtration and dried to afford the title compound (763 mg) as a white solid.

LCMS (Method A) $R_t$=0.45 min, [M+H]$^+$=543.3.

Example 26

2-(Dimethylamino)-N-(2-(2-fluoro-4-((4-isopropylpiperazin-1-yl)methyl)phenyl)pyridin-4-yl)-5-morpholinopyridine-3-sulfonamide

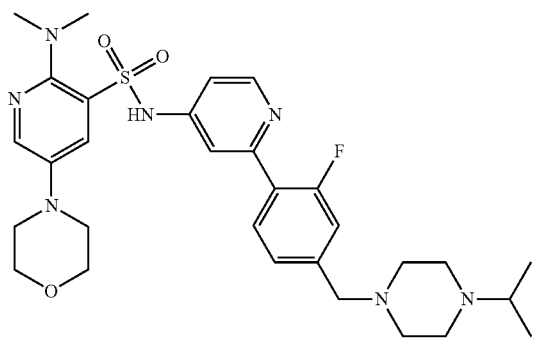 [SMILES: CC(C)N1CCN(Cc2ccc(-c3cc(NS(=O)(=O)c4cc(N5CCOCC5)cnc4N(C)C)ccn3)c(F)c2)CC1]

A vial was charged with morpholine (0.064 mL, 0.731 mmol), sodium tert-butoxide (176 mg, 1.828 mmol) and 5-chloro-2-(dimethylamino)-N-(2-(2-fluoro-4-((4-isopropylpiperazin-1-yl)methyl)phenyl)pyridin-4-yl)pyridine-3-sulfonamide (200 mg, 0.366 mmol) in dry tetrahydrofuran (10 mL). The reaction mixture was degassed using argon for 30 min and 2'-(dicyclohexylphosphino)-N,N-dimethyl-[1,1'-biphenyl]-2-amine (23.02 mg, 0.058 mmol) was added followed by Pd₂(dba)₃ (16.74 mg, 0.018 mmol). The reaction vessel was sealed and heated in Anton Parr microwave to 120° C. for 40 min. The reaction mixture was filtered through celite, washed with 10% MeOH/DCM (10 mL) and the filtrate was evaporated. The residue (350 mg) was purified by Preparative-HPLC (Method F). Collected fractions were lyophilized to afford the title compound (97 mg) as pale yellow solid.

LCMS (Method H) $R_t$=2.96 min, [M+H]$^+$=598.3.

Example 27

N-(2-(4-((4-(tert-Butyl)piperazin-1-yl)methyl)-2-fluorophenyl)pyridin-4-yl)-2-(dimethylamino)-5-morpholinopyridine-3-sulfonamide

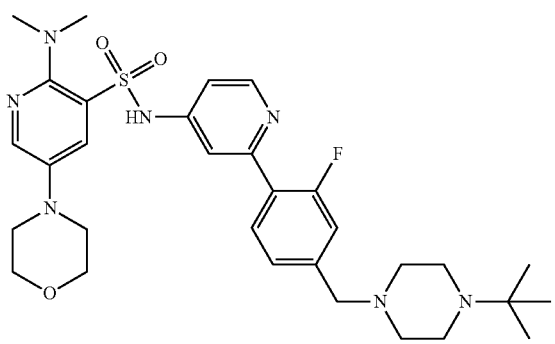 [SMILES: CN(C)c1ncc(N2CCOCC2)cc1S(=O)(=O)Nc1ccnc(-c2ccc(CN3CCN(C(C)(C)C)CC3)cc2F)c1]

A sealed tube was charged with morpholine (0.078 mL, 0.891 mmol), sodium tert-butoxide (214 mg, 2.228 mmol) and N-(2-(4-((4-(tert-butyl)piperazin-1-yl)methyl)-2-fluorophenyl)pyridin-4-yl)-5-chloro-2-(dimethylamino)pyridine-3-sulfonamide (250 mg, 0.446 mmol) in dry tetrahydrofuran (10 mL). The reaction mixture was degassed using argon for 30 min and 2'-(dicyclohexylphosphino)-N,N-dimethyl-[1,1'- biphenyl]-2-amine (28.1 mg, 0.071 mmol) was added followed by $Pd_2(dba)_3$ (20.40 mg, 0.022 mmol). The resulting reaction mixture was stirred at 120° C. for 40 min. The reaction mixture was filtered, washed with 10% MeOH/DCM (10 mL) and the filtrate was evaporated. The residue (450 mg) was purified by Preparative-HPLC (Method H). The desired fractions were lyophilized to afford the title compound (50 mg) as a pale yellow solid.

LCMS (Method H) $R_t$=3.11 min, $[M+H]^+$=612.3.

Example 28

N-(2-(4-((4-(tert-Butyl)piperazin-1-yl)methyl)-2-fluorophenyl)pyridin-4-yl)-2-methoxy-N-methyl-5-morpholinopyridine-3-sulfonamide

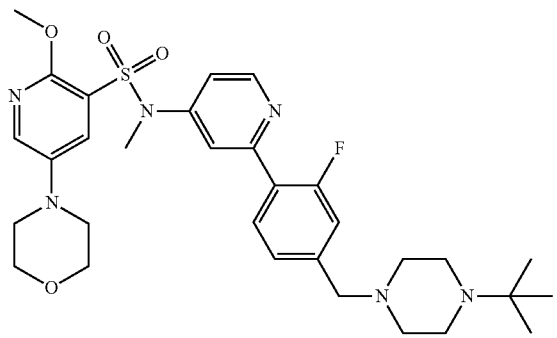 [SMILES: COc1ncc(N2CCOCC2)cc1S(=O)(=O)N(C)c1ccnc(-c2ccc(CN3CCN(C(C)(C)C)CC3)cc2F)c1]

N-(2-(4-((4-(tert-Butyl)piperazin-1-yl)methyl)-2-fluorophenyl)pyridin-4-yl)-2-methoxy-5-morpholinopyridine-3-sulfonamide (100 mg, 0.167 mmol) was dissolved in DMF (2 mL) and was treated with potassium carbonate (27.7 mg, 0.200 mmol). 10 min later, iodomethane (0.013 mL, 0.200 mmol) was added. The reaction mixture was stirred at room temperature for 18 h. The reaction mixture was then concentrated in vacuo, the residue was dissolved in 1:1 MeOH:DMSO (1 mL) and purified by Mass Directed Automated Preparative HPLC (Method A). The solvent was dried under a stream of nitrogen in the Radleys blowdown apparatus to afford the title compound (42.3 mg).

LCMS (Method B) $R_t$=1.25 min, $[M+H]^+$=613.2.

Example 29

N-(2-(2-Fluoro-4-((4-isopropylpiperazin-1-yl)methyl)phenyl)pyridin-4-yl)-2-methoxy-N-methyl-5-morpholinopyridine-3-sulfonamide

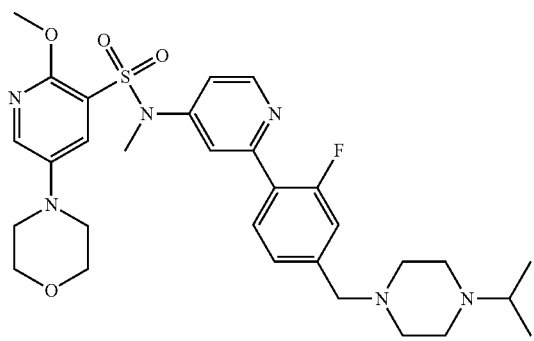 [SMILES: COc1ncc(N2CCOCC2)cc1S(=O)(=O)N(C)c1ccnc(-c2ccc(CN3CCN(C(C)C)CC3)cc2F)c1]

5-Chloro-N-(2-(2-fluoro-4-((4-isopropylpiperazin-1-yl)methyl)phenyl)pyridin-4-yl)-2-methoxy-N-methylpyridine-3-sulfonamide (150 mg, 0.274 mmol), sodium tert-butoxide (132 mg, 1.368 mmol), morpholine (0.048 mL, 0.547 mmol), $Pd_2(dba)_3$ (12.53 mg, 0.014 mmol) and Davephos (16.16 mg, 0.041 mmol) were added to a microwave vial followed by tetrahydrofuran (5 mL). The vial was sealed and heated to 120° C. for 30 min in the microwave apparatus. The same procedure was repeated (on the exact same scale) to produce more crude material. The reaction mixtures form the 2 reactions were combined and concentrated in vacuo, the residue was dissolved in 1:1 MeOH:DMSO (3×1 mL) and purified by Mass Directed Automated Preparative HPLC (Method B). The solvent was concentrated in vacuo and the residue was dissolved in 1:1 MeOH:DMSO 2×1 mL and repurified by Mass Directed Automated Preparative HPLC (Method A). The solvent was concentrated in vacuo to give a yellow gum that was transferred to a vial and left in the vacuum oven for 2 h to afford the title compound (98.7 mg) as a yellow solid.

LCMS (Method B) $R_t$=1.20 min, $[M+H]^+$=599.2.

Example 30

N-Ethyl-N-(2-(2-fluoro-4-((4-isopropylpiperazin-1-yl)methyl)phenyl)pyridin-4-yl)-2-methoxy-5-morpholinopyridine-3-sulfonamide

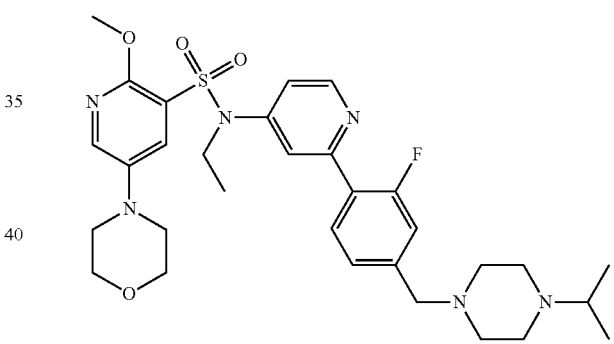

Morpholine (0.243 mL, 2.79 mmol), 5-chloro-N-ethyl-N-(2-(2-fluoro-4-((4-isopropylpiperazin-1-yl)methyl)phenyl)pyridin-4-yl)-2-methoxypyridine-3-sulfonamide (785 mg, 1.397 mmol), Davephos (82 mg, 0.209 mmol), sodium tert-butoxide (671 mg, 6.98 mmol) and $Pd_2(dba)_3$ (63.9 mg, 0.070 mmol) were added to microwave vial followed by tetrahydrofuran (12 mL). The vial was sealed and heated to 120° C. for 30 min in a microwave apparatus. The reaction mixture was then concentrated in vacuo and partitioned between EtOAc (150 mL) and saturated aqueous sodium bicarbonate (150 mL), the aqueous phase was separated and extracted with further EtOAc (150 mL). The combined organic extracts were then dried through a hydrophobic frit and concentrated in vacuo to give an orange oil. The oil was purified by ion exchange $NH_2$ SPE (50 g) eluting with a gradient of 0 to 25% EtOAc in cyclohexane. The appropriate fractions were combined and concentrated in vacuo to give a yellow oil. The yellow oil was then dissolved in 1:1 MeOH:DMSO (3×1 mL) and purified by Mass Directed Automated Preparative HPLC (Method B). The solvent was concentrated in vacuo to give an off white solid. The solid was dissolved in 1:1 MeOH:DMSO (1 mL) and repurified by Mass Directed Automated Preparative HPLC (Method A). The solvent was concentrated in vacuo to afford the title compound (222.4 mg) as a light yellow solid.

LCMS (Method B) $R_t$=1.25 min, $[M+H]^+$=613.4.

Example 31

N-(2-(2-Fluoro-4-((4-isopropylpiperazin-1-yl)methyl)phenyl)pyridin-4-yl)-2-methoxy-5-morpholino-N-propylpyridine-3-sulfonamide

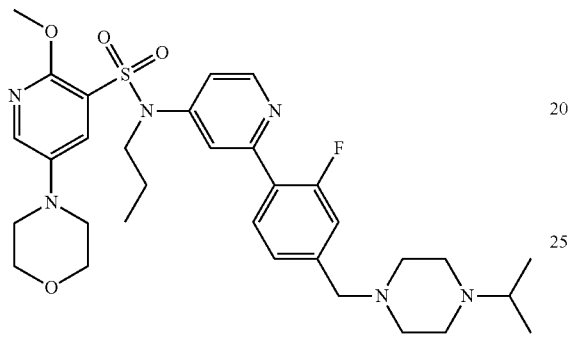

N-(2-(2-fluoro-4-((4-isopropylpiperazin-1-yl)methyl)phenyl)pyridin-4-yl)-2-methoxy-5-morpholinopyridine-3-sulfonamide (50 mg, 0.086 mmol) was dissolved in DMF (1 mL). To this was added potassium carbonate (20 mg, 0.145 mmol) and 1-iodopropane (13 µl, 0.133 mmol). The reaction mixture was stirred at room temperature under an atmosphere of nitrogen for 4 h. Another portion of 1-iodopropane (130 µl, 1.33 mmol) was added and the reaction was stirred at room temperature for 16.5 h. The reaction mixture was partitioned between EtOAc (10 mL) and water (10 mL). The organic extract was dried (hydrophobic frit) and concentrated under reduced pressure. The residue was purified by Mass Directed Automated Preparative HPLC (Method A) to afford the title compound (34 mg) as a light brown solid.

LCMS (Method B) $R_t$=1.32 min, $[M+H]^+$=627.4.

Example 32

N-(2-(2-Fluoro-4-((4-isopropylpiperazin-1-yl)methyl)phenyl)pyridin-4-yl)-N-isopropyl-2-methoxy-5-morpholinopyridine-3-sulfonamide

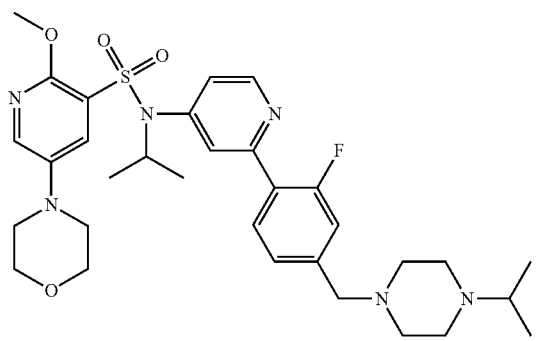 [SMILES: COc1ncc(N2CCOCC2)cc1S(=O)(=O)N(c1ccnc(-c2ccc(CN3CCN(C(C)C)CC3)cc2F)c1)C(C)C]

N-(2-(2-fluoro-4-((4-isopropylpiperazin-1-yl)methyl)phenyl)pyridin-4-yl)-2-methoxy-5-morpholinopyridine-3-sulfonamide (100 mg, 0.171 mmol) was dissolved in DMF (1 mL). To this was added potassium carbonate (100 mg, 0.724 mmol) and 2-iodopropane (0.1 mL, 1.0 mmol). The reaction mixture was heated at 60° C. for 15.5 h. Another portion of 2-iodopropane (0.1 mL, 1.0 mmol) was added and the reaction mixture heated at 60° C. for 9 h. Additional portions of potassium carbonate (100 mg, 0.724 mmol) and 2-iodopropane (0.5 mL, 5.0 mmol) were added and the reaction mixture was heated at 60° C. for 15 h. The reaction mixture was cooled to room temperature, partitioned between EtOAc (20 mL) and water (20 mL). The organic extract was dried (hydrophobic frit) and concentrated under reduced pressure. The residue was purified by Mass Directed Automated Preparative HPLC (Method A) to afford the title compound (39 mg) as an off-white solid.

LCMS (Method B) $R_t$=1.29 min, $[M+H]^+$=627.4.

Example 33

Ethyl 2-(N-(2-(2-fluoro-4-((4-isopropylpiperazin-1-yl)methyl)phenyl)pyridin-4-yl)-2-methoxy-5-morpholinopyridine-3-sulfonamido)acetate

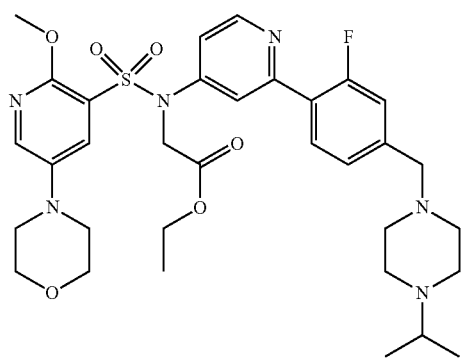 [SMILES: CCOC(=O)CN(c1ccnc(-c2ccc(CN3CCN(C(C)C)CC3)cc2F)c1)S(=O)(=O)c1cc(N2CCOCC2)cnc1OC]

N-(2-(2-fluoro-4-((4-isopropylpiperazin-1-yl)methyl)phenyl)pyridin-4-yl)-2-methoxy-5-morpholinopyridine-3-sulfonamide (50 mg, 0.086 mmol) was dissolved in DMF (1 mL). To this was added potassium carbonate (20 mg, 0.145 mmol) and ethyl 2-chloroacetate (0.014 mL, 0.128 mmol). The reaction mixture was stirred at room temperature for 4 h. Another portion of ethyl 2-chloroacetate (0.14 mL, 1.28 mmol) was added and the reaction was stirred at room temperature for 18 h. The reaction mixture was partitioned between EtOAc (10 mL) and water (10 mL). The organic extract was dried (hydrophobic frit) and concentrated under reduced pressure. The residue was purified by Mass Directed Automated Preparative HPLC (Method A) to afford the title compound (28 mg) as an off-white solid.

LCMS (Method B) $R_t$=1.23 min, $[M+H]^+$=671.4.

Example 34

(N-(2-(2-Fluoro-4-((4-isopropylpiperazin-1-yl)methyl)phenyl)pyridin-4-yl)-2-methoxy-5-morpholinopyridine-3-sulfonamido)methyl pivalate

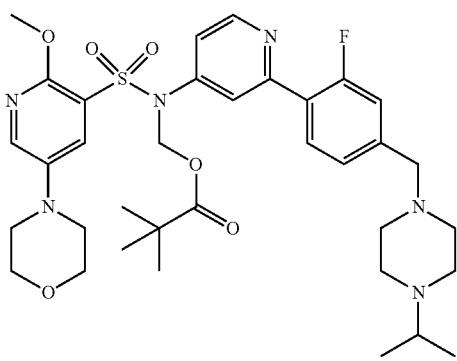 [SMILES: COc1ncc(N2CCOCC2)cc1S(=O)(=O)N(COC(=O)C(C)(C)C)c1ccnc(-c2ccc(CN3CCN(C(C)C)CC3)cc2F)c1]

N-(2-(2-fluoro-4-((4-isopropylpiperazin-1-yl)methyl)phenyl)pyridin-4-yl)-2-methoxy-5-morpholinopyridine-3-sulfonamide (50 mg, 0.086 mmol) was dissolved in DMF (1 mL). To this was added potassium carbonate (20 mg, 0.145 mmol) and chloromethyl pivalate (0.018 mL, 0.128 mmol). The reaction mixture was stirred at room temperature under an atmosphere of nitrogen for 4 h. Another portion of chloromethyl pivalate (0.180 mL, 1.28 mmol) was added and the reaction was stirred at room temperature for 18 h. The reaction mixture was partitioned between EtOAc (10 mL) and water (10 mL). The organic extract was dried (hydrophobic frit) and concentrated under reduced pressure. The residue was purified by Mass Directed Automated Preparative HPLC (Method A) to afford the title compound (32 mg) as an off-white solid.

LCMS (Method B) $R_t$=1.39 min, $[M+H]^+$=699.5.

An additional compound which was prepared is:

Example 35

N-(2-(5-Chloro-2-fluoro-4-((4-isopropylpiperazin-1-yl)methyl)phenyl)pyridin-4-yl)-2-methoxy-5-morpholinopyridine-3-sulfonamide

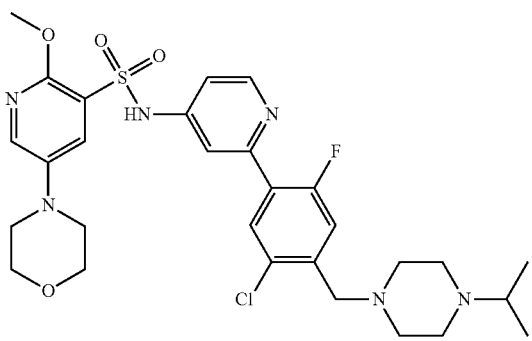 [SMILES: COc1ncc(N2CCOCC2)cc1S(=O)(=O)Nc1ccnc(-c2cc(Cl)c(CN3CCN(C(C)C)CC3)cc2F)c1]

LCMS (Method G) $R_t$=1.60 min, $[M+H]^+$=619.6.

Example 35 may be prepared by the following method:

To a stirred solution of N-(2-chloropyridin-4-yl)-2-methoxy-5-morpholinopyridine-3-sulfonamide (50 mg, 0.130 mmol) in 1,4-dioxane (10 mL) and water (3 mL), was added (5-chloro-2-fluoro-4-((4-isopropylpiperazin-1-yl)methyl)phenyl)boronic acid (300 mg, 0.954 mmol), $K_3PO_4$ (69 mg, 0.326 mmol) at room temperature. The reaction mixture was degassed for 30 min at room temperature. Xphos precatalyst $2^{nd}$ generation (10 mg, 0.013 mmol) was added at room temperature and the reaction mixture was degassed again for 30 min at room temperature. The sealed tube was stirred for 18 h at 110° C. The reaction mixture was filtered through celite, washing with with EtOAc (100 mL) and the filtrate was concentrated in vacuo to afford 300 mg crude residue. The reaction was repeated on larger scale:

To a stirred solution of N-(2-chloropyridin-4-yl)-2-methoxy-5-morpholinopyridine-3-sulfonamide (250 mg, 0.650 mmol) in 1,4-dioxane (30 mL) and water (6 mL), was added (5-chloro-2-fluoro-4-((4-isopropylpiperazin-1-yl)methyl)phenyl)boronic acid (1635 mg, 5.20 mmol), $K_3PO_4$ (344 mg, 1.624 mmol) at room temperature. The reaction mixture was degassed for 30 min at room temperature. Xphos precatalyst 2nd generation (51 mg, 0.065 mmol) was added at room temperature and the reaction mixture was degassed again for 30 min at room temperature. The sealed tube was stirred for 18 h at 110° C. The reaction mixture was filtered through celite, washing with with EtOAc (300 mL) and the filtrate was concentrated in vacuo to afford 2.5 g crude residue. The combined crude residues (2.8 g) were purified by Preparative-HPLC (Method J). Collected fractions were lyophilized to afford the title compound (40 mg) as a white solid.

LCMS (Method G) Rt=1.60 min, $[M+H]^+$=619.6.

Example 36

Rac-N-(2-(4-(((2S,6R)-2,6-dimethylmorpholino)methyl)-2-fluorophenyl)pyridin-4-yl)-2-methoxy-5-morpholinopyridine-3-sulfonamide

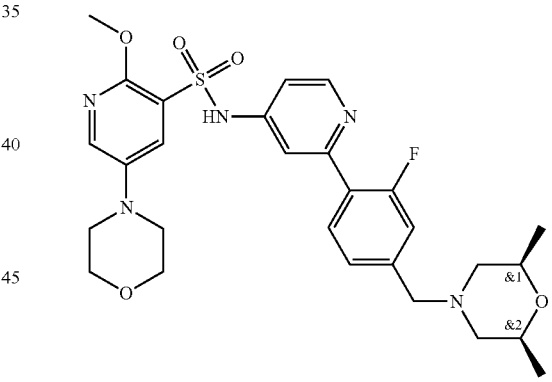

A solution of rac-5-chloro-N-(2-(4-(((2S,6R)-2,6-dimethylmorpholino)methyl)-2-fluorophenyl)pyridin-4-yl)-2-methoxypyridine-3-sulfonamide (0.150 g, 0.288 mmol) and sodium tert-butoxide (0.083 g, 0.864 mmol) in anhydrous toluene (5 mL) was degassed using argon for 15 min. 2-Dicyclohexylphosphino-2',6'-diisopropoxybiphenyl (0.013 g, 0.029 mmol), Pd(OAc)$_2$ (0.003 g, 0.014 mmol) and morpholine (0.050 mL, 0.576 mmol) were added and the mixture was degassed using argon for a further 15 min. The reaction mixture was then stirred in sealed tube at 90° C. for 6 h. The mixture was filtered through celite, washing with EtOAc (2×50 mL) and the solvent removed in vacuo to afford crude material as a brown solid. The reaction was repeated on a 0.08 g scale and the combined crude batches were purified by Preparative-HPLC (Method K). Collected fractions were concentrated in vacuo to afford the title compound (48 mg) as an off-white solid.

LCMS (Method G) $R_t$=1.48 min, $[M+H]^+$=572.2.

Example 37

Rac-N-(2-(4-(((2S,6R)-2,6-dimethylmorpholino)methyl)-2-fluorophenyl)pyridin-4-yl)-2-ethoxy-5-morpholinopyridine-3-sulfonamide

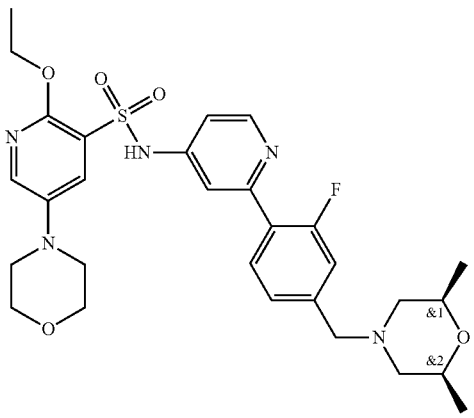 [SMILES: CCOc1ncc(N2CCOCC2)cc1S(=O)(=O)Nc1ccnc(-c2ccc(CN3C[C@@H](C)O[C@@H](C)C3)cc2F)c1]

A solution of rac-5-chloro-N-(2-(4-(((2S,6R)-2,6-dimethylmorpholino)methyl)-2-fluorophenyl)pyridin-4-yl)-2-ethoxypyridine-3-sulfonamide (300 mg, 0.561 mmol) and sodium tert-butoxide (162 mg, 1.682 mmol) in anhydrous toluene (5 mL) was degassed using argon for 15 min. 2-Dicyclohexylphosphino-2',6'-diisopropoxybiphenyl (26 mg, 0.056 mmol), Pd(OAc)$_2$ (6 mg, 0.028 mmol) and morpholine (0.098 mL, 1.121 mmol) were added and the mixture was degassed using argon for a further 5 min. The reaction mixture was then stirred in a sealed tube at 90° C. for 6 h. The mixture was quenched with water (30 mL) and the aqueous phase was extracted with EtOAc (2×30 mL). The combined organic extracts were washed with brine (20 mL), dried over sodium sulfate, filtered and concentrated in vacuo. The crude material was triturated with diethyl ether (2×20 mL) to afford the title compound (58 mg) as a pale yellow solid.

LCMS (Method G) R$_f$=1.58 min, [M+H]$^+$=586.2.

Polymorph Experimental
X-Ray Powder Diffraction (XRPD)

The data were acquired on a PANalytical X'Pert Pro powder diffractometer, model PW3040/60 using an X'Celerator detector. The acquisition conditions were: radiation: Cu Kα, generator tension: 40 kV, generator current: 45 mA, start angle: 2.0° 2θ, end angle: 40.0° 2θ, step size: 0.0167° 2θ, time per step: 31.75 seconds. The sample was prepared by mounting a few milligrams of sample on a silicon wafer (zero background) plate, resulting in a thin layer of powder.

N-(2-(2-Fluoro-4-((4-isopropylpiperazin-1-yl)methyl)phenyl)pyridin-4-yl)-2-methoxy-5-morpholinopyridine-3-sulfonamide (anhydrate—Form 1)

Method A

N-(2-(2-Fluoro-4-((4-isopropylpiperazin-1-yl)methyl)phenyl)pyridin-4-yl)-2-methoxy-5-morpholinopyridine-3-sulfonamide as the anhydrate Form 1 is prepared by the following steps 1. Dissolve net 8 kg of N-(2-(2-fluoro-4-((4-isopropylpiperazin-1-yl)methyl)phenyl)pyridin-4-yl)-2-methoxy-5-morpholinopyridine-3-sulfonamide (hydrate—Form 3) in 6 vol (53.5 kg) DMSO at 70.6° C. in a reaction vessel (R1 used for dissolution).
2. Polish filtration.
3. Use 0.32 vol (2.8 Kg) DMSO to wash R1 and the pipe.
4. Make sure the solution was clear at second reaction vessel (R2 used for crystallisation).
5. Add 3.18 vol (20 Kg) IPA to R2 above 68° C.
6. Cool to 40-42° C. in 0.5 hours.
7. Seed (2.1%)(170 g) with micronized seed.
8. Hold for 27 hours at 40-42° C.
9. Add 16.55 vol (104 Kg) IPA to R2 in 20 hours.
10. Hold for 3 hours at 40-42° C.
11. Cool to about 4-5° C. in 8 hours.
12. Hold for 13.5 hours at 4-5° C.
13. Centrifuge the suspension and wash R2 and cake with 2.55 vol IPA to obtain 8.86 Kg wet solids.
14. Dry under vacuum at 40° C. for 36 hours to obtain 6.46 Kg solids, after sieving, 6.44 Kg solids was obtained.

Method B

N-(2-(2-Fluoro-4-((4-isopropyl piperazin-1-yl)methyl)phenyl)pyridin-4-yl)-2-methoxy-5-morpholinopyridine-3-sulfonamide as the anhydrate Form 1 is prepared by stirring a suspension of N-(2-(2-fluoro-4-((4-isopropyl piperazin-1-yl)methyl)phenyl)pyridin-4-yl)-2-methoxy-5-morpholinopyridine-3-sulfonamide (hydrate—Form 3) in one of a number of solvents such as 1-butanol, 2-methoxyethanol, nitromethane, acetonitrile, methyl acetate or 4-methyl-2-pentanone while cycling the temperature between 40 and 5° C. for four days.

The X-ray powder diffraction (XRPD) data are shown in FIG. 1.

Characteristic peaks for the solid state form are summarised in Table 1 with calculated lattice spacings. Peak positions were measured using Highscore software.

TABLE 1

| 2θ/° | d-spacing/Å |
|---|---|
| 5.2 | 17.1 |
| 8.0 | 11.1 |
| 11.9 | 7.4 |
| 13.2 | 6.7 |
| 14.6 | 6.1 |
| 15.9 | 5.6 |
| 18.9 | 4.7 |
| 25.8 | 3.5 |
| 26.5 | 3.4 |

N-(2-(2-Fluoro-4-((4-isopropylpiperazin-1-yl)methyl)phenyl)pyridin-4-yl)-2-methoxy-5-morpholinopyridine-3-sulfonamide (hydrate—Form 1)

Method A

N-(2-(2-Fluoro-4-((4-isopropylpiperazin-1-yl)methyl)phenyl)pyridin-4-yl)-2-methoxy-5-morpholinopyridine-3-sulfonamide (mixture of forms) is slurried in water for approximately 7 days in the presence of seed. Conversion to the hydrate Form 1 is monitored by FT-Raman and XRPD. The solids are filtered and washed with water to give the hydrate Form 1.

Method B

N-(2-(2-Fluoro-4-((4-isopropylpiperazin-1-yl)methyl)phenyl)pyridin-4-yl)-2-methoxy-5-morpholinopyridine-3-sulfonamide as the hydrate Form 1 is prepared by stirring a suspension of N-(2-(2-fluoro-4-((4-isopropylpiperazin-1-yl)

methyl)phenyl)pyridin-4-yl)-2-methoxy-5-morpholinopyridine-3-sulfonamide (hydrate—Form 3) in one of a number of solvents such as acetonitrile/5% vol water, acetone/5% vol water, THF/5% vol water, 2-propanol/5% vol water, acetonitrile/10% vol water or acetone/10% water while cycling the temperature between 40 and 5° C. for four days.

The hydrate Form 1 is the 1.5 equivalents hydrate.

The X-ray powder diffraction (XRPD) data are shown in FIG. 2.

Characteristic peaks for the solid state form are summarised in Table 2 with calculated lattice spacings. Peak positions were measured using Highscore software.

TABLE 2

| 2θ/° | d-spacing/Å |
|---|---|
| 6.8 | 13.0 |
| 9.4 | 9.5 |
| 11.0 | 8.0 |
| 11.7 | 7.6 |
| 16.1 | 5.5 |
| 16.7 | 5.3 |
| 17.5 | 5.1 |
| 20.1 | 4.4 |
| 20.5 | 4.3 |

N-(2-(2-Fluoro-4-((4-isopropylpiperazin-1-yl)methyl)phenyl)pyridin-4-yl)-2-methoxy-5-morpholinopyridine-3-sulfonamide (anvhdrate—Form 2)

Method A

IPA is added to a solution of N-(2-(2-fluoro-4-((4-isopropylpiperazin-1-yl)methyl)phenyl)pyridin-4-yl)-2-methoxy-5-morpholinopyridine-3-sulfonamide (ca. 1 g) in DMSO (ca. 5.9 ml) until the composition is approximately 60% v/v IPA. The cloudy solution is stirred at 30° C. to gve a thick slurry within 50 minutes. The slurry is stirred over the weekend and the anhydrate Form 2 is isolated by filtration.

Method B

N-(2-(2-Fluoro-4-((4-isopropylpiperazin-1-yl)methyl)phenyl)pyridin-4-yl)-2-methoxy-5-morpholinopyridine-3-sulfonamide as the anhydrate Form 2 is prepared by stirring a suspension of N-(2-(2-fluoro-4-((4-isopropyl pi perazin-1-yl)methyl)phenyl)pyridin-4-yl)-2-methoxy-5-morpholinopyridine-3-sulfonamide (hydrate—Form 3) in one of a number of solvents such as 1-propanol, dimethylsulphoxide, acetone, 2-butanone, chloroform or THF while cycling the temperature between 40 and 5° C. for four days.

The X-ray powder diffraction (XRPD) data are shown in FIG. 3.

Characteristic peaks for the solid state form are summarised in Table 3 with calculated lattice spacings. Peak positions were measured using Highscore software.

TABLE 3

| 2θ/° | d-spacing/Å |
|---|---|
| 6.4 | 13.8 |
| 9.0 | 9.8 |
| 10.4 | 8.5 |
| 11.6 | 7.6 |
| 12.2 | 7.2 |
| 12.6 | 7.0 |
| 13.3 | 6.7 |
| 14.9 | 6.0 |
| 17.7 | 5.0 |

TABLE 3-continued

| 2θ/° | d-spacing/Å |
|---|---|
| 18.4 | 4.8 |
| 22.4 | 4.0 |

N-(2-(2-Fluoro-4-((4-isopropylpiperazin-1-yl)methyl)phenyl)pyridin-4-yl)-2-methoxy-5-morpholinopyridine-3-sulfonamide (hydrate—Form 3)

Pure fractions containing N-(2-(2-fluoro-4-((4-isopropylpiperazin-1-yl)methyl)phenyl)pyridin-4-yl)-2-methoxy-5-morpholinopyridine-3-sulfonamide obtained by chromatography are concentrated and the solids suspended in DCM. The solvent is removed in vacuo and the solid dried at ca. 43-44° C. for 24 hours to give N-(2-(2-fluoro-4-((4-isopropylpiperazin-1-yl)methyl)phenyl)pyridin-4-yl)-2-methoxy-5-morpholinopyridine-3-sulfonamide as the hydrate Form 3.

The hydrate Form 3 is the 0.225 equivalents hydrate.

The X-ray powder diffraction (XRPD) data are shown in FIG. 4.

Characteristic peaks for the solid state form are summarised in Table 4 with calculated lattice spacings. Peak positions were measured using Highscore software.

TABLE 4

| 2θ/° | d-spacing/Å |
|---|---|
| 8.1 | 10.9 |
| 9.1 | 9.7 |
| 10.2 | 8.7 |
| 11.7 | 7.6 |
| 12.7 | 7.0 |
| 14.5 | 6.1 |
| 16.2 | 5.5 |
| 23.5 | 3.8 |
| 24.3 | 3.7 |

Biological Data

PI3K HTRF Assay

The binding of compounds to PI3K-alpha/beta/delta/gamma is determined by homogeneous time resolved fluorescence (HTRF) assays as follows;

Briefly, solid compound is dissolved in 100% DMSO at a concentration of 2 mM. Dilutions are prepared in 100% DMSO using a 1 in 4 serial step dilution. The dilutions are transferred to black low volume Greiner assay plates ensuring that the DMSO concentration is constant across the plate at 1% (0.1 ul/well).

PI3K Reaction Buffer (contains 50 mM HEPES pH7.0 (NaOH), 150 mM NaCl, 10 mM MgCl2, 2.3 mM sodium cholate, 10 μM CHAPS made up in milliQ water). Fresh DTT is added at a final concentration of 1 mM on the day of use. Wortmannin at a concentration sufficient to produce 100% inhibition (8.33e-6 M) is added to column 18 of compound plates.

Enzyme solutions: 1× PI3K assay Buffer containing:
550 pM PI3K-Alpha enzyme (275 pM final assay concentration)
800 pM PI3K-Beta enzyme (400 pM final assay concentration)
3 nM PI3K-Delta enzyme (1.5 nM final assay concentration)
10 nM PI3K-Gamma enzyme (5 nM final assay concentration)

These concentrations are optimal to achieve a signal: background of between 1.5-4.5. The enzyme solution is added to columns 1-24 (3 ul/well) and plates are incubated for 15 minutes at room temperature.

Substrate solution: 1× PI3K assay buffer containing:
PI3K-Alpha: 500 μM ATP, 20 μM PIP2 and 120 nM biotin-PIP3. (Final assay concentrations are 250 μM ATP, 10 μM PIP2 (both at $K_m$) and 40 nM biotin-PIP3)
PI3K-Beta: 800 μM ATP, 20 μM PIP2 and 120 nM biotin-PIP3. (Final assay concentrations are 400 μM ATP, 10 μM PIP2 (both at $K_m$) and 40 nM biotin-PIP3)
PI3K-Delta: 160 pM ATP, 20 μM PIP2 and 120 nM biotin-PIP3. (Final assay concentrations are 80 μM ATP, 10 μM PIP2 (both at $K_m$) and 40 nM biotin-PIP3)
PI3K-Gamma: 30 μM ATP, 20 μM PIP2 and 120 nM biotin-PIP3. (Final assay concentrations are 15 μM ATP, 10 μM PIP2 (both at $K_m$) and 40 nM biotin-PIP3)

This is added to all wells and plates are incubated for 1 hour at room temperature.

Detection solution: PI3K Detection Buffer (contains 50 mM HEPES pH7.0 (HCl), 150 mM NaCl, 2.3 mM sodium cholate, 10 μM CHAPS, 240 mM potassium fluoride) containing 2 mM DTT (2× final concentration), 90 nM GRP-1 PH domain, 300 nM Streptavidin-APC and 24 nM Europium-anti-GST (6× final concentrations)

This is mixed left at room temperature (protected from light).

STOP solution: PI3K STOP Buffer (contains 50 mM HEPES pH7.0 (HCl), 150 mM NaCl, 2.3 mM sodium cholate, 10 μM CHAPS, 150 mM EDTA).

Detection solution is diluted 1:1 with STOP solution and added to all wells (3 ul/well). Plates are covered and incubated on the bench for 45-60 minutes. Plates are read on a PerkinElmer Envision, measuring TR-FRET between the complex formed between the GST-tagged PH domain and biotinylated PIP3 which both recruit fluorophores (Europium-labelled anti-GST & Strep-APC respectively). In the presence of an inhibitor, this complex is disrupted by the competitive action of non-biotinylated PIP3 (formed in the assay by the phosphorylation of PIP2 by the kinase & ATP). From this, the ratio of acceptor/donor was calculated (Aex=317 nm, Aem donor=615 nm, em acceptor=665 nm) and used for data analysis.

The compounds and salts of Examples 1 to 37 were tested in the PI3K Alpha, Beta, Delta and/or Gamma assays above or similar assays and were found to have a mean $pIC_{50}$ in the PI3K Delta assay of at least 5 or greater. Examples 1 to 3, 5 to 9, 12 to 19, 21 to 27 and 35 to 37 were found to have a mean $pIC_{50}$ in the PI3K Delta assay of at least 8.5 or greater. For example, Example 1 was found to have a mean $pIC_{50}$ in the PI3K Delta assay of 9.

What is claimed is:

1. A method of treating a disorder mediated by inappropriate PI3-kinase activity comprising administering an amount of a compound of formula (I):

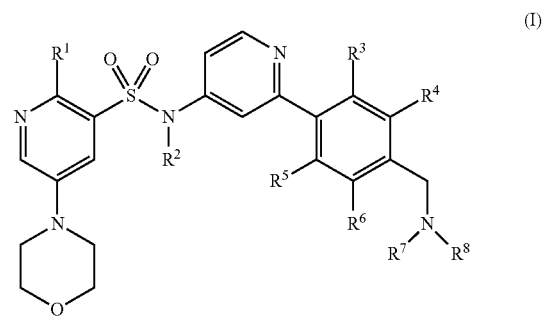

wherein
$R^1$ is $C_{1-6}$alkoxy or —N($C_{1-6}$alkyl)$_2$,
$R^2$ is hydrogen or $C_{1-6}$alkyl optionally substituted by —C(O)O$C_{1-6}$alkyl or —OC(O)$C_{1-6}$alkyl,
$R^3$, $R^4$, $R^5$ and $R^6$ are each independently selected from hydrogen and halogen;
$R^7$ and $R^8$ are each independently $C_{1-6}$alkyl, or
$R^7$ and $R^8$, together with the nitrogen atom to which they are attached, are linked to form a 5- or 6-membered heterocyclyl wherein the 5- or 6-membered heterocyclyl optionally contains a further nitrogen atom and is optionally substituted by $C_{3-6}$cycloalkyl, 4- to 6-membered heterocyclyl containing one or two heteroatoms independently selected from oxygen and nitrogen, or $C_{1-6}$alkyl wherein the $C_{1-6}$alkyl is optionally substituted by hydroxy or $C_{1-6}$alkoxy, or
$R^7$ and $R^8$, together with the nitrogen atom to which they are attached, are linked to form a 5- or 6-membered heterocyclyl wherein the 5- or 6-membered heterocyclyl contains an oxygen atom and is optionally substituted by one or two substituents independently selected from $C_{1-6}$alkyl;
or a pharmaceutically acceptable salt thereof, to a patient in need thereof, by inhibiting PI3-kinase activity and wherein said disorder mediated by inappropriate PI3-kinase activity is selected from the group consisting of asthma and COPD.

2. A method according to claim 1 wherein the disorder mediated by inappropriate PI3-kinase activity is asthma.

3. A method according to claim 1 wherein the disorder mediated by inappropriate PI3-kinase activity is COPD.

* * * * *